US012718936B2

(12) United States Patent
Shelton, IV et al.

(10) Patent No.: US 12,718,936 B2
(45) Date of Patent: Aug. 25, 2026

(54) MACHINE LEARNING TO IMPROVE ARTIFICIAL INTELLIGENCE ALGORITHM ITERATIONS

(71) Applicant: Cilag GmbH International, Zug (CH)

(72) Inventors: Frederick E. Shelton, IV, Hillsboro, OH (US); Demetrius Harris, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 754 days.

(21) Appl. No.: 17/156,293

(22) Filed: Jan. 22, 2021

(65) Prior Publication Data

US 2022/0238216 A1 Jul. 28, 2022

(51) Int. Cl.

| | |
|---|---|
| ***G16H 40/40*** | (2018.01) |
| ***G06F 8/658*** | (2018.01) |
| ***G06N 20/00*** | (2019.01) |
| ***G16H 40/60*** | (2018.01) |

(52) U.S. Cl.

CPC ............ *G16H 40/40* (2018.01); *G06F 8/658* (2018.02); *G06N 20/00* (2019.01); *G16H 40/60* (2018.01)

(58) Field of Classification Search

None

See application file for complete search history.

(56) References Cited

U.S. PATENT DOCUMENTS

| | | | |
|---|---|---|---|
| 6,317,731 | B1 | 11/2001 | Luciano |
| 8,512,260 | B2 | 8/2013 | Grudic et al. |
| 8,696,616 | B2 | 4/2014 | Baynham et al. |
| 8,864,009 | B2 | 10/2014 | Shelton et al. |

(Continued)

FOREIGN PATENT DOCUMENTS

| | | | |
|---|---|---|---|
| CN | 111616803 | A | 9/2020 |
| EP | 3501459 | A2 | 6/2019 |

(Continued)

OTHER PUBLICATIONS

Appelboom et al., "The Promise of Wearable Activity Sensors to Define Patient Recovery", Journal of Clinical Neuroscience, vol. 21, Jul. 1, 2014, pp. 1089-1093.

Chen et al., "Type of Pelvic Disease as a Risk Factor for Surgical Site Infection in Women Undergoing Hysterectomy", Journal of Minimally Invasive Gynecology, vol. 26, No. 6, Sep. 1, 2019, pp. 1149-1156.

(Continued)

*Primary Examiner* — Lena Najarian

(74) *Attorney, Agent, or Firm* — Condo Roccia Koptiw LLP

(57) ABSTRACT

A computing system may be provided for applying machine learning to a data collection to improve a surgical outcome. The computing system may perform a number of actions. An indication that an operational behavior of a surgical device may be suboptimal may be determined from a data collection that may include one or more biomarkers. A model that may optimize and/or improve the behavioral operation of the surgical device to improve a surgical outcome may be determined using machine learning and the data collection. The model may be updated using feedback given by a healthcare provider to improve the model. The control program update may be determined using the model and the data collection. The control program update may be configured to alter a manner in which a control program operates the surgical device during the surgical procedure. The control program update may be sent to the surgical device.

13 Claims, 24 Drawing Sheets

(56) References Cited

U.S. PATENT DOCUMENTS 9,011,427 B2 4/2015 Price et al.
9,072,535 B2 7/2015 Shelton et al.
9,123,155 B2 9/2015 Cunningham et al.
9,345,481 B2 5/2016 Hall et al.
9,621,357 B2 4/2017 Williams et al.
9,700,317 B2 7/2017 Aronhalt et al.
9,974,903 B1 5/2018 Davis et al.
10,535,020 B2 1/2020 Experton
2002/0111830 A1 8/2002 Tahan
2003/0139942 A1 7/2003 Rakshit et al.
2005/0021369 A1 1/2005 Cohen et al.
2008/0064965 A1 3/2008 Jay et al.
2008/0300915 A1 12/2008 Molmenti et al.
2008/0306763 A1* 12/2008 James .................... G16H 40/67 705/2
2009/0299924 A1 12/2009 Bauer et al.
2011/0054290 A1 3/2011 Derchak
2011/0152759 A1 6/2011 Clymer et al.
2012/0132211 A1 5/2012 Halperin et al.
2012/0253360 A1* 10/2012 White .................... A61B 34/35 606/130
2012/0265549 A1 10/2012 Virolainen
2012/0310670 A1 12/2012 Pruitt
2012/0323592 A1* 12/2012 Bechtel ................... G16Z 99/00 705/2
2013/0137941 A1 5/2013 Schardey
2013/0245481 A1 9/2013 Tremper
2013/0265919 A1 10/2013 Pochiraju et al.
2014/0051921 A1 2/2014 Miller et al.
2014/0081659 A1 3/2014 Nawana et al.
2014/0236159 A1 8/2014 Haider et al.
2014/0263541 A1 9/2014 Leimbach et al.
2014/0263551 A1 9/2014 Hall et al.
2014/0263552 A1 9/2014 Hall et al.
2015/0173697 A1 6/2015 Parks et al.
2015/0302536 A1 10/2015 Wahl et al.
2016/0030240 A1 2/2016 Gonenc et al.
2016/0110504 A1 4/2016 Fialkov
2016/0303340 A1 10/2016 Sinderby et al.
2017/0068785 A1 3/2017 Experton et al.
2017/0119300 A1 5/2017 Conner
2017/0228501 A1 8/2017 Turner, Jr. et al.
2017/0258408 A1 9/2017 Stapelfeldt
2017/0281064 A1 10/2017 Bayon
2017/0296213 A1 10/2017 Swensgard et al.
2017/0360358 A1 12/2017 Amiot et al.
2018/0028088 A1 2/2018 Garbey et al.
2018/0042681 A1 2/2018 Jagga
2018/0090029 A1 3/2018 Fisher et al.
2018/0102960 A1 4/2018 Rickert et al.
2018/0168579 A1 6/2018 Aronhalt et al.
2018/0256051 A1 9/2018 Stone et al.
2018/0286521 A1 10/2018 Fong
2018/0360451 A1 12/2018 Shelton, IV et al.
2018/0360452 A1 12/2018 Shelton et al.
2019/0013099 A1 1/2019 Esterberg et al.
2019/0059932 A1 2/2019 Isosaki et al.
2019/0079916 A1 3/2019 Eyigoz
2019/0200844 A1 7/2019 Shelton et al.
2019/0200981 A1 7/2019 Harris et al.
2019/0201033 A1 7/2019 Yates et al.
2019/0201043 A1 7/2019 Shelton, IV et al.
2019/0201115 A1 7/2019 Shelton, IV et al.
2019/0201130 A1* 7/2019 Shelton, IV ........... G16H 10/60
2019/0201136 A1 7/2019 Shelton et al.
2019/0201137 A1 7/2019 Shelton et al.
2019/0206563 A1 7/2019 Shelton, IV et al.
2019/0206569 A1 7/2019 Shelton et al.
2019/0216452 A1 7/2019 Nawana et al.
2019/0258672 A1 8/2019 Sadrieh
2019/0259476 A1 8/2019 Armijos
2019/0392162 A1 12/2019 Stern et al.
2020/0131581 A1 4/2020 Jain et al.
2020/0143594 A1 5/2020 Lal et al.
2020/0168313 A1 5/2020 Westerhoff
2020/0168334 A1 5/2020 Mowery
2020/0184850 A1 6/2020 Pugh
2020/0188028 A1 6/2020 Feiner et al.
2020/0205900 A1* 7/2020 Buckland ............... G06V 10/82
2020/0246081 A1 8/2020 Johnson et al.
2020/0268472 A1 8/2020 Wolf et al.
2020/0273581 A1 8/2020 Wolf et al.
2020/0315734 A1 10/2020 El Amm
2020/0394334 A1 12/2020 Bulut et al.
2020/0397515 A1 12/2020 Frimer et al.
2021/0000558 A1 1/2021 Penny et al.
2021/0005321 A1 1/2021 Hwang
2021/0015432 A1 1/2021 Konno et al.
2021/0098088 A1 4/2021 Hashimoto et al.
2021/0228276 A1* 7/2021 Giraldez .................. G09B 1/00
2021/0241869 A1 8/2021 Muse et al.
2021/0346853 A1 11/2021 Hull et al.
2021/0378752 A1* 12/2021 Paul ..................... G02B 27/017
2022/0233102 A1 7/2022 Shelton, IV et al.
2022/0233119 A1 7/2022 Shelton, IV et al.
2022/0233135 A1 7/2022 Shelton, IV et al.
2022/0233136 A1 7/2022 Shelton, IV et al.
2022/0233151 A1 7/2022 Shelton, IV et al.
2022/0233191 A1 7/2022 Shelton, IV et al.
2022/0233214 A1 7/2022 Shelton, IV et al.
2022/0233241 A1 7/2022 Shelton, IV et al.
2022/0233244 A1 7/2022 Shelton, IV et al.
2022/0233252 A1 7/2022 Shelton, IV et al.
2022/0233253 A1 7/2022 Shelton, VI et al.
2022/0233254 A1 7/2022 Shelton, IV et al.
2022/0233267 A1 7/2022 Shelton, IV et al.
2022/0237999 A1 7/2022 Shelton, IV et al.
2022/0238197 A1 7/2022 Shelton, IV et al.
2022/0238202 A1 7/2022 Shelton, IV et al.
2022/0238209 A1 7/2022 Shelton, IV et al.
2022/0238235 A1 7/2022 Shelton, IV et al.
2022/0239577 A1 7/2022 Shelton, IV
2022/0240869 A1 8/2022 Shelton, IV et al.
2022/0241028 A1 8/2022 Shelton, IV et al.

FOREIGN PATENT DOCUMENTS

EP 3 671 759 A1 6/2020
JP 2019-525276 A 9/2019
JP 2019-177134 A 10/2019
WO 2007/096931 A2 8/2007
WO 2017/098503 A1 6/2017
WO 2017/147652 A1 9/2017
WO 2019130085 A1 7/2019
WO WO-2019130075 A1 * 7/2019 ............ A61B 34/25
WO 2019147718 A1 8/2019
WO 2019181432 A1 9/2019
WO 2020075546 A1 4/2020
WO 2020/092701 A2 5/2020
WO 2020/180917 A1 9/2020
WO 2021/007418 A2 1/2021
WO 2021/126163 A1 6/2021

OTHER PUBLICATIONS

Erowele et al., "Treatment Options for Postoperative Ileus", US Pharmacist, vol. 35, 2010.
Sugino et al., "Surgical Task Analysis of Simulated Laparoscopic Cholecystectomy with a Navigation System", International Journal of Computer Assisted Radiology and Surgery, vol. 9, Jan. 14, 2014, pp. 825-836.
U.S. Appl. No. 17/156,287, filed Jan. 22, 2021, Shelton, et al.
U.S. Appl. No. 17/156,296, filed Jan. 22, 2021, Shelton, et al.
U.S. Appl. No. 17/156,300, filed Jan. 22, 2021, Shelton, et al.
U.S. Appl. No. 17/156,304, filed Jan. 22, 2021, Shelton, et al.
U.S. Appl. No. 17/156,266, filed Jan. 22, 2021, Shelton, et al.
U.S. Appl. No. 17/156,318, filed Jan. 22, 2021, Shelton, et al.
U.S. Appl. No. 17/156,309, filed Jan. 22, 2021, Shelton, et al.
U.S. Appl. No. 17/156,306, filed Jan. 22, 2021, Shelton, et al.
U.S. Appl. No. 17/156,321, filed Jan. 22, 2021, Shelton, et al.
U.S. Appl. No. 17/156,281, filed Jan. 22, 2021, Shelton, et al.
U.S. Appl. No. 17/156,272, filed Jan. 22, 2021, Shelton, et al.

(56) References Cited

OTHER PUBLICATIONS

U.S. Appl. No. 17/156,279, filed Jan. 22, 2021, Shelton, et al.
U.S. Appl. No. 17/156,284, filed Jan. 22, 2021, Shelton, et al.
U.S. Appl. No. 17/156,282, filed Jan. 22, 2021, Shelton, et al.
U.S. Appl. No. 17/156,269, filed Jan. 22, 2021, Shelton, et al.
U.S. Appl. No. 17/156,286, filed Jan. 22, 2021, Shelton, et al.
U.S. Appl. No. 17/156,324, filed Jan. 22, 2021, Shelton, et al.
U.S. Appl. No. 17/156,329, filed Jan. 22, 2021, Shelton, et al.
U.S. Appl. No. 17/156,289, filed Jan. 22, 2021, Shelton, et al.
U.S. Appl. No. 17/156,298, filed Jan. 22, 2021, Shelton, et al.
U.S. Appl. No. 17/156,274, filed Jan. 22, 2021, Shelton, et al.
U.S. Appl. No. 17/156,278, filed Jan. 22, 2021, Shelton, et al.
U.S. Appl. No. 17/062,509, filed Oct. 2, 2020, Shelton, et al.
U.S. Appl. No. 62/611,341, filed Dec. 28, 2017, Shelton, et al.
Aliverti, et al., "Wearable technology: role in respiratory health and disease", Breathe, 2017, 10 pages.
Kazamias, et al., "Blood pressure measurement with Doppler ultrasonic flowmeter", Journal of Applied Physiology vol. 30, No. 4, Apr. 1971, 1 page.
Cerfolio, et a., "Prospective Randomized Trial Compares Suction Versus Water Seal for Air Leaks", General Thoracic, May 1, 2001, 5 pages.
Brunelli, et al., "A Scoring System to Predict the Risk of Prolonged Air Leak After Lobectomy", General Thoracic, 2010, 6 pages.
Jacob, et al., "Clinical applications of magnets on cardiac rhythm management devices", European Society of Cardiology, May 26, 2011, 9 pages.
Carroll, et al., "Multi-Sensor Esophageal Temperature Probe Used During Radiofrequency Ablation for Atrial Fibrillation is Associated with Increased Intraluminal Temperature Detection and Increased Risk of Esophageal Injury Compared to Single-Sensor Probe", Journal of Cardiovascular Electrophysiology vol. 24, No. 9, Sep. 2013, 8 pages.
Singh, et al., "Esophageal Injury and Temperature Monitoring During Atrial Fibrillation Ablation", American Heart Association, Circulation: Arrhythmia and Electrophysiology, vol. 1, issue 3, Aug. 1, 2008, 7 pages.
Nair, et al., "Atrioesophageal Fistula: A Review", Journal of Atrial Fibrillation vol. 8, Issue 3, Oct. Nov. 2015, 6 pages.
Drewry, et al., "Body temperature patterns as a predictor of hospital-acquired sepsis in afebrile adult intensive care unit patients: a case-control study", Critical Care 2013, 11 pages.
Diduch, et al., "Synchronization of Data Streams in Distributed Realtime Multimodal Signal Processing Environments Using Commodity Hardware", 4 pages.
Kwon, et al., "Electrocardiogram Sampling Frequency Range Acceptable for Heart Rate Variability Analysis", The Korean Society of Medical Informatics, 2018, 9 pages.
Pouchard, et al., "Open Standards for Sensor Information Processing", Oak Ridge National Laboratory, Jul. 2009, 49 pages.
Jinbin, "Feedback Loops—Friend or Foe?", Available at <https://medium.com/unpackai/feedback-loops-friend-or-foe-81a552203228>, Oct. 19, 2020, pp. 1-3.
Li, et al., "Attention-Aware Robotic Laparoscope for Human-Robot Cooperative Surgery", IEEE International Conference on Robotics and Biomimetics (ROBIO), Dec. 12, 2013, 6 pages.
"International Search Report and Written Opinion, received for PCT Application No. PCT/IB2022/050508", Mar. 24, 2022, 15 pages.
"International Search Report and Written Opinion, received for PCT Application No. PCT/IB2022/050511", Mar. 25, 2022, 17 pages.
"International Search Report and Written Opinion, received for PCT Application No. PCT/IB2022/050513", Mar. 25, 2022, 16 pages.
"International Search Report and Written Opinion, received for PCT Application No. PCT/IB2022/050515", May 17, 2022, 13 pages.
"International Search Report and Written Opinion, received for PCT Application No. PCT/IB2022/050518", Mar. 25, 2022, 12 pages.
"International Search Report and Written Opinion, received for PCT Application No. PCT/IB2022/050522", May 2, 2022, 17 pages.
"International Search Report and Written Opinion, received for PCT Application No. PCT/IB2022/050524", Apr. 21, 2022, 16 pages.
"International Search Report and Written Opinion, received for PCT Application No. PCT/IB2022/050525", May 4, 2022, 12 pages.
"International Search Report and Written Opinion, received for PCT Application No. PCT/IB2022/050529", Apr. 20, 2022, 9 pages.
"International Search Report and Written Opinion, received for PCT Application No. PCT/IB2022/050531", Apr. 13, 2022, 9 pages.
"International Search Report and Written Opinion, received for PCT Application No. PCT/IB2022/050533", Apr. 13, 2022, 11 pages.
"International Search Report and Written Opinion, received for PCT Application No. PCT/IB2022/050534", Apr. 22, 2022, 12 pages.
"International Search Report and Written Opinion, received for PCT Application No. PCT/IB2022/050537", Apr. 7, 2022, 12 pages.
"International Search Report and Written Opinion, received for PCT Application No. PCT/IB2022/050541", Jul. 26, 2022, 16 pages.
"International Search Report and Written Opinion, received for PCT Application No. PCT/IB2022/050542", May 2, 2022, 13 pages.
"International Search Report and Written Opinion, received for PCT Application No. PCT/IB2022/050543", Apr. 22, 2022, 17 pages.
"International Search Report and Written Opinion, received for PCT Application No. PCT/IB2022/050544", Apr. 28, 2022, 17 pages.
Davies, et al., "Preoperative Optimization of the High-Risk Surgical Patient", British Journal of Anaesthesia, vol. 93, Advance Access publication, Apr. 30, 2004, pp. 121-128.
Foroutan, et al., "An increase in heart rate variability can be an index for end point of resuscitation in trauma patients", Chinese Journal of Traumatology 22, vol. 22, No. 3, Apr. 16, 2019, pp. 134-137.
Gehrich, et al., "Risk of postoperative urinary tract infections following midurethral sling operations in women undergoing hysterectomy", International Urogynecology Journal, vol. 27, No. 3, Oct. 14, 2015, pp. 483-490.
Kirchhoff, et al., "Complications in Colorectal Surgery: Risk Factors and Preventive Strategies", Patient Safety in vol. 04, Mar. 25, 2010, 13 pages.
Levine, et al., "Computer Automated Total Periopertative Situational Awareness and Safety System", Computer Assisted Radiology and Surgery, International Series, vol. 1281, Jun. 2005, 6 pages.
Macefield, et al., "Development of a Single, Practical Measure of Surgical Site Infection (SSI) for Patient Report or Completion", Journal of Infection Prevention, vol. 18, No. 4, 2017, pp. 170-179.
Petrella, et al., "Predicting Prolonged Air Leak After Standard Pulmonary Lobectomy: Computed Tomography and Risk Factors Stratification", The Surgeon, vol. 9, 2011, pp. 72-77.
Schug,et al., "Postoperative Pain Management of the Obese Patient", Best Practice & Research Clinical vol. 25, No. 1, 2011, pp. 73-81.
Stoppelkamp, et al., "Identification of Predictive Early Biomarkers for Sterile-SIRS after Cardiovascular Surgery", PLOS vol. 10, No. 8, Aug. 11, 2015, 20 pages.
Veličković, V. J. "The Predictive Performance of the Possum Scoring System and Early Indicators of Peripheral Perfusion for Complications After Major Abdominal Surgery", University of Belgrade, School of Medicine, 2019, pp. 1-163.

* cited by examiner 20300
20302
20303
20304
20305
20303

20310
20312

20320
20322

20315
20317
20317

MACHINE LEARNING TO IMPROVE ARTIFICIAL INTELLIGENCE ALGORITHM ITERATIONS

CROSS-REFERENCE TO RELATED APPLICATIONS

This application is related to the following, filed contemporaneously, the contents of each of which are incorporated by reference herein:

U.S. patent application Ser. No. 17/156,287, filed Jan. 22, 2021, entitled METHOD OF ADJUSTING A SURGICAL PARAMETER BASED ON BIOMARKER MEASUREMENTS.

BACKGROUND

Sensing systems, which may include wearable devices, may be used to track one or more biomarkers for a patient. The biomarkers may be used by a health care provider (HCP) to diagnose a disease or determine an issue, such as a surgical complication, with the patient. Machine learning may be used to improve data, such as biomarkers, from the wearables. But training machine learning may be timing consuming and may be inconvenient.

SUMMARY

Disclosed herein are methods, systems, and apparatus to provide machine learning that may be used to improve artificial intelligence algorithms, may reduce the iterations used to train artificial intelligence algorithms, and/or may make training machine learning less timing consuming. Adaptive learning algorithms may be used to aggregation one or more data streams. Adaptive learning algorithms may be used to generate and/or determine meta-data from a data collection. Adaptive learning algorithms may be used to process data, determine an efficient way to transport data, determine an efficient way to store data, and the like. Adaptive learning may be used to determine one or more improvements from a previous machine learning analysis. Improvements in the collection and or processing of sensor feeds, data feeds, and or biomarker feeds may be used to produce improved power instrument algorithms. For example, improvements may be used to produce improved power instrument algorithms based on a desired outcome.

A computing system and/or a method may be used for applying machine learning to a data collection to improve a surgical outcome. The computing system may comprise a processor that may perform the method. A data collection that includes one or more biomarkers may be determined. The data collection and/or the one or more biomarkers may indicate that an operational behavior of a surgical device may be suboptimal. A model may be determined using machine learning and the data collection. The model may optimize and/or improve the operational behavior of the surgical device to improve a surgical outcome. The model may be updated using a feedback given by a healthcare provider (HCP) to improve the model. A control program update may be determined using the model and the collection data. The control program update may be configured to alter a manner in which a control program operates the surgical device during a surgical procedure. The control program update may be sent to the surgical device.

A computing system and/or method may be used for applying machine learning to a data collection to improve a surgical outcome. The computing system may comprise a processor that may perform the method. It may be determined from a data collection that includes one or more biomarkers that an operational behavior of a surgical advice may be suboptimal. A model that optimizes and/or improves the operational behavior of the surgical device and may predict a surgical complication may be determined using machine learning and the data collection. The model may be updated using a feedback given by a healthcare provider (HCP) to improve the model. The control program update may be determined using the model and the data collection. The control program update may be configured to alter a manner in which a control program may operate the surgical device during a surgical procedure to prevent the surgical complication. The control program update may be sent to the surgical device.

A computing system and or a method may be used for applying machine learning to a data collection to improve a surgical outcome. The computing system may comprise a processor that may perform the method. It may be determined that an operational behavior of a surgical device may be suboptimal using a surgical device data and a biomarker from a sensing system. A model that optimizes and/or improves the operational behavior of a surgical device to improve the surgical outcome may be determined using machine learning, the surgical device data, and the biomarker. The model may be updated using a feedback given by a healthcare provider (HCP) to improve the model. A control program update may be determined using the biomarker and the surgical device data. The control program update may be configured to alter a manner in which a control program may operate the surgical device during a surgical procedure. The control program update may be sent to the surgical device.

This Summary is provided to introduce a selection of concepts in a simplified form that are further described herein in the Detailed Description. This Summary is not intended to identify key features or essential features of the claimed subject matter, nor is it intended to be used to limit the scope of the claimed subject matter. Other features are described herein.

DETAILED DESCRIPTION

Figure 1A:
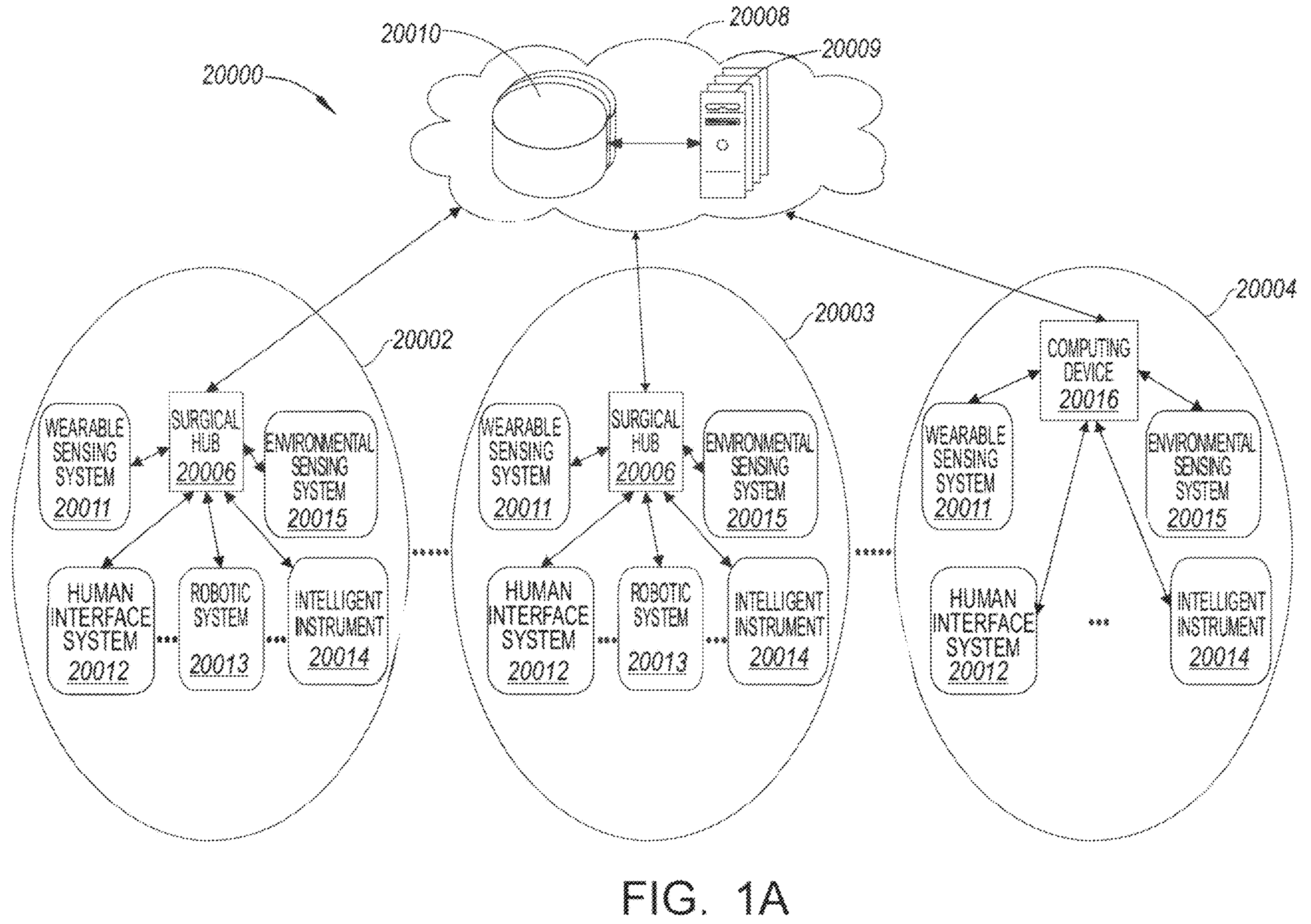
FIG. 1A is a block diagram of a computer-implemented patient and surgeon monitoring system.

FIG. 1A is a block diagram of a computer-implemented patient and surgeon monitoring system 20000. The patient and surgeon monitoring system 20000 may include one or more surgeon monitoring systems 20002 and a one or more patient monitoring systems (e.g., one or more controlled patient monitoring systems 20003 and one or more uncontrolled patient monitoring systems 20004). Each surgeon monitoring system 20002 may include a computer-implemented interactive surgical system. Each surgeon monitoring system 20002 may include at least one of the following: a surgical hub 20006 in communication with a cloud computing system 20008, for example, as described in FIG. 2A. Each of the patient monitoring systems may include at least one of the following: a surgical hub 20006 or a computing device 20016 in communication with a could computing system 20008, for example, as further described in FIG. 2B and FIG. 2C. The cloud computing system 20008 may include at least one remote cloud server 20009 and at least one remote cloud storage unit 20010. Each of the surgeon monitoring systems 20002, the controlled patient monitoring systems 20003, or the uncontrolled patient monitoring systems 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more surgeon sensing systems, and/or one or more patient sensing systems. The environmental sensing system 20015 may include one or more devices, for example, used for measuring one or more environmental attributes, for example, as further described in FIG. 2A. The robotic system 20013 (same as 20034 in FIG. 2A) may include a plurality of devices used for performing a surgical procedure, for example, as further described in FIG. 2A.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

Figure 1B:
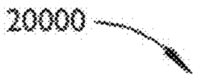
FIG. 1B is a block diagram of an example relationship among sensing systems, biomarkers, and physiologic systems.

FIG. 1B is a block diagram of an example relationship among sensing systems 20001, biomarkers 20005, and physiologic systems 20007. The relationship may be employed in the computer-implemented patient and surgeon monitoring system 20000 and in the systems, devices, and methods disclosed herein. For example, the sensing systems 20001 may include the wearable sensing system 20011 (which may include one or more surgeon sensing systems and one or more patient sensing systems) and the environmental sensing system 20015 as discussed in FIG. 1A. The one or more sensing systems 20001 may measure data relating to various biomarkers 20005. The one or more sensing systems 20001 may measure the biomarkers 20005 using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers 20005 as described herein using one of more of the following sensing technologies: photoplethysmography, electrocardiography, electroencephalography, colorimetry, impedimentary, potentiometry, amperometry, etc.

The biomarkers 20005 measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers 20005 may relate to physiologic systems 20007, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and surgeon monitoring system 20000, for example. The information from the biomarkers may be determined and/or used by the computer-implemented patient and surgeon monitoring system 20000 to improve said systems and/or to improve patient outcomes, for example.

The one or more sensing systems 20001, biomarkers 20005, and physiological systems 20007 are described in more detail below.

Sleep

A sleep sensing system may measure sleep data, including heart rate, respiration rate, body temperature, movement, and/or brain signals. The sleep sensing system may measure sleep data using a photoplethysmogram (PPG), electrocardiogram (ECG), microphone, thermometer, accelerometer, electroencephalogram (EEG), and/or the like. The sleep sensing system may include a wearable device such as a wristband.

Based on the measured sleep data, the sleep sensing system may detect sleep biomarkers, including but not limited to, deep sleep quantifier, REM sleep quantifier, disrupted sleep quantifier, and/or sleep duration. The sleep sensing system may transmit the measured sleep data to a processing unit. The sleep sensing system and/or the processing unit may detect deep sleep when the sensing system senses sleep data, including reduced heart rate, reduced respiration rate, reduced body temperature, and/or reduced movement. The sleep sensing system may generate a sleep quality score based on the detected sleep physiology.

In an example, the sleep sensing system may send the sleep quality score to a computing system, such as a surgical hub. In an example, the sleep sensing system may send the detected sleep biomarkers to a computing system, such as a surgical hub. In an example, the sleep sensing system may send the measured sleep data to a computing system, such as a surgical hub. The computing system may derive sleep physiology based on the received measured data and generate one or more sleep biomarkers such as deep sleep quantifiers. The computing system may generate a treatment plan, including a pain management strategy, based on the sleep biomarkers. The surgical hub may detect potential risk factors or conditions, including systemic inflammation and/or reduced immune function, based on the sleep biomarkers.

Core Body Temperature

A core body temperature sensing system may measure body temperature data including temperature, emitted frequency spectra, and/or the like. The core body temperature sensing system may measure body temperature data using some combination of thermometers and/or radio telemetry. The core body temperature sensing system may include an ingestible thermometer that measures the temperature of the digestive tract. The ingestible thermometer may wirelessly transmit measured temperature data. The core body temperature sensing system may include a wearable antenna that measures body emission spectra. The core body temperature sensing system may include a wearable patch that measures body temperature data.

The core body temperature sensing system may calculate body temperature using the body temperature data. The core body temperature sensing system may transmit the calculated body temperature to a monitoring device. The monitoring device may track the core body temperature data over time and display it to a user.

The core body temperature sensing system may process the core body temperature data locally or send the data to a processing unit and/or a computing system. Based on the measured temperature data, the core body temperature sensing system may detect body temperature-related biomarkers, complications and/or contextual information that may include abnormal temperature, characteristic fluctuations, infection, menstrual cycle, climate, physical activity, and/or sleep.

For example, the core body temperature sensing system may detect abnormal temperature based on temperature being outside the range of 36.5° C. and 37.5° C. For example, the core body temperature sensing system may detect post-operation infection or sepsis based on certain temperature fluctuations and/or when core body temperature reaches abnormal levels. For example, the core body temperature sensing system may detect physical activities using measured fluctuations in core body temperature.

For example, the body temperature sensing system may detect core body temperature data and trigger the sensing system to emit a cooling or heating element to raise or lower the body temperature in line with the measured ambient temperature.

In an example, the body temperature sensing system may send the body temperature-related biomarkers to a computing system, such as a surgical hub. In an example, the body temperature sensing system may send the measured body temperature data to the computing system. The computer system may derive the body temperature-related biomarkers based on the received body temperature data.

Maximal Oxygen Consumption (VO2 Max)

A maximal oxygen consumption (VO2 max) sensing system may measure VO2 max data, including oxygen uptake, heart rate, and/or movement speed. The VO2 max sensing system may measure VO2 max data during physical activities, including running and/or walking. The VO2 max sensing system may include a wearable device. The VO2 max sensing system may process the VO2 max data locally or transmit the data to a processing unit and/or a computing system.

Based on the measured VO2 max data, the sensing system and/or the computing system may derive, detect, and/or calculate biomarkers, including a VO2 max quantifier, VO2 max score, physical activity, and/or physical activity intensity. The VO2 max sensing system may select correct VO2 max data measurements during correct time segments to calculate accurate VO2 max information. Based on the VO2 max information, the sensing system may detect dominating cardio, vascular, and/or respiratory limiting factors. Based on the VO2 max information, risks may be predicted including adverse cardiovascular events in surgery and/or increased risk of in-hospital morbidity. For example, increased risk of in-hospital morbidity may be detected when the calculated VO2 max quantifier falls below a specific threshold, such as 18.2 ml kg-1 min-1.

In an example, the VO2 max sensing system may send the VO2 max-related biomarkers to a computing system, such as a surgical hub. In an example, the VO2 max sensing system may send the measured VO2 max data to the computing system. The computer system may derive the VO2 max-related biomarkers based on the received VO2 max data.

Physical Activity

A physical activity sensing system may measure physical activity data, including heart rate, motion, location, posture, range-of-motion, movement speed, and/or cadence. The physical activity sensing system may measure physical activity data including accelerometer, magnetometer, gyroscope, global positioning system (GPS), PPG, and/or ECG. The physical activity sensing system may include a wearable device. The physical activity wearable device may include, but is not limited to, a watch, wrist band, vest, glove, belt, headband, shoe, and/or garment. The physical activity sensing system may locally process the physical activity data or transmit the data to a processing unit and/or a computing system.

Based on the measured physical activity data, the physical activity sensing system may detect physical activity-related biomarkers, including but not limited to exercise activity, physical activity intensity, physical activity frequency, and/or physical activity duration. The physical activity sensing system may generate physical activity summaries based on physical activity information.

For example, the physical activity sensing system may send physical activity information to a computing system. For example, the physical activity sensing system may send measured data to a computing system. The computing system may, based on the physical activity information, generate activity summaries, training plans, and/or recovery plans. The computing system may store the physical activity information in user profiles. The computing system may display the physical activity information graphically. The computing system may select certain physical activity information and display the information together or separately.

Alcohol Consumption

An alcohol consumption sensing system may measure alcohol consumption data including alcohol and/or sweat. The alcohol consumption sensing system may use a pump to measure perspiration. The pump may use a fuel cell that reacts with ethanol to detect alcohol presence in perspiration. The alcohol consumption sensing system may include a wearable device, for example, a wristband. The alcohol consumption sensing system may use microfluidic applications to measure alcohol and/or sweat. The microfluidic applications may measure alcohol consumption data using sweat stimulation and wicking with commercial ethanol sensors. The alcohol consumption sensing system may include a wearable patch that adheres to skin. The alcohol consumption sensing system may include a breathalyzer. The sensing system may process the alcohol consumption data locally or transmit the data to a processing unit and/or computing system.

Based on the measured alcohol consumption data, the sensing system may calculate a blood alcohol concentration. The sensing system may detect alcohol consumption conditions and/or risk factors. The sensing system may detect alcohol consumption-related biomarkers including reduced immune capacity, cardiac insufficiency, and/or arrhythmia. Reduced immune capacity may occur when a patient consumes three or more alcohol units per day. The sensing system may detect risk factors for postoperative complications including infection, cardiopulmonary complication, and/or bleeding episodes. Healthcare providers may use the detected risk factors for predicting or detecting post-operative or post-surgical complications, for example, to affect decisions and precautions taken during post-surgical care.

In an example, the alcohol consumption sensing system may send the alcohol consumption-related biomarkers to a computing system, such as a surgical hub. In an example, the alcohol consumption sensing system may send the measured alcohol consumption data to the computing system. The computer system may derive the alcohol consumption-related biomarkers based on the received alcohol consumption data.

Respiration Rate

A respiration sensing system may measure respiration rate data, including inhalation, exhalation, chest cavity movement, and/or airflow. The respiration sensing system may measure respiration rate data mechanically and/or acoustically. The respiration sensing system may measure respiration rate data using a ventilator. The respiration sensing system may measure respiration data mechanically by detecting chest cavity movement. Two or more applied electrodes on a chest may measure the changing distance between the electrodes to detect chest cavity expansion and contraction during a breath. The respiration sensing system may include a wearable skin patch. The respiration sensing system may measure respiration data acoustically using a microphone to record airflow sounds. The respiration sensing system may locally process the respiration data or transmit the data to a processing unit and/or computing system.

Based on measured respiration data, the respiration sensing system may generate respiration-related biomarkers including breath frequency, breath pattern, and/or breath depth. Based on the respiratory rate data, the respiration sensing system may generate a respiration quality score.

Based on the respiration rate data, the respiration sensing system may detect respiration-related biomarkers including irregular breathing, pain, air leak, collapsed lung, lung tissue and strength, and/or shock. For example, the respiration sensing system may detect irregularities based on changes in breath frequency, breath pattern, and/or breath depth. For example, the respiration sensing system may detect post-operative pain based on short, sharp breaths. For example, the respiration sensing system may detect an air leak based on a volume difference between inspiration and expiration. For example, the respiration sensing system may detect a collapsed lung based on increased breath frequency combined with a constant volume inhalation. For example, the respiration sensing system may detect lung tissue strength and shock including systemic inflammatory response syndrome (SIRS) based on an increase in respiratory rate, including more than 2 standard deviations. In an example, the detection described herein may be performed by a computing system based on measured data and/or related biomarkers generated by the respiration sensing system.

Oxygen Saturation

An oxygen saturation sensing system may measure oxygen saturation data, including light absorption, light transmission, and/or light reflectance. The oxygen saturation sensing system may use pulse oximetry. For example, the oxygen saturation sensing system may use pulse oximetry by measuring the absorption spectra of deoxygenated and oxygenated hemoglobin. The oxygen saturation sensing system may include one or more light-emitting diodes (LEDs) with predetermined wavelengths. The LEDs may impose light on hemoglobin. The oxygen saturation sensing system may measure the amount of imposed light absorbed by the hemoglobin. The oxygen saturation sensing system may measure the amount of transmitted light and/or reflected light from the imposed light wavelengths. The oxygen saturation sensing system may include a wearable device, including an earpiece and/or a watch. The oxygen saturation sensing system may process the measured oxygen saturation data locally or transmit the data to a processing unit and/or computing system.

Based on the oxygen saturation data, the oxygen saturation sensing system may calculate oxygen saturation-related biomarkers including peripheral blood oxygen saturation (SpO2), hemoglobin oxygen concentration, and/or changes in oxygen saturation rates. For example, the oxygen saturation sensing system may calculate SpO2 using the ratio of measured light absorbances of each imposed light wavelength.

Based on the oxygen saturation data, the oxygen saturation sensing system may predict oxygen saturation-related biomarkers, complications, and/or contextual information including cardiothoracic performance, delirium, collapsed lung, and/or recovery rates. For example, the oxygen saturation sensing system may detect post-operation delirium when the sensing system measures pre-operation SpO2 values below 59.5%. For example, an oxygen saturation sensing system may help monitor post-operation patient recovery. Low SpO2 may reduce the repair capacity of tissues because low oxygen may reduce the amount of energy a cell can produce. For example, the oxygen saturation sensing system may detect a collapsed lung based on low post-operation oxygen saturation. In an example, the detection described herein may be performed by a computing system based on measured data and/or related biomarkers generated by the oxygen saturation sensing system.

Blood Pressure

A blood pressure sensing system may measure blood pressure data including blood vessel diameter, tissue volume, and/or pulse transit time. The blood pressure sensing system may measure blood pressure data using oscillometric measurements, ultrasound patches, photoplethysmography, and/or arterial tonometry. The blood pressure sensing system using photoplethysmography may include a photodetector to sense light scattered by imposed light from an optical emitter. The blood pressure sensing system using arterial tonometry may use arterial wall applanation. The blood pressure sensing system may include an inflatable cuff, wristband, watch and/or ultrasound patch.

Based on the measured blood pressure data, a blood pressure sensing system may quantify blood pressure-related biomarkers including systolic blood pressure, diastolic blood pressure, and/or pulse transit time. The blood pressure sensing system may use the blood pressure-related biomarkers to detect blood pressure-related conditions such as abnormal blood pressure. The blood pressure sensing system may detect abnormal blood pressure when the measured systolic and diastolic blood pressures fall outside the range of 90/60 to 120-90 (systolic/diastolic). For example, the blood pressure sensing system may detect post-operation septic or hypovolemic shock based on measured low blood pressure. For example, the blood pressure sensing system may detect a risk of edema based on detected high blood pressure. The blood pressure sensing system may predict the required seal strength of a harmonic seal based on measured blood pressure data. Higher blood pressure may require a stronger seal to overcome bursting. The blood pressure sensing system may display blood pressure information locally or transmit the data to a system. The sensing system may display blood pressure information graphically over a period of time.

A blood pressure sensing system may process the blood pressure data locally or transmit the data to a processing unit and/or a computing system. In an example, the detection, prediction and/or determination described herein may be performed by a computing system based on measured data and/or related biomarkers generated by the blood pressure sensing system.

Blood Sugar

A blood sugar sensing system may measure blood sugar data including blood glucose level and/or tissue glucose level. The blood sugar sensing system may measure blood sugar data non-invasively. The blood sugar sensing system may use an earlobe clip. The blood sugar sensing system may display the blood sugar data.

Based on the measured blood sugar data, the blood sugar sensing system may infer blood sugar irregularity. Blood sugar irregularity may include blood sugar values falling outside a certain threshold of normally occurring values. A normal blood sugar value may include the range between 70 and 120 mg/dL while fasting. A normal blood sugar value may include the range between 90 and 160 mg/dL while not-fasting.

For example, the blood sugar sensing system may detect a low fasting blood sugar level when blood sugar values fall below 50 mg/dL. For example, the blood sugar sensing system may detect a high fasting blood sugar level when blood sugar values exceed 315 mg/dL. Based on the measured blood sugar levels, the blood sugar sensing system may detect blood sugar-related biomarkers, complications, and/or contextual information including diabetes-associated peripheral arterial disease, stress, agitation, reduced blood flow, risk of infection, and/or reduced recovery times.

The blood sugar sensing system may process blood sugar data locally or transmit the data to a processing unit and/or computing system. In an example, the detection, prediction and/or determination described herein may be performed by a computing system based on measured data and/or related biomarkers generated by the blood sugar sensing system.

Heart Rate Variability

A heart rate variability (HRV) sensing system may measure HRV data including heartbeats and/or duration between consecutive heartbeats. The HRV sensing system may measure HRV data electrically or optically. The HRV sensing system may measure heart rate variability data electrically using ECG traces. The HRV sensing system may use ECG traces to measure the time period variation between R peaks in a QRS complex. An HRV sensing system may measure heart rate variability optically using PPG traces. The HRV sensing system may use PPG traces to measure the time period variation of inter-beat intervals. The HRV sensing system may measure HRV data over a set time interval. The HRV sensing system may include a wearable device, including a ring, watch, wristband, and/or patch.

Based on the HRV data, an HRV sensing system may detect HRV-related biomarkers, complications, and/or contextual information including cardiovascular health, changes in HRV, menstrual cycle, meal monitoring, anxiety levels, and/or physical activity. For example, an HRV sensing system may detect high cardiovascular health based on high HRV. For example, an HRV sensing system may predict pre-operative stress, and use pre-operative stress to predict post-operative pain. For example, an HRV sensing system may indicate post-operative infection or sepsis based on a decrease in HRV.

The HRV sensing system may locally process HRV data or transmit the data to a processing unit and/or a computing system. In an example, the detection, prediction, and/or determination described herein may be performed by a computing system based on measured data and/or related biomarkers generated by the HRV sensing system.

Blood Potential of Hydrogen (pH)

A potential of hydrogen (pH) sensing system may measure pH data including blood pH and/or sweat pH. The pH sensing system may measure pH data invasively and/or non-invasively. The pH sensing system may measure pH data non-invasively using a colorimetric approach and pH sensitive dyes in a microfluidic circuit. In a colorimetric approach, pH sensitive dyes may change color in response to sweat pH. The pH sensing system may measure pH using optical spectroscopy to match color change in pH sensitive dyes to a pH value. The pH sensing system may include a wearable patch. The pH sensing system may measure pH data during physical activity.

Based on the measured pH data, the pH sensing system may detect pH-related biomarkers, including normal blood pH, abnormal blood pH, and/or acidic blood pH. The pH sensing system may detect pH-related biomarkers, complications, and/or contextual information by comparing measured pH data to a standard pH scale. A standard pH scale may identify a healthy pH range to include values between 7.35 and 7.45.

The pH sensing system may use the pH-related biomarkers to indicate pH conditions including post-operative internal bleeding, acidosis, sepsis, lung collapse, and/or hemorrhage. For example, the pH sensing system may predict post-operative internal bleeding based on pre-operation acidic blood pH. Acidic blood may reduce blood clotting capacity by inhibiting thrombin generation. For example, the pH sensing system may predict sepsis and/or hemorrhage based on acidic pH. Lactic acidosis may cause acidic pH. The pH sensing system may continuously monitor blood pH data as acidosis may only occur during exercise.

The pH sensing system may locally process pH data or transmit pH data to a processing unit and/or computing system. In an example, the detection, prediction and/or determination described herein may be performed by a computing system based on measured data and/or related biomarkers generated by the pH sensing system.

Hydration State

A hydration state sensing system may measure hydration data including water light absorption, water light reflection, and/or sweat levels. The hydration state sensing system may use optical spectroscopy or sweat-based colorimetry. The hydration state sensing system may use optical spectroscopy by imposing emitted light onto skin and measuring the reflected light. Optical spectroscopy may measure water content by measuring amplitudes of the reflected light from certain wavelengths, including 1720 nm, 1750 nm, and/or 1770 nm. The hydration state sensing system may include a wearable device that may impose light onto skin. The wearable device may include a watch. The hydration state sensing system may use sweat-based colorimetry to measure sweat levels. Sweat-based colorimetry may be processed in conjunction with user activity data and/or user water intake data.

Based on the hydration data, the hydration state sensing system may detect water content. Based on the water content, a hydration state sensing system may identify hydration-related biomarkers, complications, and/or contextual information including dehydration, risk of kidney injury, reduced blood flow, risk of hypovolemic shock during or after surgery, and/or decreased blood volume.

For example, the hydration state sensing system, based on identified hydration, may detect health risks. Dehydration may negatively impact overall health. For example, the hydration state sensing system may predict risk of post-operation acute kidney injury when it detects reduced blood flow resulting from low hydration levels. For example, the hydration state sensing system may calculate the risk of hypovolemic shock during or after surgery when the sensing system detects dehydration or decreased blood volume. The hydration state sensing system may use the hydration level information to provide context for other received biomarker data, which may include heart rate. The hydration state sensing system may measure hydration state data continuously. Continuous measurement may consider various factors, including exercise, fluid intake, and/or temperature, which may influence the hydration state data.

The hydration state sensing system may locally process hydration data or transmit the data to a processing unit and/or computing system. In an example, the detection, prediction, and/or determination described herein may be performed by a computing system based on measured data and/or related biomarkers generated by the hydration state sensing system.

Heart Rate

A heart rate sensing system may measure heart rate data including heart chamber expansion, heart chamber contraction, and/or reflected light. The heart rate sensing system may use ECG and/or PPG to measure heart rate data. For example, the heart rate sensing system using ECG may include a radio transmitter, receiver, and one or more electrodes. The radio transmitter and receiver may record voltages across electrodes positioned on the skin resulting from expansion and contraction of heart chambers. The heart rate sensing system may calculate heart rate using measured voltage. For example, the heart rate sensing system using PPG may impose green light on skin and record the reflected light in a photodetector. The heart rate sensing system may calculate heart rate using the measured light absorbed by the blood over a period of time. The heart rate sensing system may include a watch, a wearable elastic band, a skin patch, a bracelet, garments, a wrist strap, an earphone, and/or a headband. For example, the heart rate sensing system may include a wearable chest patch. The wearable chest patch may measure heart rate data and other vital signs or critical data including respiratory rate, skin temperature, body posture, fall detection, single-lead ECG, R-R intervals, and step counts. The wearable chest patch may locally process heart rate data or transmit the data to a processing unit. The processing unit may include a display.

Based on the measured heart rate data, the heart rate sensing system may calculate heart rate-related biomarkers including heart rate, heart rate variability, and/or average heart rate. Based on the heart rate data, the heart rate sensing system may detect biomarkers, complications, and/or contextual information including stress, pain, infection, and/or sepsis. The heart rate sensing system may detect heart rate conditions when heart rate exceeds a normal threshold. A normal threshold for heartrate may include the range of 60 to 100 heartbeats per minute. The heart rate sensing system may diagnose post-operation infection, sepsis, or hypovolemic shock based on increased heart rate, including heart rate in excess of 90 beats per minute.

The heart rate sensing system may process heart rate data locally or transmit the data to a processing unit and/or computing system. In an example, the detection, prediction, and/or determination described herein may be performed by a computing system based on measured data and/or related biomarkers generated by the heart rate sensing system. A heart rate sensing system may transmit the heart rate information to a computing system, such as a surgical hub. The computing system may collect and display cardiovascular parameter information including heart rate, respiration, temperature, blood pressure, arrhythmia, and/or atrial fibrillation. Based on the cardiovascular parameter information, the computing system may generate a cardiovascular health score.

Skin Conductance

A skin conductance sensing system may measure skin conductance data including electrical conductivity. The skin conductance sensing system may include one or more electrodes. The skin conductance sensing system may measure electrical conductivity by applying a voltage across the electrodes. The electrodes may include silver or silver chloride. The skin conductance sensing system may be placed on one or more fingers. For example, the skin conductance sensing system may include a wearable device. The wearable device may include one or more sensors. The wearable device may attach to one or more fingers. Skin conductance data may vary based on sweat levels.

The skin conductance sensing system may locally process skin conductance data or transmit the data to a computing system. Based on the skin conductance data, a skin conductance sensing system may calculate skin conductance-related biomarkers including sympathetic activity levels. For example, a skin conductance sensing system may detect high sympathetic activity levels based on high skin conductance.

Peripheral Temperature

A peripheral temperature sensing system may measure peripheral temperature data including extremity temperature. The peripheral temperature sensing system may include a thermistor, thermoelectric effect, or infrared thermometer to measure peripheral temperature data. For example, the peripheral temperature sensing system using a thermistor may measure the resistance of the thermistor. The resistance may vary as a function of temperature. For example, the peripheral temperature sensing system using the thermoelectric effect may measure an output voltage. The output voltage may increase as a function of temperature. For example, the peripheral temperature sensing system using an infrared thermometer may measure the intensity of radiation emitted from a body's blackbody radiation. The intensity of radiation may increase as a function of temperature.

Based on peripheral temperature data, the peripheral temperature sensing system may determine peripheral temperature-related biomarkers including basal body temperature, extremity skin temperature, and/or patterns in peripheral temperature. Based on the peripheral temperature data, the peripheral temperature sensing system may detect conditions including diabetes.

The peripheral temperature sensing system may locally process peripheral temperature data and/or biomarkers or transmit the data to a processing unit. For example, the peripheral temperature sensing system may send peripheral temperature data and/or biomarkers to a computing system, such as a surgical hub. The computing system may analyze the peripheral temperature information with other biomarkers, including core body temperature, sleep, and menstrual cycle. For example, the detection, prediction, and/or determination described herein may be performed by a computing system based on measured data and/or related biomarkers generated by the peripheral temperature sensing system.

Tissue Perfusion Pressure

A tissue perfusion pressure sensing system may measure tissue perfusion pressure data including skin perfusion pressure. The tissue perfusion sensing system may use optical methods to measure tissue perfusion pressure data. For example, the tissue perfusion sensing system may illuminate skin and measure the light transmitted and reflected to detect changes in blood flow. The tissue perfusion sensing system may apply occlusion. For example, the tissue perfusion sensing system may determine skin perfusion pressure based on the measured pressure used to restore blood flow after occlusion. The tissue perfusion sensing system may measure the pressure to restore blood flow after occlusion using a strain gauge or laser doppler flowmetry. The measured change in frequency of light caused by movement of blood may directly correlate with the number and velocity of red blood cells, which the tissue perfusion pressure sensing system may use to calculate pressure. The tissue perfusion pressure sensing system may monitor tissue flaps during surgery to measure tissue perfusion pressure data.

Based on the measured tissue perfusion pressure data, the tissue perfusion pressure sensing system may detect tissue perfusion pressure-related biomarkers, complications, and/or contextual information including hypovolemia, internal bleeding, and/or tissue mechanical properties. For example, the tissue perfusion pressure sensing system may detect hypovolemia and/or internal bleeding based on a drop in perfusion pressure. Based on the measured tissue perfusion pressure data, the tissue perfusion pressure sensing system may inform surgical tool parameters and/or medical procedures. For example, the tissue perfusion pressure sensing system may determine tissue mechanical properties using the tissue perfusion pressure data. Based on the determined mechanical properties, the sensing system may generate stapling procedure and/or stapling tool parameter adjustment(s). Based on the determined mechanical properties, the sensing system may inform dissecting procedures. Based on the measured tissue perfusion pressure data, the tissue perfusion pressure sensing system may generate a score for overall adequacy of perfusion.

The tissue perfusion pressure sensing system may locally process tissue perfusion pressure data or transmit the data to a processing unit and/or computing system. In an example, the detection, prediction, determination, and/or generation described herein may be performed by a computing system based on measured data and/or related biomarkers generated by the tissue perfusion pressure sensing system.

Coughing and Sneezing

A coughing and sneezing sensing system may measure coughing and sneezing data including coughing, sneezing, movement, and sound. The coughing and sneezing sensing system may track hand or body movement that may result from a user covering her mouth while coughing or sneezing. The sensing system may include an accelerometer and/or a microphone. The sensing system may include a wearable device. The wearable device may include a watch.

Based on the coughing and sneezing data, the sensing system may detect coughing and sneezing-related biomarkers, including but not limited to, coughing frequency, sneezing frequency, coughing severity, and/or sneezing severity. The sensing system may establish a coughing and sneezing baseline using the coughing and sneezing information. The coughing and sneezing sensing system may locally process coughing and sneezing data or transmit the data to a computing system.

Based on the coughing and sneezing data, the sensing system may detect coughing and sneezing-related biomarkers, complications, and/or contextual information including respiratory tract infection, infection, collapsed lung, pulmonary edema, gastroesophageal reflux disease, allergic rhinitis, and/or systemic inflammation. For example, the coughing and sneezing sensing system may indicate gastroesophageal reflux disease when the sensing system measures chronic coughing. Chronic coughing may lead to inflammation of the lower esophagus. Lower esophagus inflammation may affect the properties of stomach tissue for sleeve gastrectomy. For example, the coughing and sneezing sensing system may detect allergic rhinitis based on sneezing. Sneezing may link to systemic inflammation. Systemic inflammation may affect the mechanical properties of the lungs and/or other tissues. In an example, the detection, prediction, and/or determination described herein may be performed by a computing system based on measured data and/or related biomarkers generated by the coughing and sneezing sensing system.

Gastrointestinal Motility

A gastrointestinal (GI) motility sensing system may measure GI motility data including pH, temperature, pressure, and/or stomach contractions. The GI motility sensing system may use electrogastrography, electrogastroenterography, stethoscopes, and/or ultrasounds. The GI motility sensing system may include a non-digestible capsule. For example, the ingestible sensing system may adhere to the stomach lining. The ingestible sensing system may measure contractions using a piezoelectric device which generates a voltage when deformed.

Based on the GI data, the sensing system may calculate GI motility-related biomarkers including gastric, small bowel, and/or colonic transit times. Based on the gastrointestinal motility information, the sensing system may detect GI motility-related conditions including ileus. The GI motility sensing system may detect ileus based on a reduction in small bowel motility. The GI motility sensing system may notify healthcare professionals when it detects GI motility conditions. The GI motility sensing system may locally process GI motility data or transmit the data to a processing unit. In an example, the detection, prediction, and/or determination described herein may be performed by a computing system based on measured data and/or related biomarkers generated by the GI motility sensing system.

Gastrointestinal Tract Imaging

A GI tract imaging/sensing system may collect images of a patient's colon. The GI tract imaging/sensing system may include an ingestible wireless camera and a receiver. The GI tract imaging/sensing system may include one or more white LEDs, a battery, radio transmitter, and antenna. The ingestible camera may include a pill. The ingestible camera may travel through the digestive tract and take pictures of the colon. The ingestible camera may take pictures up to 35 frames per second during motion. The ingestible camera may transmit the pictures to a receiver. The receiver may include a wearable device. The GI tract imaging/sensing system may process the images locally or transmit them to a processing unit. Doctors may look at the raw images to make a diagnosis.

Based on the GI tract images, the GI tract imaging sensing system may identify GI tract-related biomarkers including stomach tissue mechanical properties or colonic tissue mechanical properties. Based on the collected images, the GI tract imaging sensing system may detect GI tract-related biomarkers, complications, and/or contextual information including mucosal inflammation, Crohn's disease, anastomotic leak, esophagus inflammation, and/or stomach inflammation. The GI tract imaging/sensing system may replicate a physician diagnosis using image analysis software. The GI tract imaging/sensing system may locally process images or transmit the data to a processing unit. In an example, the detection, prediction, and/or determination described herein may be performed by a computing system based on measured data and/or related biomarkers generated by the GI tract imaging/sensing system.

Respiratory Tract Bacteria

A respiratory tract bacteria sensing system may measure bacteria data including foreign DNA or bacteria. The respiratory tract bacteria sensing system may use a radio frequency identification (RFID) tag and/or electronic nose (e-nose). The sensing system using an RFID tag may include one or more gold electrodes, graphene sensors, and/or layers of peptides. The RFID tag may bind to bacteria. When bacteria bind to the RFID tag, the graphene sensor may detect a change in signal-to-signal presence of bacteria. The RFID tag may include an implant. The implant may adhere to a tooth. The implant may transmit bacteria data. The sensing system may use a portable e-nose to measure bacteria data.

Based on measured bacteria data, the respiratory tract bacteria sensing system may detect bacteria-related biomarkers including bacteria levels. Based on the bacteria data, the respiratory tract bacteria sensing system may generate an oral health score. Based on the detected bacteria data, the respiratory tract bacteria sensing system may identify bacteria-related biomarkers, complications, and/or contextual information, including pneumonia, lung infection, and/or lung inflammation. The respiratory tract bacteria sensing system may locally process bacteria information or transmit the data to a processing unit. In an example, the detection, prediction, and/or determination described herein may be performed by a computing system based on measured data and/or related biomarkers generated by the respiratory tract bacteria sensing system.

Edema

An edema sensing system may measure edema data including lower leg circumference, leg volume, and/or leg water content level. The edema sensing system may include a force sensitive resistor, strain gauge, accelerometer, gyroscope, magnetometer, and/or ultrasound. The edema sensing system may include a wearable device. For example, the edema sensing system may include socks, stockings, and/or ankle bands.

Based on the measured edema data, the edema sensing system may detect edema-related biomarkers, complications, and/or contextual information, including inflammation, rate of change in inflammation, poor healing, infection, leak, colorectal anastomotic leak, and/or water build-up.

For example, the edema sensing system may detect a risk of colorectal anastomotic leak based on fluid build-up. Based on the detected edema physiological conditions, the edema sensing system may generate a score for healing quality. For example, the edema sensing system may generate the healing quality score by comparing edema information to a certain threshold lower leg circumference. Based on the detected edema information, the edema sensing system may generate edema tool parameters including responsiveness to stapler compression. The edema sensing system may provide context for measured edema data by using measurements from the accelerometer, gyroscope, and/or magnetometer. For example, the edema sensing system may detect whether the user is sitting, standing, or lying down.

The edema sensing system may process measured edema data locally or transmit the edema data to a processing unit. In an example, the detection, prediction, and/or determination described herein may be performed by a computing system based on measured data and/or related biomarkers generated by the edema sensing system.

Mental Aspects

A mental aspect sensing system may measure mental aspect data, including heart rate, heart rate variability, brain activity, skin conductance, skin temperature, galvanic skin response, movement, and/or sweat rate. The mental aspect sensing system may measure mental aspect data over a set duration to detect changes in mental aspect data. The mental aspect sensing system may include a wearable device. The wearable device may include a wristband.

Based on the mental aspect data, the sensing system may detect mental aspect-related biomarkers, including emotional patterns, positivity levels, and/or optimism levels. Based on the detected mental aspect information, the mental aspect sensing system may identify mental aspect-related biomarkers, complications, and/or contextual information including cognitive impairment, stress, anxiety, and/or pain. Based on the mental aspect information, the mental aspect sensing system may generate mental aspect scores, including a positivity score, optimism score, confusion or delirium score, mental acuity score, stress score, anxiety score, depression score, and/or pain score.

Mental aspect data, related biomarkers, complications, contextual information, and/or mental aspect scores may be used to determine treatment courses, including pain relief therapies. For example, post-operative pain may be predicted when it detects pre-operative anxiety and/or depression. For example, based on detected positivity and optimism levels, the mental aspect sensing system may determine mood quality and mental state. Based on mood quality and mental state, the mental aspect sensing system may indicate additional care procedures that would benefit a patient, including paint treatments and/or psychological assistance. For example, based on detected cognitive impairment, confusion, and/or mental acuity, the mental aspects sensing system may indicate conditions including delirium, encephalopathy, and/or sepsis. Delirium may be hyperactive or hypoactive. For example, based on detected stress and anxiety, the mental aspect sensing system may indicate conditions including hospital anxiety and/or depression. Based on detected hospital anxiety and/or depression, the mental aspect sensing system may generate a treatment plan, including pain relief therapy and/or pre-operative support.

In an example, the detection, prediction, and/or determination described herein may be performed by a computing system based on measured data and/or related biomarkers generated by the mental aspect sensing system. The mental aspect sensing system may process mental aspect data locally or transmit the data to a processing unit.

Sweat

A sweat sensing system may measure sweat data including sweat, sweat rate, cortisol, adrenaline, and/or lactate. The sweat sensing system may measure sweat data using microfluidic capture, saliva testing, nanoporous electrode systems, e-noses, reverse iontophoresis, blood tests, amperometric thin film biosensors, textile organic electrochemical transistor devices, and/or electrochemical biosensors. The sensing system may measure sweat data with microfluidic capture using a colorimetric or impedimetric method. The microfluidic capture may include a flexible patch placed in contact with skin. The sweat sensing system may measure cortisol using saliva tests. The saliva tests may use electrochemical methods and/or molecularly selective organic electrochemical transistor devices. The sweat sensing system may measure ion build-up that bind to cortisol in sweat to calculate cortisol levels. The sweat sensing system may use enzyme reactions to measure lactate. Lactate may be measured using lactate oxidase and/or lactate dehydrogenase methods.

Based on the measured sweat data, the sweat sensing system or processing unit may detect sweat-related biomarkers, complications, and/or contextual information including cortisol levels, adrenaline levels, and/or lactate levels. Based on the detected sweat data and/or related biomarkers, the sweat sensing system may indicate sweat physiological conditions including sympathetic nervous system activity, psychological stress, cellular immunity, circadian rhythm, blood pressure, tissue oxygenation, and/or post-operation pain. For example, based on sweat rate data, the sweat sensing system may detect psychological stress. Based on the detected psychological stress, the sweat sensing system may indicate heightened sympathetic activity. Heightened sympathetic activity may indicate post-operation pain.

Based on the detected sweat information, the sweat sensing system may detect sweat-related biomarkers, complications, and/or contextual information including post-operation infection, metastasis, chronic elevation, ventricular failure, sepsis, hemorrhage, hyperlactemia, and/or septic shock. For example, the sensing system may detect septic shock when serum lactate concentration exceeds a certain level, such as 2 mmol/L. For example, based on detected patterns of adrenaline surges, the sweat sensing system may indicate a risk of heart attack and/or stroke. For example, surgical tool parameter adjustments may be determined based on detected adrenaline levels. The surgical tool parameter adjustments may include settings for surgical sealing tools. For example, the sweat sensing system may predict infection risk and/or metastasis based on detected cortisol levels. The sweat sensing system may notify healthcare professionals about the condition.

In an example, the detection, prediction, and/or determination described herein may be performed by a computing system based on measured data and/or related biomarkers generated by the sweat sensing system. The sweat sensing system may locally process sweat data or transmit the sweat data to a processing unit.

Circulating Tumor Cells

A circulating tumor cell sensing system may detect circulating tumor cells. The circulating tumor cell sensing system may detect circulating tumor cells using an imaging agent. The imaging agent may use microbubbles attached with antibodies which target circulating tumor cells. The imaging agent may be injected into the bloodstream. The imaging agent may attach to circulating tumor cells. The circulating tumor cell sensing system may include an ultrasonic transmitter and receiver. The ultrasonic transmitter and receiver may detect the imaging agent attached to circulating tumor cells. The circulating tumor cell sensing system may receive circulating tumor cell data.

Based on the detected circulating tumor cells data, the circulating tumor cell sensing system may calculate metastatic risk. The presence of circulating cancerous cells may indicate metastatic risk. Circulating cancerous cells per milliliter of blood exceeding a threshold amount may indicate a metastatic risk. Cancerous cells may circulate the bloodstream when tumors metastasize. Based on the calculated metastatic risk, the circulating tumor cell sensing system may generate a surgical risk score. Based on the generated surgical risk score, the circulating tumor cell sensing system may indicate surgery viability and/or suggested surgical precautions.

In an example, the detection, prediction and/or determination described herein may be performed by a computing system based on measured data and/or related biomarkers generated by the circulating tumor cells sensing system. The circulating tumor cell sensing system may process the circulating tumor cell data locally or transmit the circulating tumor cells data to a processing unit.

Autonomic Tone

An autonomic tone sensing system may measure autonomic tone data including skin conductance, heart rate variability, activity, and/or peripheral body temperature. The autonomic tone sensing system may include one or more electrodes, PPG trace, ECG trace, accelerometer, GPS, and/or thermometer. The autonomic tone sensing system may include a wearable device that may include a wristband and/or finger band.

Based on the autonomic tone data, the autonomic tone sensing system may detect autonomic tone-related biomarkers, complications, and/or contextual information, including sympathetic nervous system activity level and/or parasympathetic nervous system activity level. The autonomic tone may describe the basal balance between the sympathetic and parasympathetic nervous system. Based on the measured autonomic tone data, the autonomic tone sensing system may indicate risk for post-operative conditions including inflammation and/or infection. High sympathetic activity may associate with increase in inflammatory mediators, suppressed immune function, postoperative ileus, increased heart rate, increased skin conductance, increased sweat rate, and/or anxiety.

In an example, the detection, prediction, and/or determination described herein may be performed by a computing system based on measured data and/or related biomarkers generated by the autonomic tone sensing system. The autonomic tone sensing system may process the autonomic tone data locally or transmit the data to a processing unit.

Circadian Rhythm

A circadian rhythm sensing system may measure circadian rhythm data including light exposure, heart rate, core body temperature, cortisol levels, activity, and/or sleep. Based on the circadian rhythm data the circadian rhythm sensing system may detect circadian rhythm-related biomarkers, complications, and/or contextual information including sleep cycle, wake cycle, circadian patterns, disruption in circadian rhythm, and/or hormonal activity.

For example, based on the measured circadian rhythm data, the circadian rhythm sensing system may calculate the start and end of the circadian cycle. The circadian rhythm sensing system may indicate the beginning of the circadian day based on measured cortisol. Cortisol levels may peak at the start of a circadian day. The circadian rhythm sensing system may indicate the end of the circadian day based on measured heart rate and/or core body temperature. Heart rate and/or core body temperature may drop at the end of a circadian day. Based on the circadian rhythm-related biomarkers, the sensing system or processing unit may detect conditions including risk of infection and/or pain. For example, disrupted circadian rhythm may indicate pain and discomfort.

In an example, the detection, prediction, and/or determination described herein may be performed by a computing system based on measured data and/or related biomarkers generated by the circadian rhythm sensing system. The circadian rhythm sensing system may process the circadian rhythm data locally or transmit the data to a processing unit.

Menstrual Cycle

A menstrual cycle sensing system may measure menstrual cycle data including heart rate, heart rate variability, respiration rate, body temperature, and/or skin perfusion. Based on the menstrual cycle data, the menstrual cycle unit may indicate menstrual cycle-related biomarkers, complications, and/or contextual information, including menstrual cycle phase. For example, the menstrual cycle sensing system may detect the periovulatory phase in the menstrual cycle based on measured heart rate variability. Changes in heart rate variability may indicate the periovulatory phase. For example, the menstrual cycle sensing system may detect the luteal phase in the menstrual cycle based on measured wrist skin temperature and/or skin perfusion. Increased wrist skin temperature may indicate the luteal phase. Changes in skin perfusion may indicate the luteal phase. For example, the menstrual cycle sensing system may detect the ovulatory phase based on measured respiration rate. Low respiration rate may indicate the ovulatory phase.

Based on menstrual cycle-related biomarkers, the menstrual cycle sensing system may determine conditions including hormonal changes, surgical bleeding, scarring, bleeding risk, and/or sensitivity levels. For example, the menstrual cycle phase may affect surgical bleeding in rhinoplasty. For example, the menstrual cycle phase may affect healing and scarring in breast surgery. For example, bleeding risk may decrease during the periovulatory phase in the menstrual cycle.

In an example, the detection, prediction, and/or determination described herein may be performed by a computing system based on measured data and/or related biomarkers generated by the menstrual cycle sensing system. The menstrual cycle sensing system may locally process menstrual cycle data or transmit the data to a processing unit.

Environmental Aspects

An environmental sensing system may measure environmental data including environmental temperature, humidity, mycotoxin spore count, and airborne chemical data. The environmental sensing system may include a digital thermometer, air sampling, and/or chemical sensors. The sensing system may include a wearable device. The environmental sensing system may use a digital thermometer to measure environmental temperature and/or humidity. The digital thermometer may include a metal strip with a determined resistance. The resistance of the metal strip may vary with environmental temperature. The digital thermometer may apply the varied resistance to a calibration curve to determine temperature. The digital thermometer may include a wet bulb and a dry bulb. The wet bulb and dry bulb may determine a difference in temperature, which then may be used to calculate humidity.

The environmental sensing system may use air sampling to measure mycotoxin spore count. The environmental sensing system may include a sampling plate with adhesive media connected to a pump. The pump may draw air over the plate over set time at a specific flow rate. The set time may last up to 10 minutes. The environmental sensing system may analyze the sample using a microscope to count the number of spores. The environmental sensing system may use different air sampling techniques including high-performance liquid chromatography (HPLC), liquid chromatography-tandem mass spectrometry (LC-MS/MS), and/or immunoassays and nanobodies.

The environmental sensing system may include chemical sensors to measure airborne chemical data. Airborne chemical data may include different identified airborne chemicals, including nicotine and/or formaldehyde. The chemical sensors may include an active layer and a transducer layer. The active layer may allow chemicals to diffuse into a matrix and alter some physical or chemical property. The changing physical property may include refractive index and/or H-bond formation. The transducer layer may convert the physical and/or chemical variation into a measurable signal, including an optical or electrical signal. The environmental sensing system may include a handheld instrument. The handheld instrument may detect and identify complex chemical mixtures that constitute aromas, odors, fragrances, formulations, spills, and/or leaks. The handheld instrument may include an array of nanocomposite sensors. The handheld instrument may detect and identify substances based on chemical profile.

Based on the environmental data, the sensing system may determine environmental information including climate, mycotoxin spore count, mycotoxin identification, airborne chemical identification, airborne chemical levels, and/or inflammatory chemical inhalation. For example, the environmental sensing system may approximate the mycotoxin spore count in the air based on the measured spore count from a collected sample. The sensing system may identify the mycotoxin spores which may include molds, pollens, insect parts, skin cell fragments, fibers, and/or inorganic particulate. For example, the sensing system may detect inflammatory chemical inhalation, including cigarette smoke. The sensing system may detect second-hand or third-hand smoke.

Based on the environmental information, the sensing system may generate environmental aspects conditions including inflammation, reduced lung function, airway hyper-reactivity, fibrosis, and/or reduce immune functions. For example, the environmental aspects sensing system may detect inflammation and fibrosis based on the measured environmental aspects information. The sensing system may generate instructions for a surgical tool, including a staple and sealing tool used in lung segmentectomy, based on the inflammation and/or fibrosis. Inflammation and fibrosis may affect the surgical tool usage. For example, cigarette smoke may cause higher pain scores in various surgeries.

The environmental sensing system may generate an air quality score based on the measured mycotoxins and/or airborne chemicals. For example, the environmental sensing system may notify about hazardous air quality if it detects a poor air quality score. The environmental sensing system may send a notification when the generated air quality score falls below a certain threshold. The threshold may include exposure exceeding 105 spores of mycotoxins per cubic meter. The environmental sensing system may display a readout of the environment condition exposure over time.

The environmental sensing system may locally process environmental data or transmit the data to a processing unit. In an example, the detection, prediction, and/or determination described herein may be performed by a computing system based on measured data generated by the environmental sensing system.

Light Exposure

A light exposure sensing system may measure light exposure data. The light exposure sensing system may include one or more photodiode light sensors. For example, the light exposure sensing system using photodiode light sensors may include a semiconductor device in which the device current may vary as a function of light intensity. Incident photons may create electron-hole pairs that flow across the semiconductor junction, which may create current. The rate of electron-hole pair generation may increase as a function of the intensity of the incident light. The light exposure sensing system may include one or more photoresistor light sensors. For example, the light exposure sensing system using photoresistor light sensors may include a light-dependent resistor in which the resistance decreases as a function of light intensity. The photoresistor light sensor may include passive devices without a PN-junction. The photoresistor light sensors may be less sensitive than photodiode light sensors. The light exposure sensing system may include a wearable, including a necklace and/or clip-on button.

Based on the measured light exposure data, the light exposure sensing system may detect light exposure information including exposure duration, exposure intensity, and/or light type. For example, the sensing system may determine whether light exposure consists of natural light or artificial light. Based on the detected light exposure information, the light exposure sensing system may detect light exposure-related biomarker(s) including circadian rhythm. Light exposure may entrain the circadian cycle.

The light exposure sensing system may locally process the light exposure data or transmit the data to a processing unit. In an example, the detection, prediction, and/or determination described herein may be performed by a computing system based on measured data and/or related biomarkers generated by the light exposure sensing system.

The various sensing systems described herein may measure data, derive related biomarkers, and send the biomarkers to a computing system, such as a surgical hub as described herein with reference to FIGS. 1-12. The various sensing systems described herein may send the measured data to the computing system. The computing system may derive the related biomarkers based on the received measurement data.

The biomarker sensing systems may include a wearable device. In an example, the biomarker sensing system may include eyeglasses. The eyeglasses may include a nose pad sensor. The eyeglasses may measure biomarkers, including lactate, glucose, and/or the like. In an example, the biomarker sensing system may include a mouthguard. The mouthguard may include a sensor to measure biomarkers including uric acid and/or the like. In an example, the biomarker sensing system may include a contact lens. The contact lens may include a sensor to measure biomarkers including glucose and/or the like. In an example, the biomarker sensing system may include a tooth sensor. The tooth sensor may be graphene-based. The tooth sensor may measure biomarkers including bacteria and/or the like. In an example, the biomarker sensing system may include a patch. The patch may be wearable on the chest skin or arm skin. For example, the patch may include a chem-phys hybrid sensor. The chem-phys hybrid sensor may measure biomarkers including lactate, ECG, and/or the like. For example, the patch may include nanomaterials. The nanomaterials patch may measure biomarkers including glucose and/or the like. For example, the patch may include an iontophoretic biosensor. The iontophoretic biosensor may measure biomarkers including glucose and/or the like. In an example, the biomarker sensing system may include a microfluidic sensor. The microfluidic sensor may measure biomarkers including lactate, glucose, and/or the like. In an example, the biomarker sensing system may include an integrated sensor array. The integrated sensory array may include a wearable wristband. The integrated sensory array may measure biomarkers including lactate, glucose, and/or the like. In an example, the biomarker sensing system may include a wearable diagnostics device. The wearable diagnostic device may measure biomarkers including cortisol, interleukin-6, and/or the like. In an example, the biomarker sensing system may include a self-powered textile-based biosensor. The self-powered textile-based biosensor may include a sock. The self-powered textile-based biosensor may measure biomarkers including lactate and/or the like.

Measurable Biomarkers and Their interrelationship to Physiologic Systems

The various biomarkers described herein may be related to various physiologic systems, including behavior and psychology, cardiovascular system, renal system, skin system, nervous system, GI system, respiratory system, endocrine system, immune system, tumor, musculoskeletal system, and/or reproductive system.

Behavior and Psychology

Behavior and psychology may include social interactions, diet, sleep, activity, and/or psychological status. Behavior and psychology-related biomarkers, complications, contextual information, and/or conditions may be determined and/or predicted based on analyzed biomarker sensing systems data. A computing system, as described herein, may select one or more biomarkers (e.g., data from biomarker sensing systems) from behavior and psychology-related biomarkers, including sleep, circadian rhythm, physical activity, and/or mental aspects for analysis. Behavior and psychology scores may be generated based on the analyzed biomarkers, complications, contextual information, and/or conditions. Behavior and psychology scores may include scores for social interaction, diet, sleep, activity, and/or psychological status.

For example, based on the selected biomarker sensing systems data, sleep-related biomarkers, complications, and/or contextual information may be determined, including sleep quality, sleep duration, sleep timing, immune function, and/or post-operation pain. Based on the selected biomarker sensing systems data, sleep-related conditions may be predicted, including inflammation. In an example, inflammation may be predicted based on analyzed pre-operation sleep. Elevated inflammation may be determined and/or predicted based on disrupted pre-operation sleep. In an example, immune function may be determined based on analyzed pre-operation sleep. Reduced immune function may be predicted based on disrupted pre-operation sleep. In an example, post-operation pain may be determined based on analyzed sleep. Post-operation pain may be determined and/or predicted based on disrupted sleep. In an example, pain and discomfort may be determined based on analyzed circadian rhythm. A compromised immune system may be determined based on analyzed circadian rhythm cycle disruptions.

For example, based on the selected biomarker sensing systems data, activity-related biomarkers, complications, and/or contextual information may be determined, including activity duration, activity intensity, activity type, activity pattern, recovery time, mental health, physical recovery, immune function, and/or inflammatory function. Based on the selected biomarker sensing systems data, activity-related conditions may be predicted. In an example, improved physiology may be determined based on analyzed activity intensity. Moderate intensity exercise may indicate shorter hospital stays, better mental health, better physical recovery, improved immune function, and/or improved inflammatory function. Physical activity type may include aerobic activity and/or non-aerobic activity. Aerobic physical activity may be determined based on analyzed physical activity, including running, cycling, and/or weight training. Non-aerobic physical activity may be determined based on analyzed physical activity, including walking and/or stretching.

For example, based on the selected biomarker sensing systems data, psychological status-related biomarkers, complications, and/or contextual information may be determined, including stress, anxiety, pain, positive emotions, abnormal states, and/or post-operative pain. Based on the selected biomarker sensing systems data, psychological status-related conditions may be predicted, including physical symptoms of disease. Higher post-operative pain may be determined and/or predicted based on analyzed high levels of pre-operative stress, anxiety, and/or pain. Physical symptoms of disease may be predicted based on determined high optimism.

The detection, prediction, determination, and/or generation described herein may be performed by a computing system described herein, such as a surgical hub, a computing device, and/or a smart device based on measured data and/or related biomarkers generated by the biomarker sensing systems.

Cardiovascular System

The cardiovascular system may include the lymphatic system, blood vessels, blood, and/or heart. Cardiovascular system-related biomarkers, complications, contextual information, and/or conditions may be determined and/or predicted based on analyzed biomarker sensing systems data. Systemic circulation conditions may include conditions for the lymphatic system, blood vessels, and/or blood. A computing system may select one or more biomarkers (e.g., data from biomarker sensing systems) from cardiovascular system-related biomarkers, including blood pressure, VO2 max, hydration state, oxygen saturation, blood pH, sweat, core body temperature, peripheral temperature, edema, heart rate, and/or heart rate variability for analysis.

Lymphatic System

For example, based on the selected biomarker sensing systems data, lymphatic system-related biomarkers, complications, and/or contextual information may be determined, including swelling, lymph composition, and/or collagen deposition. Based on the selected biomarker sensing systems data, lymphatic system-related conditions may be predicted, including fibrosis, inflammation, and/or post-operation infection. Inflammation may be predicted based on determined swelling. Post-operation infection may be predicted based on determined swelling. Collagen deposition may be determined based on predicted fibrosis. Increased collagen deposition may be predicted based on fibrosis. Harmonic tool parameter adjustments may be generated based on determined collagen deposition increases. Inflammatory conditions may be predicted based on analyzed lymph composition. Different inflammatory conditions may be determined and/or predicted based on changes in lymph peptidome composition. Metastatic cell spread may be predicted based on predicted inflammatory conditions. Harmonic tool parameter adjustments and margin decisions may be generated based on predicted inflammatory conditions.

Blood Vessels

For example, based on the selected biomarker sensing systems data, blood vessel-related biomarkers, complications, and/or contextual information may be determined, including permeability, vasomotion, pressure, structure, healing ability, harmonic sealing performance, and/or cardiothoracic health fitness. Surgical tool usage recommendations and/or parameter adjustments may be generated based on the determined blood vessel-related biomarkers. Based on the selected biomarker sensing systems data, blood vessel-related conditions may be predicted, including infection, anastomotic leak, septic shock and/or hypovolemic shock. In an example, increased vascular permeability may be determined based on analyzed edema, bradykinin, histamine, and/or endothelial adhesion molecules. Endothelial adhesion molecules may be measured using cell samples to measure transmembrane proteins. In an example, vasomotion may be determined based on selected biomarker sensing systems data. Vasomotion may include vasodilators and/or vasoconstrictors. In an example, shock may be predicted based on the determined blood pressure-related biomarkers, including vessel information and/or vessel distribution. Individual vessel structure may include arterial stiffness, collagen content, and/or vessel diameter. Cardiothoracic health fitness may be determined based on VO2 max. Higher risk of complications may be determined and/or predicted based on poor VO2 max.

Blood

For example, based on the selected biomarker sensing systems data, blood-related biomarkers, complications, and/or contextual information may be determined, including volume, oxygen, pH, waste products, temperature, hormones, proteins, and/or nutrients. Based on the selected biomarker sensing systems data, blood-related complications and/or contextual information may be determined, including cardiothoracic health fitness, lung function, recovery capacity, anaerobic threshold, oxygen intake, carbon dioxide (CO2) production, fitness, tissue oxygenation, colloid osmotic pressure, and/or blood clotting ability. Based on derived blood-related biomarkers, blood-related conditions may be predicted, including post-operative acute kidney injury, hypovolemic shock, acidosis, sepsis, lung collapse, hemorrhage, bleeding risk, infection, and/or anastomotic leak.

For example, post-operative acute kidney injury and/or hypovolemic shock may be predicted based on the hydration state. For example, lung function, lung recovery capacity, cardiothoracic health fitness, anaerobic threshold, oxygen uptake, and/or CO2 product may be predicted based on the blood-related biomarkers, including red blood cell count and/or oxygen saturation. For example, cardiovascular complications may be predicted based on the blood-related biomarkers, including red blood cell count and/or oxygen saturation. For example, acidosis may be predicted based on the pH. Based on acidosis, blood-related conditions may be indicated, including sepsis, lung collapse, hemorrhage, and/or increased bleeding risk. For example, based on sweat, blood-related biomarkers may be derived, including tissue oxygenation. Insufficient tissue oxygenation may be predicted based on high lactate concentration. Based on insufficient tissue oxygenation, blood-related conditions may be predicted, including hypovolemic shock, septic shock, and/or left ventricular failure. For example, based on the temperature, blood temperature-related biomarkers may be derived, including menstrual cycle and/or basal temperature. Based on the blood temperature-related biomarkers, blood temperature-related conditions may be predicted, including sepsis and/or infection. For example, based on proteins, including albumin content, colloid osmotic pressure may be determined. Based on the colloid osmotic pressure, blood protein-related conditions may be predicted, including edema risk and/or anastomotic leak. Increased edema risk and/or anastomotic leak may be predicted based on low colloid osmotic pressure. Bleeding risk may be predicted based on blood clotting ability. Blood clotting ability may be determined based on fibrinogen content. Reduced blood clotting ability may be determined based on low fibrinogen content.

Heart

For example, based on the selected biomarker sensing systems data, the computing system may derive heart-related biomarkers, complications, and/or contextual information, including heart activity, heart anatomy, recovery rates, cardiothoracic health fitness, and/or risk of complications. Heart activity biomarkers may include electrical activity and/or stroke volume. Recovery rate may be determined based on heart rate biomarkers. Reduced blood supply to the body may be determined and/or predicted based on irregular heart rate. Slower recovery may be determined and/or predicted based on reduced blood supply to the body. Cardiothoracic health fitness may be determined based on analyzed VO2 max values. VO2 max values below a certain threshold may indicate poor cardiothoracic health fitness. VO2 max values below a certain threshold may indicate a higher risk of heart-related complications.

The detection, prediction, determination, and/or generation described herein may be performed by a computing system described herein, such as a surgical hub, a computing device, and/or a smart device, based on measured data and/or related biomarkers generated by the biomarker sensing systems.

Renal System

Renal system-related biomarkers, complications, contextual information, and/or conditions may be determined and/or predicted based on analyzed biomarker sensing systems data. A computing system, as described herein, may select one or more biomarkers (e.g., data from biomarker sensing systems) from renal system-related biomarkers for analysis. Based on the selected biomarker sensing systems data, renal system-related biomarkers, complications, and/or contextual information may be determined including ureter, urethra, bladder, kidney, general urinary tract, and/or ureter fragility. Based on the selected biomarker sensing systems data, renal system-related conditions may be predicted, including acute kidney injury, infection, and/or kidney stones. In an example, ureter fragility may be determined based on urine inflammatory parameters. In an example, acute kidney injury may be predicted based on analyzed Kidney Injury Molecule-1 (KIM-1) in urine.

The detection, prediction, determination, and/or generation described herein may be performed by a computing system described herein, such as a surgical hub, a computing device, and/or a smart device based on measured data and/or related biomarkers generated by the biomarker sensing systems.

Skin System

The skin system may include biomarkers relating to microbiome, skin, nails, hair, sweat, and/or sebum. Skin-related biomarkers may include epidermis biomarkers and/or dermis biomarkers. Sweat-related biomarkers may include activity biomarkers and/or composition biomarkers. Skin system-related biomarkers, complications, contextual information, and/or conditions may be determined and/or predicted based on analyzed biomarker sensing systems data. A computing system, as described herein, may select one or more biomarkers (e.g., data from biomarker sensing systems) from skin-related biomarkers, including skin conductance, skin perfusion pressure, sweat, autonomic tone, and/or pH for analysis.

Skin

For example, based on selected biomarker sensing systems data, skin-related biomarkers, complications, and/or contextual information may be determined, including color, lesions, trans-epidermal water loss, sympathetic nervous system activity, elasticity, tissue perfusion, and/or mechanical properties. Stress may be predicted based on determined skin conductance. Skin conductance may act as a proxy for sympathetic nervous system activity. Sympathetic nervous system activity may correlate with stress. Tissue mechanical properties may be determined based on skin perfusion pressure. Skin perfusion pressure may indicate deep tissue perfusion. Deep tissue perfusion may determine tissue mechanical properties. Surgical tool parameter adjustments may be generated based on determined tissue mechanical properties.

Based on selected biomarker sensing systems data, skin-related conditions may be predicted.

Sweat

For example, based on selected biomarker sensing systems data, sweat-related biomarkers, complications, and/or contextual information may be determined, including activity, composition, autonomic tone, stress response, inflammatory response, blood pH, blood vessel health, immune function, circadian rhythm, and/or blood lactate concentration. Based on selected biomarker sensing systems data, sweat-related conditions may be predicted, including ileus, cystic fibrosis, diabetes, metastasis, cardiac issues, and/or infections.

For example, sweat composition-related biomarkers may be determined based on selected biomarker data. Sweat composition biomarkers may include proteins, electrolytes, and/or small molecules. Based on the sweat composition biomarkers, skin system complications, conditions, and/or contextual information may be predicted, including ileus, cystic fibrosis, acidosis, sepsis, lung collapse, hemorrhage, bleeding risk, diabetes, metastasis, and/or infection. For example, based on protein biomarkers, including sweat neuropeptide Y and/or sweat antimicrobials, stress response may be predicted. Higher sweat neuropeptide Y levels may indicate greater stress response. Cystic fibrosis and/or acidosis may be predicted based on electrolyte biomarkers, including chloride ions, pH, and other electrolytes. High lactate concentrations may be determined based on blood pH. Acidosis may be predicted based on high lactate concentrations. Sepsis, lung collapse, hemorrhage, and/or bleeding risk may be predicted based on predicted acidosis. Diabetes, metastasis, and/or infection may be predicted based on small molecule biomarkers. Small molecule biomarkers may include blood sugar and/or hormones. Hormone biomarkers may include adrenaline and/or cortisol. Based on predicted metastasis, blood vessel health may be determined. Infection due to lower immune function may be predicted based on detected cortisol. Lower immune function may be determined and/or predicted based on high cortisol. For example, sweat-related conditions, including stress response, inflammatory response, and/or ileus, may be predicted based on determined autonomic tone. Greater stress response, greater inflammatory response, and/or ileus may be determined and/or predicted based on high sympathetic tone.

The detection, prediction, determination, and/or generation described herein may be performed by a computing system described herein, such as a surgical hub, a computing device, and/or a smart device based on measured data and/or related biomarkers generated by the biomarker sensing systems.

Nervous System

Nervous system-related biomarkers, complications, contextual information, and/or conditions may be determined and/or predicted based on analyzed biomarker sensing systems data. A computing system, as described herein, may select one or more biomarkers (e.g., data from biomarker sensing systems) from nervous system-related biomarkers, including circadian rhythm, oxygen saturation, autonomic tone, sleep, activity, and/or mental aspects for. The nervous system may include the central nervous system (CNS) and/or the peripheral nervous system. The CNS may include brain and/or spinal cord. The peripheral nervous system may include the autonomic nervous system, motor system, enteric system, and/or sensory system.

For example, based on the selected biomarker sensing systems data, CNS-related biomarkers, complications, and/or contextual information may be determined, including post-operative pain, immune function, mental health, and/or recovery rate. Based on the selected biomarker sensing systems data, CNS-related conditions may be predicted, including inflammation, delirium, sepsis, hyperactivity, hypoactivity, and/or physical symptoms of disease. In an example, a compromised immune system and/or high pain score may be predicted based on disrupted sleep. In an example, post-operation delirium may be predicted based on oxygen saturation. Cerebral oxygenation may indicate post-operation delirium.

For example, based on the selected biomarker sensing systems data, peripheral nervous system-related biomarkers, complications, and/or contextual information may be determined. Based on the selected biomarker sensing systems data, peripheral nervous system-related conditions may be predicted, including inflammation and/or ileus. In an example, high sympathetic tone may be predicted based on autonomic tone. Greater stress response may be predicted based on high sympathetic tone. Inflammation and/or ileus may be predicted based on high sympathetic tone.

The detection, prediction, determination, and/or generation described herein may be performed by a computing system described herein, such as a surgical hub, a computing device, and/or a smart device based on measured data and/or related biomarkers generated by the biomarker sensing systems.

Gastrointestinal System

The GI system may include the upper GI tract, lower GI tract, ancillary organs, peritoneal space, nutritional states, and microbiomes. The upper GI may include the mouth, esophagus, and/or stomach. The lower GI may include the small intestine, colon, and/or rectum. Ancillary organs may include pancreas, liver, spleen, and/or gallbladder. Peritoneal space may include mesentry and/or adipose blood vessels. Nutritional states may include short-term, long-term, and/or systemic. GI-related biomarkers, complications, contextual information, and/or conditions may be determined and/or predicted based on analyzed biomarker sensing systems data. A computing system, as described herein, may select one or more biomarkers (e.g., data from biomarker sensing systems) from GI-related biomarkers, including coughing and sneezing, respiratory bacteria, GI tract imaging/sensing, GI motility, pH, tissue perfusion pressure, environmental, and/or alcohol consumption for analysis. Upper GI The upper GI may include the mouth, esophagus, and/or stomach. For example, based on the selected biomarker sensing systems data, mouth and esophagus-related biomarkers, complications, and/or contextual information, may be determined, including stomach tissue properties, esophageal motility, colonic tissue change, bacteria presence, tumor size, tumor location, and/or tumor tension. Based on the selected biomarker sensing systems data, mouth and esophagus-related conditions may be predicted, including inflammation, surgical site infection (SSI), and/or gastro-esophageal disease. The mouth and esophagus may include mucosa, muscularis, lumen, and/or mechanical properties. Lumen biomarkers may include lumen contents, lumen microbial flora, and/or lumen size. In an example, inflammation may be predicted based on analyzed coughing biomarkers. Gastro-esophageal reflux disease may be predicted based on inflammation. Stomach tissue properties may be predicted based on gastro-esophageal disease. In an example, esophageal motility may be determined based on collagen content and/or muscularis function. In an example, changes to colonic tissue may be indicated based on salivary cytokines. Inflammatory bowel disease (IBD) may be predicted based on changes to colonic tissue. Salivary cytokines may increase in IBD. SSI may be predicted based on analyzed bacteria. Based on the analyzed bacteria, the bacteria may be identified. Respiratory pathogens in the mouth may indicate likelihood of SSI. Based on lumen size and/or location, surgical tool parameter adjustments may be generated. Surgical tool parameter adjustments may include staple sizing, surgical tool fixation, and/or surgical tool approach. In an example, based on mechanical properties, including elasticity, a surgical tool parameter adjustment to use adjunct material may be generated to minimize tissue tension. Additional mobilization parameter adjustments may be generated to minimize tissue tension based on analyzed mechanical properties.

For example, based on the selected biomarker sensing systems data, stomach-related biomarkers, complications, and/or contextual information, may be determined including tissue strength, tissue thickness, recovery rate, lumen location, lumen shape, pancreas function, stomach food presence, stomach water content, stomach tissue thickness, stomach tissue shear strength, and/or stomach tissue elasticity. Based on the selected biomarker sensing systems data, stomach-related conditions may be predicted, including ulcer, inflammation, and/or gastro-esophageal reflux disease. The stomach may include mucosa, muscularis, serosa, lumen, and mechanical properties. Stomach-related conditions, including ulcers, inflammation, and/or gastro-esophageal disease may be predicted based on analyzed coughing and/or GI tract imaging. Stomach tissue properties may be determined based on gastro-esophageal reflux disease. Ulcers may be predicted based on analyzed *H. pylori*. Stomach tissue mechanical properties may be determined based on GI tract images. Surgical tool parameter adjustments may be generated based on the determined stomach tissue mechanical properties. Risk of post-operative leak may be predicted based on determined stomach tissue mechanical properties. In an example, key components for tissue strength and/or thickness may be determined based on analyzed collagen content. Key components of tissue strength and thickness may affect recovery. In an example, blood supply and/or blood location may be determined based on serosa biomarkers. In an example, biomarkers, including pouch size, pouch volume, pouch location, pancreas function, and/or food presence may be determined based on analyzed lumen biomarkers. Lumen biomarkers may include lumen location, lumen shape, gastric emptying speed, and/or lumen contents. Pouch size may be determined based on start and end locations of the pouch. Gastric emptying speed may be determined based on GI motility. Pancreas function may be determined based on gastric emptying speed. Lumen content may be determined based on analyzed gastric pH. Lumen content may include stomach food presence. For example, solid food presence may be determined based on gastric pH variation. Low gastric pH may be predicted based on an empty stomach. Basic gastric pH may be determined based on eating. Buffering by food may lead to basic gastric pH. Gastric pH may increase based on stomach acid secretion. Gastric pH may return to low value when the buffering capacity of food is exceeded. Intraluminal pH sensors may detect eating. For example, stomach water content, tissue thickness, tissue shear strength, and/or tissue elasticity may be determined based on tissue perfusion pressure. Stomach mechanical properties may be determined based on stomach water content. Surgical tool parameter adjustments may be generated based on the stomach mechanical properties. Surgical tool parameter adjustments may be generated based on key components of tissue strength and/or friability. Post-surgery leakage may be predicted based on key components of tissue strength and/or friability.

Lower GI

The lower GI may include the small intestine, colon, and/or rectum. For example, based on the selected biomarker sensing systems data, small intestine-related biomarkers, complications, contextual information, and/or conditions may be determined, including caloric absorption rate, nutrient absorption rate, bacteria presence, and/or recovery rate. Based on the selected biomarker sensing systems data, small intestine-related conditions may be predicted, including ileus and/or inflammation. The small intestine biomarkers may include muscularis, serosa, lumen, mucosa, and/or mechanical properties. For example, post-operation small bowel motility changes may be determined based on GI motility. Ileus may be predicted based on post-operation small bowel motility changes. GI motility may determine caloric and/or nutrient absorption rates. Future weight loss may be predicted based on accelerated absorption rates. Absorption rates may be determined based on fecal rates, composition, and/or pH. Inflammation may be predicted based on lumen content biomarkers. Lumen content biomarkers may include pH, bacteria presence, and/or bacteria amount. Mechanical properties may be determined based on predicted inflammation. Mucosa inflammation may be predicted based on stool inflammatory markers. Stool inflammatory markers may include calprotectin. Tissue property changes may be determined based on mucosa inflammation. Recovery rate changes may be determined based on mucosa inflammation.

For example, based on the selected biomarker sensing systems data, colon and rectum-related biomarkers, complications, and/or contextual information may be determined, including small intestine tissue strength, small intestine tissue thickness, contraction ability, water content, colon and rectum tissue perfusion pressure, colon and rectum tissue thickness, colon and rectum tissue strength, and/or colon and rectum tissue friability. Based on the selected biomarker sensing systems data, colon and rectum-related conditions may be predicted, including inflammation, anastomotic leak, ulcerative colitis, Crohn's disease, and/or infection. Colon and rectum may include mucosa, muscularis, serosa, lumen, function, and/or mechanical properties. In an example, mucosa inflammation may be predicted based on stool inflammatory markers. Stool inflammatory markers may include calprotectin. An increase in anastomotic leak risk may be determined based on inflammation.

Surgical tool parameter adjustments may be generated based on the determined increased risk of anastomotic leak. Inflammatory conditions may be predicted based on GI tract imaging. Inflammatory conditions may include ulcerative colitis and/or Crohn's disease. Inflammation may increase the risk of anastomotic leak. Surgical tool parameter adjustments may be generated based on inflammation. In an example, the key components of tissue strength and/or thickness may be determined based on collagen content. In an example, colon contraction ability may be determined based on smooth muscle alpha-actin expression. In an example, the inability of colon areas to contract may be determined based on abnormal expression. Colon contraction inability may be determined and/or predicted based on pseudo-obstruction and/or ileus. In an example, adhesions, fistula, and/or scar tissue may be predicted based on serosa biomarkers. Colon infection may be predicted based on bacterial presence in stool. The stool bacteria may be identified. The bacteria may include commensals and/or pathogens. In an example, inflammatory conditions may be predicted based on pH. Mechanical properties may be determined based on inflammatory conditions. Gut inflammation may be predicted based on ingested allergens. Constant exposure to ingested allergens may increase gut inflammation. Gut inflammation may change mechanical properties. In an example, mechanical properties may be determined based on tissue perfusion pressure. Water content may be determined based on tissue perfusion pressure. Surgical tool parameter adjustments may be generated based on determined mechanical properties.

Ancillary Organs

Ancillary organs may include the pancreas, liver, spleen, and/or gallbladder. Based on the selected biomarker sensing systems data, ancillary organ-related biomarkers, complications, and/or contextual information may be determined including gastric emptying speed, liver size, liver shape, liver location, tissue health, and/or blood loss response. Based on the selected biomarker sensing systems data, ancillary organ-related conditions may be predicted, including gastroparesis. For example, gastric emptying speed may be determined based on enzyme load and/or titratable base biomarkers. Gastroparesis may be predicted based on gastric emptying speed. Lymphatic tissue health may be determined based on lymphocyte storage status. A patient's ability to respond to an SSI may be determined based on lymphatic tissue health. Venous sinuses tissue health may be determined based on red blood cell storage status. A patient's response to blood loss in surgery may be predicted based on venous sinuses tissue health.

Nutritional State

Nutritional states may include short-term nutrition, long-term nutrition, and/or systemic nutrition. Based on the selected biomarker sensing systems data, nutritional state-related biomarkers, complications, and/or contextual information may be determined, including immune function. Based on the selected biomarker sensing systems data, nutritional state-related conditions may be predicted, including cardiac issues. Reduced immune function may be determined based on nutrient biomarkers. Cardiac issues may be predicted based on nutrient biomarkers. Nutrient biomarkers may include macronutrients, micronutrients, alcohol consumption, and/or feeding patterns.

Microbiome

Patients who have had gastric bypass may have an altered gut microbiome that may be measured in the feces.

The detection, prediction, determination, and/or generation described herein may be performed by a computing system described herein, such as a surgical hub, a computing device, and/or a smart device based on measured data and/or related biomarkers generated by the biomarker sensing systems.

Respiratory System

The respiratory system may include the upper respiratory tract, lower respiratory tract, respiratory muscles, and/or system contents. The upper respiratory tract may include the pharynx, larynx, mouth and oral cavity, and/or nose. The lower respiratory tract may include the trachea, bronchi, aveoli, and/or lungs. The respiratory muscles may include the diaphragm and/or intercostal muscles. Respiratory system-related biomarkers, complications, contextual information, and/or conditions may be determined and/or predicted based on analyzed biomarker sensing systems data. A computing system, as described herein, may select one or more biomarkers (e.g., data from biomarker sensing systems) from respiratory system-related biomarkers, including bacteria, coughing and sneezing, respiration rate, VO2 max, and/or activity for analysis.

The upper respiratory tract may include the pharynx, larynx, mouth and oral cavity, and/or nose. For example, based on the selected biomarker sensing systems data, upper respiratory tract-related biomarkers, complications, and/or contextual information may be determined. Based on the selected biomarker sensing systems data, upper respiratory tract-related conditions may be predicted, including SSI, inflammation, and/or allergic rhinitis. In an example, SSI may be predicted based on bacteria and/or tissue biomarkers. Bacteria biomarkers may include commensals and/or pathogens. Inflammation may be indicated based on tissue biomarkers. Mucosa inflammation may be predicted based on nose biomarkers, including coughing and sneezing. General inflammation and/or allergic rhinitis may be predicted based on mucosa biomarkers. Mechanical properties of various tissues may be determined based on systemic inflammation.

The lower respiratory tract may include the trachea, bronchi, aveoli, and/or lungs. For example, based on the selected biomarker sensing systems data, lower respiratory tract-related biomarkers, complications, and/or contextual information may be determined, including bronchopulmonary segments. Based on the selected biomarker sensing systems data, lower respiratory tract-related conditions may be predicted. Surgical tool parameter adjustments may be generated based on the determined biomarkers, complications, and/or contextual information. Surgical tool parameter adjustments may be generated based on the predicted conditions.

Based on the selected biomarker sensing systems data, lung-related biomarkers, complications, and/or contextual information may be determined, including poor surgical tolerance. Lung-related biomarkers may include lung respiratory mechanics, lung disease, lung surgery, lung mechanical properties, and/or lung function. Lung respiratory mechanics may include total lung capacity (TLC), tidal volume (TV), residual volume (RV), expiratory reserve volume (ERV), inspiratory reserve volume (IRV), inspiratory capacity (IC), inspiratory vital capacity (IVC), vital capacity (VC), functional residual capacity (FRC), residual volume expressed as a percent of total lung capacity (RV/TLC %), alveolar gas volume (VA), lung volume (VL), forced vital capacity (FVC), forced expiratory volume over time (FEVt), difference between inspired and expired carbon monoxide (DLco), volume exhaled after first second of forced expiration (FEV1), forced expiratory flow related to portion of functional residual capacity curve (FEFx), maximum instantaneous flow during functional residual capacity (FEFmax), forced inspiratory flow (FIF), highest forced expiratory flow measured by peak flow meter (PEF), and maximal voluntary ventilation (MVV).

TLC may be determined based on lung volume at maximal inflation. TV may be determined based on volume of air moved into or out of the lungs during quiet breathing. RV may be determined based on air volume remaining in lungs after a maximal exhalation. ERV may be determined based on maximal volume inhaled from the end-inspiratory level. IC may be determined based on aggregated IRV and TV values. IVC may be determined based on maximum air volume inhaled at the point of maximum expiration. VC may be determined based on the difference between the RV value and TLC value. FRC may be determined based on the lung volume at the end-expiratory position. FVC may be determined based on the VC value during a maximally forced expiratory effort. Poor surgical tolerance may be determined based on the difference between inspired and expired carbon monoxide, such as when the difference falls below 60%. Poor surgical tolerance may be determined based on the volume exhaled at the end of the first second of force expiration, such as when the volume falls below 35%. MVV may be determined based on the volume of air expired in a specified period during repetitive maximal effort.

Based on the selected biomarker sensing systems data, lung-related conditions may be predicted, including emphysema, chronic obstructive pulmonary disease, chronic bronchitis, asthma, cancer, and/or tuberculosis. Lung diseases may be predicted based on analyzed spirometry, x-rays, blood gas, and/or diffusion capacity of the aveolar capillary membrane. Lung diseases may narrow airways and/or create airway resistance. Lung cancer and/or tuberculosis may be detected based on lung-related biomarkers, including persistent coughing, coughing blood, shortness of breath, chest pain, hoarseness, unintentional weight loss, bone pain, and/or headaches. Tuberculosis may be predicted based on lung symptoms including coughing for 3 to 5 weeks, coughing blood, chest pain, pain while breathing or coughing, unintentional weight loss, fatigue, fever, night sweats, chills, and/or loss of appetite.

Surgical tool parameter adjustments and surgical procedure adjustments may be generated based on lung-related biomarkers, complications, contextual information, and/or conditions. Surgical procedure adjustments may include pneumonectomy, lobectomy, and/or sub-local resections. In an example, a surgical procedure adjustment may be generated based on a cost-benefit analysis between adequate resection and the physiologic impact on a patient's ability to recover functional status. Surgical tool parameter adjustments may be generated based on determined surgical tolerance. Surgical tolerance may be determined based on the FEC1 value. Surgical tolerance may be considered adequate when FEV1 exceeds a certain threshold, which may include values above 35%. Post-operation surgical procedure adjustments, including oxygenation and/or physical therapy, may be generated based on determined pain scores. Post-operation surgical procedure adjustments may be generated based on air leak. Air leak may increase cost associated with the post-surgical recovery and morbidity following lung surgery.

Lung mechanical property-related biomarkers may include perfusion, tissue integrity, and/or collagen content. Plura perfusion pressure may be determined based on lung water content levels. Mechanical properties of tissue may be determined based on plura perfusion pressure. Surgical tool parameter adjustments may be generated based on plura perfusion pressure. Lung tissue integrity may be determined based on elasticity, hydrogen peroxide (H2O2) in exhaled breath, lung tissue thickness, and/or lung tissue shear strength. Tissue friability may be determined based on elasticity. Surgical tool parameter adjustments may be generated based on post-surgery leakage. Post-surgery leakage may be predicted based on elasticity. In an example, fibrosis may be predicted based on H2O2 in exhaled breath. Fibrosis may be determined and/or predicted based on increased H2O2 concentration. Surgical tool parameter adjustments may be generated based on predicted fibrosis. Increased scarring in lung tissue may be determined based on predicted fibrosis. Surgical tool parameter adjustments may be generated based on determined lung tissue strength. Lung tissue strength may be determined based on lung thickness and/or lung tissue shear strength. Post-surgery leakage may be predicted based on lung tissue strength.

Respiratory muscles may include the diaphragm and/or intercostal muscles. Based on the selected biomarker sensing systems data, respiratory muscle-related biomarkers, complications, and/or contextual information may be determined. Based on the selected biomarker sensing systems data, respiratory muscle-related conditions may be predicted, including respiratory tract infections, collapsed lung, pulmonary edema, post-operation pain, air leak, and/or serious lung inflammation. Respiratory muscle-related conditions, including respiratory tract infections, collapsed lung, and/or pulmonary edema, may be predicted based on diaphragm-related biomarkers, including coughing and/or sneezing. Respiratory muscle-related conditions, including post-operation pain, air leak, collapsed lung, and/or serious lung inflammation may be predicted based on intercostal muscle biomarkers, including respiratory rate.

Based on the selected biomarker sensing systems data, respiratory system content-related biomarkers, complications, and/or contextual information may be determined, including post-operation pain, healing ability, and/or response to surgical injury. Based on the selected biomarker sensing systems data, respiratory system content-related conditions may be predicted, including inflammation and/or fibrosis. The selected biomarker sensing systems data may include environmental data, including mycotoxins and/or airborne chemicals. Respiratory system content-related conditions may be predicted based on airborne chemicals. Inflammation and/or fibrosis may be predicted based on irritants in the environment. Mechanical properties of tissue may be determined based on inflammation and/or fibrosis. Post-operation pain may be determined based on irritants in the environment. Airway inflammation may be predicted based on analyzed mycotoxins and/or arsenic. Surgical tool parameter adjustments may be generated based on airway inflammation. Altered tissue properties may be determined based on analyzed arsenic.

The detection, prediction, determination, and/or generation described herein may be performed by a computing system described herein, such as a surgical hub, a computing system, and/or a smart device based on measured data and/or related biomarkers generated by the biomarker sensing systems.

Endocrine System

The endocrine system may include the hypothalamus, pituitary gland, thymus, adrenal gland, pancreas, testes, intestines, ovaries, thyroid gland, parathyroid, and/or stomach. Endocrine system-related biomarkers, complications, and/or contextual information may be determined based on analyzed biomarker sensing systems data, including immune system function, metastasis, infection risk, insulin secretion, collagen production, menstrual phase, and/or high blood pressure. Endocrine system-related conditions may be predicted based on analyzed biomarker sensing systems data. A computing system, as described herein, may select one or more biomarkers (e.g., data from biomarker sensing systems) from endocrine system-related biomarkers, including hormones, blood pressure, adrenaline, cortisol, blood glucose, and/or menstrual cycle for analysis. Surgical tool parameter adjustments and/or surgical procedure adjustments may be generated based on the endocrine system-related biomarkers, complications, contextual information, and/or conditions.

For example, based on the selected biomarker sensing systems data, hypothalamus-related biomarkers, complications, and/or contextual information may be determined, including blood pressure regulation, kidney function, osmotic balance, pituitary gland control, and/or pain tolerance. Based on the selected biomarker sensing systems data, hypothalamus-related conditions may be predicted, including edema. The hormone biomarkers may include antidiuretic hormone (ADH) and/or oxytocin. ADH may affect blood pressure regulation, kidney function, osmotic balance, and/or pituitary gland control. Pain tolerance may be determined based on analyzed oxytocin. Oxytocin may have an analgesic effect. Surgical tool parameter adjustments may be generated based on predicted edema.

For example, based on the selected biomarker sensing systems data, pituitary gland-related biomarkers, complications, and/or contextual information may be determined, including circadian rhythm entrainment, menstrual phase, and/or healing speed. Based on the selected biomarker sensing systems data, pituitary gland-related conditions may be predicted. Circadian entrainment may be determined based on adrenocorticotropic hormones (ACTH). Circadian rhythm entrainment may provide context for various surgical outcomes. Menstrual phase may be determined based on reproduction function hormone biomarkers. Reproduction function hormone biomarkers may include luteinizing hormone and/or follicle stimulating hormone. Menstrual phase may provide context for various surgical outcomes. The menstrual cycle may provide context for biomarkers, complications, and/or conditions, including those related to the reproductive system. Wound healing speed may be determined based on thyroid regulation hormones, including thyrotropic releasing hormone (TRH).

For example, based on the selected biomarker sensing systems data, thymus-related biomarkers, complications, and/or contextual information may be determined, including immune system function. Based on the selected biomarker sensing systems data, thymus-related conditions may be predicted. Immune system function may be determined based on thymosins. Thymosins may affect adaptive immunity development.

For example, based on the selected biomarker sensing systems data, adrenal gland-related biomarkers, complications, and/or contextual information may be determined, including metastasis, blood vessel health, immunity level, and/or infection risk. Based on the selected biomarker sensing system data, adrenal gland-related conditions may be predicted, including edema. Metastasis may be determined based on analyzed adrenaline and/or nonadrenaline. Blood vessel health may be determined based on analyzed adrenaline and/or nonadrenaline. A blood vessel health score may be generated based on the determined blood vessel health. Immunity capability may be determined based on analyzed cortisol. Infection risk may be determined based on analyzed cortisol. Metastasis may be predicted based on analyzed cortisol. Circadian rhythm may be determined based on measured cortisol. High cortisol may lower immunity, increase infection risk, and/or lead to metastasis. High cortisol may affect circadian rhythm. Edema may be predicted based on analyzed aldosterone. Aldosterone may promote fluid retention. Fluid retention may relate to blood pressure and/or edema.

For example, based on the selected biomarker sensing systems data, pancreas-related biomarkers, complications, and/or contextual information may be determined, including blood sugar, hormones, polypeptides, and/or blood glucose control. Based on the selected biomarker sensing systems data, pancreas-related conditions may be predicted. The pancreas-related biomarkers may provide contextual information for various surgical outcomes. Blood sugar biomarkers may include insulin. Hormone biomarkers may include somatostatin. Polypeptide biomarkers may include pancreatic polypeptide. Blood glucose control may be determined based on insulin, somatostatin, and/or pancreatic polypeptide. Blood glucose control may provide contextual information for various surgical outcomes.

For example, based on the selected biomarker sensing systems data, testes-related biomarkers, complications, and/or contextual information may be determined, including reproductive development, sexual arousal, and/or immune system regulation. Based on the selected biomarker sensing systems data, testes-related conditions may be predicted. Testes-related biomarkers may include testosterone. Testosterone may provide contextual information for biomarkers, complications, and/or conditions, including those relating to the reproductive system. High levels of testosterone may suppress immunity.

For example, based on the selected biomarker sensing systems data, stomach/testes-related biomarkers, complications, and/or contextual information may be determined, including glucose handling, satiety, insulin secretion, digestion speed, and/or sleeve gastrectomy outcomes. Glucose handling and satiety biomarkers may include glucagon-like peptide-1 (GLP-1), cholecystokinin (CCK), and/or peptide YY. Appetite and/or insulin secretion may be determined based on analyzed GLP-1. Increased GLP-1 may be determined based on enhanced appetite and insulin secretion. Sleeve gastrectomy outcomes may be determined based on analyzed GLP-1. Satiety and/or sleeve gastrectomy outcomes may be determined based on analyzed CCK. Enhanced CCK levels may be predicted based on previous sleeve gastrectomy. Appetite and digestion speeds may be determined based on analyzed peptide YY. Increased peptide YY may reduce appetite and/or increase digestion speeds.

For example, based on the selected biomarker sensing systems data, hormone-related biomarkers, complications, and/or contextual information may be determined, including estrogen, progesterone, collagen product, fluid retention, and/or menstrual phase. Collagen production may be determined based on estrogen. Fluid retention may be determined based on estrogen. Surgical tool parameter adjustments may be generated based on determined collagen production and/or fluid retention.

For example, based on the selected biomarker sensing systems data, thyroid gland and parathyroid-related biomarkers, complications, and/or contextual information may be determined, including calcium handling, phosphate handling, metabolism, blood pressure, and/or surgical complications. Metabolism biomarkers may include triiodothyronine (T3) and/or thyroxine (T4). Blood pressure may be determined based on analyzed T3 and T4. High blood pressure may be determined based on increased T3 and/or increased T4. Surgical complications may be determined based on analyzed T3 and/or T4.

For example, based on the selected biomarker sensing systems data, stomach-related biomarkers, complications, and/or contextual information may be determined, including appetite. Stomach-related biomarkers may include ghrelin. Ghrelin may induce appetite.

The detection, prediction, determination, and/or generation described herein may be performed by a computing system described herein, such as a surgical hub, a computing system, and/or a smart device based on measured data and/or related biomarkers generated by the biomarker sensing systems.

Immune System

Immune system-related biomarkers may relate to antigens and irritants, antimicrobial enzymes, the complement system, chemokines and cytokines, the lymphatic system, bone marrow, pathogens, damage-associated molecular patterns (DAMPs), and/or cells. Immune system-related biomarkers, complications, and/or contextual information may be determined based on analyzed biomarker sensing systems data. A computing system, as described herein, may select one or more biomarkers (e.g., data from biomarker sensing systems) from immune system-related biomarkers, including alcohol consumption, pH, respiratory rate, edema, sweat, and/or environment for analysis.

Antigens/Irritants

For example, based on the selected biomarker sensing systems data, antigen and irritant-related biomarkers, complications, and/or contextual information may be determined, including healing ability, immune function, and/or cardiac issues. Based on the selected biomarker sensing systems data, antigen and irritant-related conditions may be predicted, including inflammation. Antigen and irritant-related biomarkers may include inhaled chemicals, inhaled irritants, ingested chemicals, and/or ingested irritants. Inhaled chemicals or irritants may be determined based on analyzed environmental data, including airborne chemicals, mycotoxins, and/or arsenic. Airborne chemicals may include cigarette smoke, asbestos, crystalline silica, alloy particles, and/or carbon nanotubes. Lung inflammation may be predicted based on analyzed airborne chemicals. Surgical tool parameter adjustments may be generated based on determined lung inflammation. Airway inflammation may be predicted based on analyzed mycotoxin and/or arsenic. Surgical tool parameter adjustments may be generated based on determined airway inflammation. Arsenic exposure may be determined based on urine, saliva, and/or ambient air sample analyses.

Antimicrobial Enzymes and Other Molecules Related to Inflammation

For example, based on the selected biomarker sensing systems data, antimicrobial enzyme-related biomarkers, complications, and/or contextual information may be determined, including colon state. Based on the selected biomarker sensing systems data, antimicrobial enzyme-related conditions may be predicted, including GI inflammation, acute kidney injury, *E. faecalis* infection, and/or *S. aureus* infection. Antimicrobial enzyme biomarkers may include lysozyme, lipocalin-2 (NGAL), and/or orosomuccoid. GI inflammation may be predicted based on analyzed lysozyme. Increased levels in lysozyme may be determined and/or predicted based on GI inflammation. Colon state may be determined based on analyzed lysozyme. Surgical tool parameter adjustments may be generated based on analyzed lysozyme levels. Acute kidney injury may be predicted based on analyzed NGAL. NGAL may be detected from serum and/or urine.

Complement and Related Molecules

For example, based on the selected biomarker sensing systems data, complement system-related biomarkers, complications, and/or contextual information may be determined, including bacterial infection susceptibility. Bacterial infection susceptibility may be determined based on analyzed complement system deficiencies.

Chemokines/Cytokines

For example, based on the selected biomarker sensing systems data, chemokine and cytokine-related biomarkers, complications, and/or contextual information may be determined, including infection burden, inflammation burden, vascular permeability regulation, omentin, colonic tissue properties, and/or post-operation recovery. Based on the selected biomarker sensing systems data, chemokine and cytokine-related conditions may be predicted, including inflammatory bowel diseases, post-operation infection, lung fibrosis, lung scarring, pulmonary fibrosis, gastroesophageal reflux disease, cardiovascular disease, edema, and/or hyperplasia. Infection and/or inflammation burden biomarkers may include oral, salivary, exhaled, and/or C-reactive protein (CRP) data. Salivary cytokines may include interleukin-1 beta (IL-1β), interleukin-6 (IL-6), tumor necrosis factor alpha (TNF-α) and/or interleukin-8 (IL-8).

In an example, inflammatory bowel diseases may be predicted based on analyzed salivary cytokines. Increased salivary cytokines may be determined based on inflammatory bowel diseases. Colonic tissue properties may be determined based on predicted inflammatory bowel diseases. Colonic tissue properties may include scarring, edema, and/or ulcering. Post-operation recovery and/or infection may be determined based on predicted inflammatory bowel diseases. Tumor size and/or lung scarring may be determined based on analyzed exhaled biomarkers. Lung fibrosis, pulmonary fibrosis, and/or gastroesophageal reflux disease may be predicted based on analyzed exhaled biomarkers. Exhaled biomarkers may include exhaled cytokines, pH, hydrogen peroxide (H2O2), and/or nitric oxide. Exhaled cytokines may include IL-6, TNF-α, and/or interleukin-17 (IL-17). Lung fibrosis may be predicted based on measured pH and/or H2O2 from exhaled breath. Fibrosis may be predicted based on increased H2O2 concentration. Increased lung tissue scarring may be predicted based on fibrosis. Surgical tool parameter adjustments may be generated based on predicted lung fibrosis. In an example, pulmonary fibrosis and/or gastroesophageal reflux disease may be predicted based on analyzed exhaled nitric oxide. Pulmonary fibrosis may be predicted based on determined increased nitrates and/or nitrites. Gastroesophageal disease may be predicted based on determined reduced nitrates and/or nitrites. Surgical tool parameter adjustments may be generated based on predicted pulmonary fibrosis and/or gastroesophageal reflux disease. Cardiovascular disease, inflammatory bowel diseases, and/or infection may be predicted based on analyzed CRP biomarkers. Risk of serious cardiovascular disease may increase with high CRP concentration. Inflammatory bowel disease may be predicted based on elevated CRP concentration. Infection may be predicted based on elevated CRP concentration. In an example, edema may be predicted based on analyzed vascular permeability regulation biomarkers. Increased vascular permeability during inflammation may be determined based on analyzed bradykinin and/or histamine. Edema may be predicted based on increased vascular permeability during inflammation. Vascular permeability may be determined based on endothelial adhesion molecules. Endothelial adhesion molecules may be determined based on cell samples. Endothelial adhesion molecules may affect vascular permeability, immune cell recruitment, and/or fluid build-up in edema. Surgical tool parameter adjustments may be generated based on analyzed vascular permeability regulation biomarkers. In an example, hyperplasia may be predicted based on analyzed omentin. Hyperplasia may alter tissue properties. Surgical tool parameter adjustments may be generated based on predicted hyperplasia.

Lymphatic System

For example, based on the selected biomarker sensing systems data, lymphatic system-related biomarkers, complications, and/or contextual information may be determined, including lymph nodes, lymph composition, lymph location, and/or lymph swelling. Based on the selected biomarker sensing systems data, lymphatic system-related conditions may be predicted, including post-operation inflammation, post-operation infection, and/or fibrosis. Post-operation inflammation and/or infection may be predicted based on determined lymph node swelling. Surgical tool parameter adjustments may be generated based on the analyzed lymph node swelling. Surgical tool parameter adjustments, including harmonic tool parameter adjustments, may be generated based on the determined collagen deposition. Collagen deposition may increase with lymph node fibrosis. Inflammatory conditions may be predicted based on lymph composition. Metastatic cell spread may be determined based on lymph composition. Surgical tool parameter adjustments may be generated based on lymph peptidome. Lymph peptidome may change based on inflammatory conditions.

Pathogens

For example, based on the selected biomarker sensing systems data, pathogen-related biomarkers, complications, and/or contextual information may be determined, including pathogen-associated molecular patterns (PAMPs), pathogen burden, *H. Pylori*, and/or stomach tissue properties. Based on the selected biomarker sensing systems data, pathogen-related conditions may be predicted, including infection, stomach inflammation, and/or ulcering. PAMPs biomarkers may include pathogen antigens. Pathogen antigens may impact pathogen burden. Stomach inflammation and/or potential ulcering may be predicted based on predicted infection. Stomach tissue property alterations may be determined based on predicted infection.

Damage DAMPs (Damage-Associated Molecular Patterns)

For example, based on the selected biomarker sensing systems data, DAMPs-related biomarkers, complications, and/or contextual information may be determined, including stress (e.g., cardiovascular, metabolic, glycemic, and/or cellular) and/or necrosis. Based on the selected biomarker sensing systems data, DAMPs-related conditions may be predicted, including acute myocardial infarction, intestinal inflammation, and/or infection. Cellular stress biomarkers may include creatine kinase MB, pyruvate kinase isoenzyme type M2 (M2-PK), irisin, and/or microRNA. In an example, acute myocardial infarction may be predicted based on analyzed creatine kinase MB biomarkers. Intestinal inflammation may be predicted based on analyzed M2-PK biomarkers. Stress may be determined based on analyzed irisin biomarkers. Inflammatory diseases and/or infection may be predicted based on analyzed microRNA biomarkers. Surgical tool parameter adjustments may be generated based on predicted inflammation and/or infection. Inflammation and/or infection may be predicted based on analyzed necrosis biomarkers. Necrosis biomarkers may include reactive oxygen species (ROS). Inflammation and/or infection may be predicted based on increased ROS. Post-operation recovery may be determined based on analyzed ROS.

Cells

For example, based on the selected biomarker sensing systems, cell-related biomarkers, complications, and/or contextual information may be determined, including granulocytes, natural killer cells (NK cells), macrophages, lymphocytes, and/or colonic tissue properties. Based on the selected biomarker sensing systems, cell-related conditions may be predicted, including post-operation infection, ulceratic colitis, inflammation, and/or inflammatory bowel disease. Granulocyte biomarkers may include eosinophilia and/or neutrophils. Eosinophilia biomarkers may include sputum cell count, eosinophilic cationic protein, and/or fractional exhaled nitric oxide. Neutrophil biomarkers may include S100 proteins, myeloperoxidase, and/or human neutrophil lipocalin. Lymphocyte biomarkers may include antibodies, adaptive response, and/or immune memory. The antibodies may include immunoglobulin A (IgA) and/or immunoglobulin M (IgM). In an example, post-operational infection and/or pre-operation inflammation may be predicted based on analyzed sputum cell count. Ulcerative colitis may be predicted based on analyzed eosinophilic cationic protein. Altered colonic tissue properties may be determined based on the predicted ulcerative colitis. Eosinophils may produce eosinophilic cationic protein which may be determined based on ulcerative colitis. Inflammation may be predicted based on analyzed fractional exhaled nitric oxide. The inflammation may include type 1 asthma-like inflammation. Surgical tool parameter adjustments may be generated based on the predicted inflammation. In an example, inflammatory bowel diseases may be predicted based on S100 proteins. The S100 proteins may include calprotectin. Colonic tissue properties may be determined based on the predicted inflammatory bowel diseases. Ulcerative colitis may be predicted based on analyzed myeloperoxidase and/or human neutrophil lipocalin. Altered colonic tissue properties may be determined based on predicted ulcerative colitis. In an example, inflammation may be predicted based on antibody biomarkers. Bowel inflammation may be predicted based on IgA. Cardiovascular inflammation may be predicted based on IgM.

The detection, prediction, determination, and/or generation described herein may be performed by a computing system described herein, such as a surgical hub, a computing device, and/or a smart device based on measured data and/or related biomarkers generated by the biomarker sensing systems.

Tumor

Tumors may include benign and/or malignant tumors. Tumor-related biomarkers, complications, contextual information, and/or conditions may be determined and/or predicted based on analyzed biomarker sensing systems data. A computing system, as described herein, may select one or more biomarkers (e.g., data from biomarker sensing systems) from tumor-related biomarkers, including circulating tumor cells for analysis.

For example, based on the selected biomarker sensing systems data, benign tumor-related biomarkers, conditions, and/or contextual information may be determined, including benign tumor replication, benign tumor metabolism, and/or benign tumor synthesis. Benign tumor replication may include rate of mitotic activity, mitotic metabolism, and/or synthesis biomarkers. Benign tumor metabolism may include metabolic demand and/or metabolic product biomarkers. Benign tumor synthesis may include protein expression and/or gene expression biomarkers.

For example, based on the selected biomarker sensing systems data, malignant tumor-related biomarkers, complications, and/or contextual information may be determined, including malignant tumor synthesis, malignant tumor metabolism, malignant tumor replication, microsatellite stability, metastatic risk, metastatic tumors, tumor growth, tumor recession, and/or metastatic activity. Based on the selected biomarker sensing systems data, malignant tumor-related conditions may be predicted, including cancer. Malignant tumor synthesis may include gene expression and/or protein expression biomarkers. Gene expression may be determined based on tumor biopsy and/or genome analysis. Protein expression biomarkers may include cancer antigen 125 (CA-125) and/or carcinoembryonic antigen (CEA). CEA may be measured based on urine and/or saliva. Malignant tumor replication data may include rate of mitotic activity, mitotic encapsulation, tumor mass, and/or microRNA 200*c*.

In an example, microsatellite stability may be determined based on analyzed gene expression. Metastatic risk may be determined based on determined microsatellite stability. Higher metastatic risk may be determined and/or predicted based on low microsatellite instability. In an example, metastatic tumors, tumor growth, tumor metastasis, and/or tumor recession may be determined based on analyzed protein expression. Metastatic tumors may be determined and/or predicted based on elevated CA-125. Cancer may be predicted based on CA-125. Cancer may be predicted based on certain levels of CEA. Tumor growth, metastasis, and/or recession may be monitored based on detected changes in CEA. Metastatic activity may be determined based on malignant tumor replication. Cancer may be predicted based on malignant tumor replication. MicroRNA 200*c* may be released into blood by certain cancers. Metastatic activity may be determined and/or predicted based on presence of circulating tumor cells.

The detection, prediction, determination, and/or generation described herein may be performed by a computing system described herein, such as a surgical hub, a computing device, and/or a smart device based on measured data and/or related biomarkers generated by the biomarker sensing systems.

Musculoskeletal

The musculoskeletal system may include muscles, bones, marrow, and/or cartilage. The muscles may include smooth muscle, cardiac muscle, and/or skeletal muscle. The smooth muscle may include calmodulin, connective tissue, structural features, hyperplasia, actin, and/or myosin. The bones may include calcified bone, osteoblasts, and/or osteoclasts. The marrow may include red marrow and/or yellow marrow. The cartilage may include cartilaginous tissue and/or chondrocytes. Musculoskeletal system-related biomarkers, complications, contextual information, and/or conditions may be determined and/or predicted based on analyzed biomarker sensing systems data. A computing system, as described herein, may select one or more biomarkers (e.g., data from biomarker sensing systems) from musculoskeletal-related biomarkers for analysis.

For example, based on the selected biomarker sensing systems data, muscle-related biomarkers, complications, and/or contextual information may be determined, including serum calmodulin levels, mechanical strength, muscle body, hyperplasia, muscle contraction ability, and/or muscle damage. Based on the selected biomarker sensing systems data, muscle-related conditions may be predicted. In an example, neurological conditions may be predicted based on analyzed serum calmodulin levels. Mechanical strength may be determined based on analyzed smooth muscle collagen levels. Collagen may affect mechanical strength as collagen may bind smooth muscle filament together. Muscle body may be determined based on analyzed structural features. The muscle body may include an intermediate body and/or a dense body. Hyperplasia may be determined based on analyzed omentin levels. Omentin may indicate hyperplasia. Hyperplasia may be determined and/or predicted based on thick areas of smooth muscles. Muscle contraction ability may be determined based on analyzed smooth muscle alpha-actin expression. Muscle contraction inability may result from an abnormal expression of actin in smooth muscle. In an example, muscle damage may be determined based on analyzed circulating smooth muscle myosin and/or skeletal muscle myosin. Muscle strength may be determined based on analyzed circulating smooth muscle myosin. Muscle damage and/or weak, friable smooth muscle may be determined and/or predicted based on circulating smooth muscle myosin and/or skeletal muscle myosin. Smooth muscle myosin may be measured from urine. In an example, muscle damage may be determined based on cardiac and/or skeletal muscle biomarkers. Cardiac and/or skeletal muscle biomarkers may include circulating troponin. Muscle damage may be determined and/or predicted based on circulating troponin alongside myosin.

For example, based on the selected biomarker sensing systems data, bone-related biomarkers, complications, and/or contextual information may be determined, including calcified bone properties, calcified bone functions, osteoblasts number, osteoid secretion, osteoclasts number, and/or secreted osteoclasts.

For example, based on the selected biomarker sensing systems data, marrow-related biomarkers, complications, and/or contextual information may be determined, including tissue breakdown and/or collagen secretion. Arthritic breakdown of cartilaginous tissue may be determined based on analyzed cartilaginous tissue biomarkers. Collage secretion by muscle cells may be determined based on analyzed chondrocyte biomarkers.

The detection, prediction, determination, and/or generation described herein may be performed by a computing system described herein, such as a surgical hub, a computing device, and/or a smart device based on measured data and/or related biomarkers generated by the biomarker sensing systems.

Reproductive System

Reproductive system-related biomarkers, complications, contextual information, and/or conditions may be determined and/or predicted based on analyzed biomarker sensing systems data. A computing system, as described herein, may select one or more biomarkers (e.g., data from biomarker sensing systems) from reproductive system-related biomarkers for analysis. Reproductive system-related biomarkers, complications, and/or contextual information may be determined based on analyzed biomarker sensing systems data, including female anatomy, female function, menstrual cycle, pH, bleeding, wound healing, and/or scarring. Female anatomy biomarkers may include the ovaries, vagina, cervix, fallopian tubes, and/or uterus. Female function biomarkers may include reproductive hormones, pregnancy, menopause, and/or menstrual cycle. Reproductive system-related conditions may be predicted based on analyzed biomarker sensing systems data, including endometriosis, adhesions, vaginosis, bacterial infection, SSI, and/or pelvic abscesses.

In an example, endometriosis may be predicted based on female anatomy biomarkers. Adhesions may be predicted based on female anatomy biomarkers. The adhesions may include sigmoid colon adhesions. Endometriosis may be predicted based on menstrual blood. Menstrual blood may include molecular signals from endometriosis. Sigmoid colon adhesions may be predicted based on predicted endometriosis. In an example, menstrual phase and/or menstrual cycle length may be determined based on the menstrual cycle. Bleeding, wound healing, and/or scarring may be determined based on the analyzed menstrual phase. Risk of endometriosis may be predicted based on the analyzed menstrual cycle. Higher risk of endometriosis may be predicted based on shorter menstrual cycle lengths. Molecular signals may be determined based on analyzed menstrual blood and/or discharge pH. Endometriosis may be predicted based on the determined molecular signals. Vaginal pH may be determined based on analyzed discharge pH. Vaginosis and/or bacterial infections may be predicted based on the analyzed vaginal pH. Vaginosis and/or bacterial infections may be predicted based on changes in vaginal pH. Risk of SSI and/or pelvic abscesses during gynecologic procedures may be predicted based on predicted vaginosis.

The detection, prediction, determination, and/or generation described herein may be performed by any of the computing systems within any of the computer-implemented patient and surgeon monitoring systems described herein, such as a surgical hub, a computing device, and/or a smart device based on measured data and/or related biomarkers generated by the one or more sensing systems.

Figure 1B:
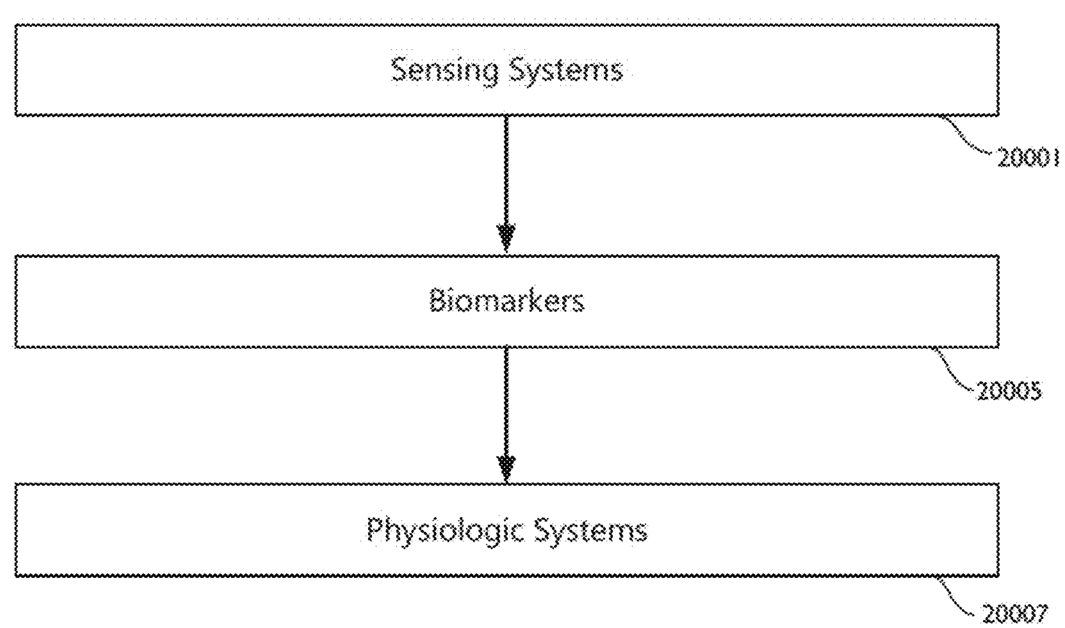
Figure 2A:
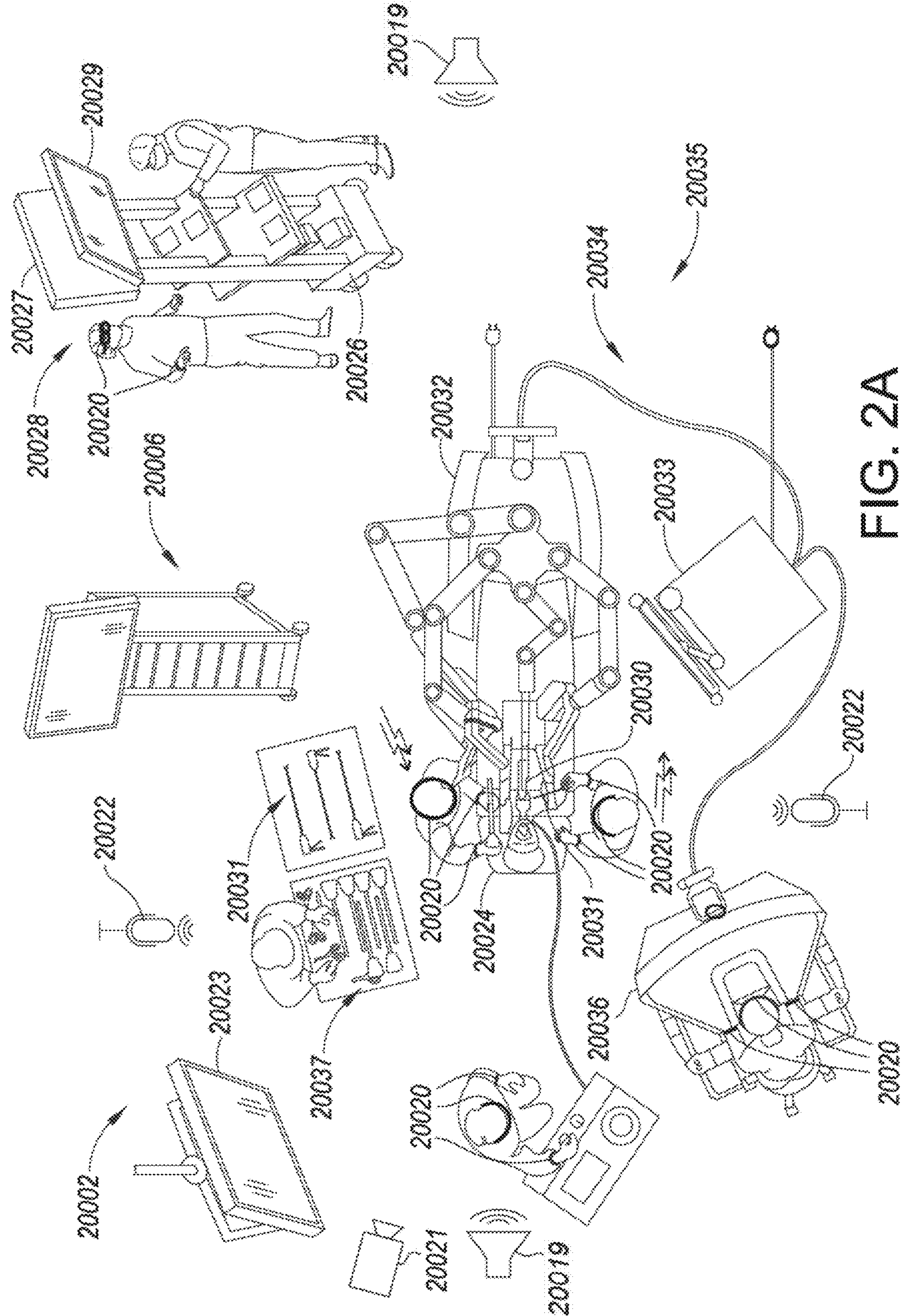
FIG. 2A shows an example of a surgeon monitoring system in a surgical operating room.

FIG. 2A shows an example of a surgeon monitoring system 20002 in a surgical operating room. As illustrated in FIG. 2A, a patient is being operated on by one or more health care professionals (HCPs). The HCPs are being monitored by one or more surgeon sensing systems 20020 worn by the HCPs. The HCPs and the environment surrounding the HCPs may also be monitored by one or more environmental sensing systems including, for example, a set of cameras 20021, a set of microphones 20022, and other sensors, etc. that may be deployed in the operating room. The surgeon sensing systems 20020 and the environmental sensing systems may be in communication with a surgical hub 20006, which in turn may be in communication with one or more cloud servers 20009 of the cloud computing system 20008, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2A, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2A, a surgical instrument 20031 is being used in the surgical procedure as part of the surgeon monitoring system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2A illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1 may include one or more sensing systems, for example, surgeon sensing systems 20020 as shown in FIG. 2A. The surgeon sensing systems 20020 may include sensing systems to monitor and detect a set of physical states and/or a set of physiological states of a healthcare provider (HCP). An HCP may be a surgeon or one or more healthcare personnel assisting the surgeon or other healthcare service providers in general. In an example, a sensing system 20020 may measure a set of biomarkers to monitor the heart rate of an HCP. In another example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the surgeon sensing systems 20020 may measure one or more surgeon biomarkers associated with an HCP and send the measurement data associated with the surgeon biomarkers to the surgical hub 20006. The surgeon sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 2B:
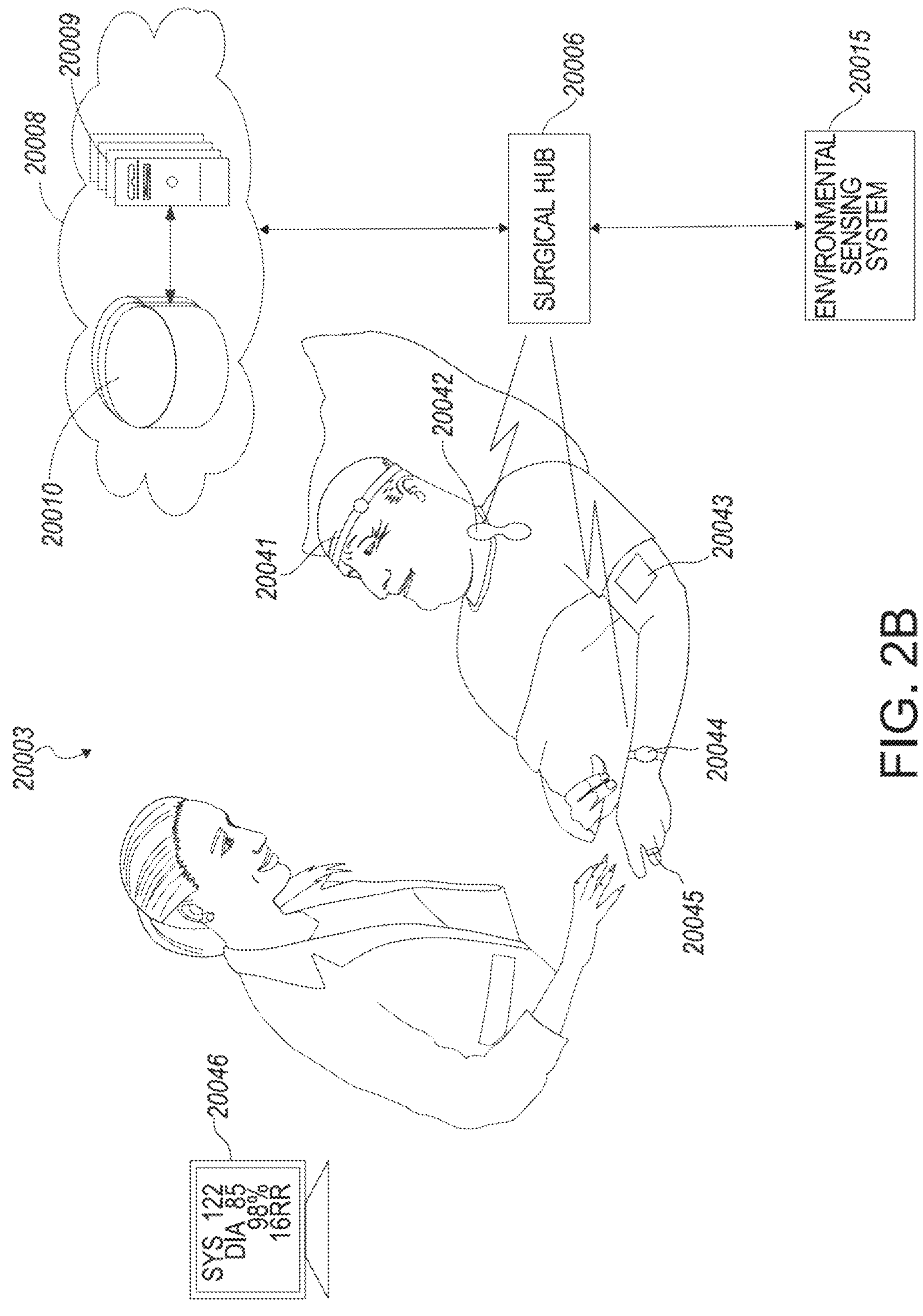
FIG. 2B shows an example of a patient monitoring system (e.g., a controlled patient monitoring system).

FIG. 2B shows an example of a patient monitoring system 20003 (e.g., a controlled patient monitoring system). As illustrated in FIG. 2B, a patient in a controlled environment (e.g., in a hospital recovery room) may be monitored by a plurality of sensing systems (e.g., patient sensing systems 20041). A patient sensing system 20041 (e.g., a head band) may be used to measure an electroencephalogram (EEG) to measure electrical activity of the brain of a patient. A patient sensing system 20042 may be used to measure various biomarkers of the patient including, for example, heart rate, VO2 level, etc. A patient sensing system 20043 (e.g., flexible patch attached to the patient's skin) may be used to measure sweat lactate and/or potassium levels by analyzing small amounts of sweat that is captured from the surface of the skin using microfluidic channels. A patient sensing system 20044 (e.g., a wristband or a watch) may be used to measure blood pressure, heart rate, heart rate variability, VO2 levels, etc. using various techniques, as described herein. A patient sensing system 20045 (e.g., a ring on finger) may be used to measure peripheral temperature, heart rate, heart rate variability, VO2 levels, etc. using various techniques, as described herein. The patient sensing systems 20041-20045 may use a radio frequency (RF) link to be in communication with the surgical hub 20006. The patient sensing systems 20041-20045 may use one or more of the following RF protocols for communication with the surgical hub 20006: Bluetooth, Bluetooth Low-Energy (BLE), Bluetooth Smart, Zigbee, Z-wave, IPv6 Low-power wireless Personal Area Network (6LoWPAN), Thread, Wi-Fi, etc.

The sensing systems 20041-20045 may be in communication with a surgical hub 20006, which in turn may be in communication with a remote server 20009 of the remote cloud computing system 20008. The surgical hub 20006 is also in communication with an HID 20046. The HID 20046 may display measured data associated with one or more patient biomarkers. For example, the HID 20046 may display blood pressure, Oxygen saturation level, respiratory rate, etc. The HID 20046 may display notifications for the patient or an HCP providing information about the patient, for example, information about a recovery milestone or a complication. In an example, the information about a recovery milestone or a complication may be associated with a surgical procedure the patient may have undergone. In an example, the HID 20046 may display instructions for the patient to perform an activity. For example, the HID 20046 may display inhaling and exhaling instructions. In an example the HID 20046 may be part of a sensing system.

As illustrated in FIG. 2B, the patient and the environment surrounding the patient may be monitored by one or more environmental sensing systems 20015 including, for example, a microphone (e.g., for detecting ambient noise associated with or around a patient), a temperature/humidity sensor, a camera for detecting breathing patterns of the patient, etc. The environmental sensing systems 20015 may be in communication with the surgical hub 20006, which in turn is in communication with a remote server 20009 of the remote cloud computing system 20008.

In an example, a patient sensing system 20044 may receive a notification information from the surgical hub 20006 for displaying on a display unit or an HID of the patient sensing system 20044. The notification information may include a notification about a recovery milestone or a notification about a complication, for example, in case of post-surgical recovery. In an example, the notification information may include an actionable severity level associated with the notification. The patient sensing system 20044 may display the notification and the actionable severity level to the patient. The patient sensing system may alert the patient using a haptic feedback. The visual notification and/or the haptic notification may be accompanied by an audible notification prompting the patient to pay attention to the visual notification provided on the display unit of the sensing system.

Figure 2C:
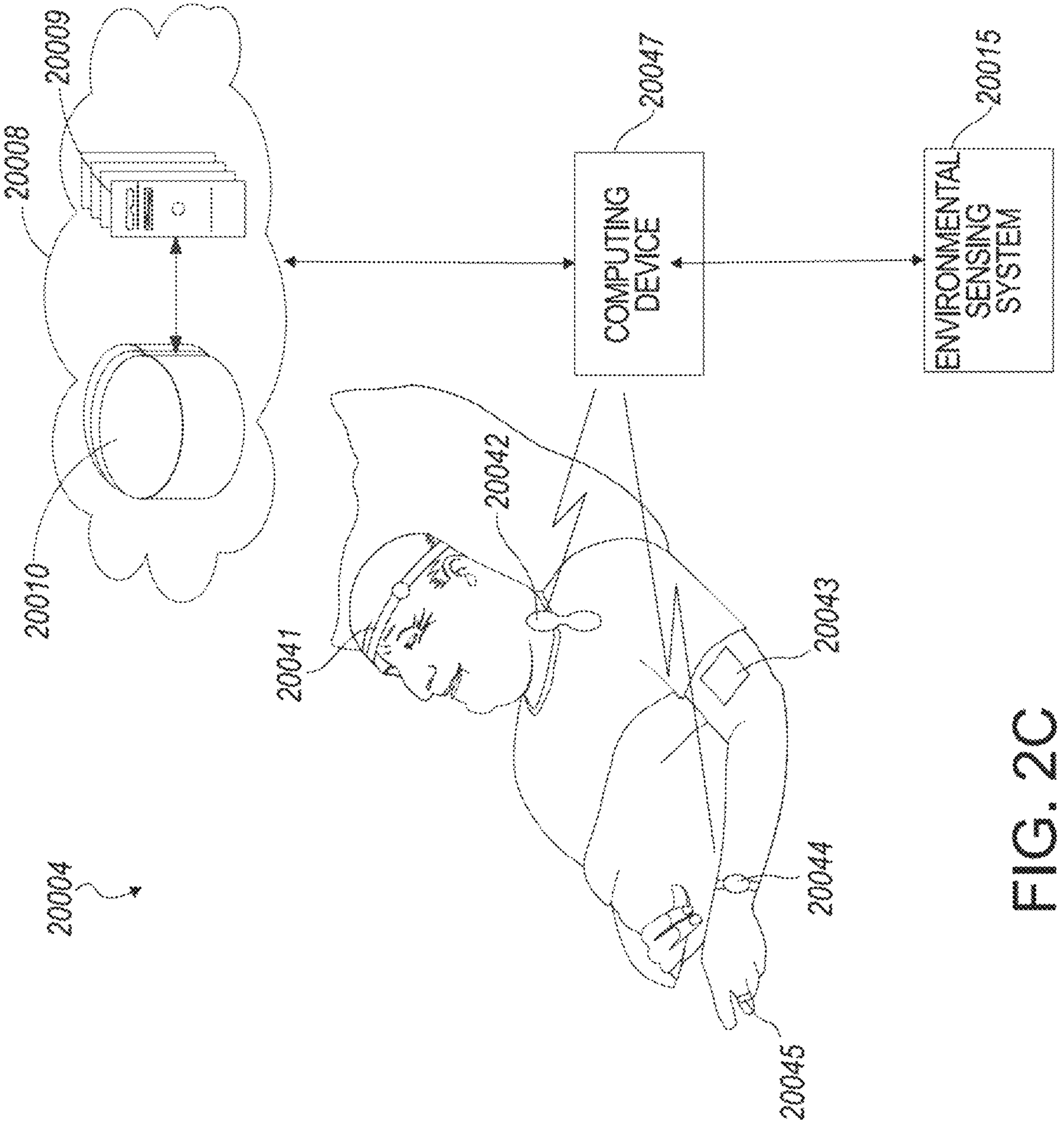
FIG. 2C shows an example of a patient monitoring system (e.g., an uncontrolled patient monitoring system).

FIG. 2C shows an example of a patient monitoring system (e.g., an uncontrolled patient monitoring system 20004). As illustrated in FIG. 2C, a patient in an uncontrolled environment (e.g., a patient's residence) is being monitored by a plurality of patient sensing systems 20041-20045. The patient sensing systems 20041-20045 may measure and/or monitor measurement data associated with one or more patient biomarkers. For example, a patient sensing system 20041, a head band, may be used to measure an electroencephalogram (EEG). Other patient sensing systems 20042, 20043, 20044, and 20045 are examples where various patient biomarkers are monitored, measured, and/or reported, as described in FIG. 2B. One or more of the patient sensing systems 20041-20045 may be send the measured data associated with the patient biomarkers being monitored to the computing device 20047, which in turn may be in communication with a remote server 20009 of the remote cloud computing system 20008. The patient sensing systems 20041-20045 may use a radio frequency (RF) link to be in communication with a computing device 20047 (e.g., a smart phone, a tablet, etc.). The patient sensing systems 20041-20045 may use one or more of the following RF protocols for communication with the computing device 20047: Bluetooth, Bluetooth Low-Energy (BLE), Bluetooth Smart, Zigbee, Z-wave, IPv6 Low-power wireless Personal Area Network (6LoWPAN), Thread, Wi-Fi, etc. In an example, the patient sensing systems 20041-20045 may be connected to the computing device 20047 via a wireless router, a wireless hub, or a wireless bridge.

The computing device 20047 may be in communication with a remote server 20009 that is part of a cloud computing system 20008. In an example, the computing device 20047 may be in communication with a remote server 20009 via an internet service provider's cable/FIOS networking node. In an example, a patient sensing system may be in direct communication with a remote server 20009. The computing device 20047 or the sensing system may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

In an example, a computing device 20047 may display information associated with a patient biomarker. For example, a computing device 20047 may display blood pressure, Oxygen saturation level, respiratory rate, etc. A computing device 20047 may display notifications for the patient or an HCP providing information about the patient, for example, information about a recovery milestone or a complication.

In an example, the computing device 20047 and/or the patient sensing system 20044 may receive a notification information from the surgical hub 20006 for displaying on a display unit of the computing device 20047 and/or the patient sensing system 20044. The notification information may include a notification about a recovery milestone or a notification about a complication, for example, in case of post-surgical recovery. The notification information may also include an actionable severity level associated with the notification. The computing device 20047 and/or the sensing system 20044 may display the notification and the actionable severity level to the patient. The patient sensing system may also alert the patient using a haptic feedback. The visual notification and/or the haptic notification may be accompanied by an audible notification prompting the patient to pay attention to the visual notification provided on the display unit of the sensing system.

Figure 3:
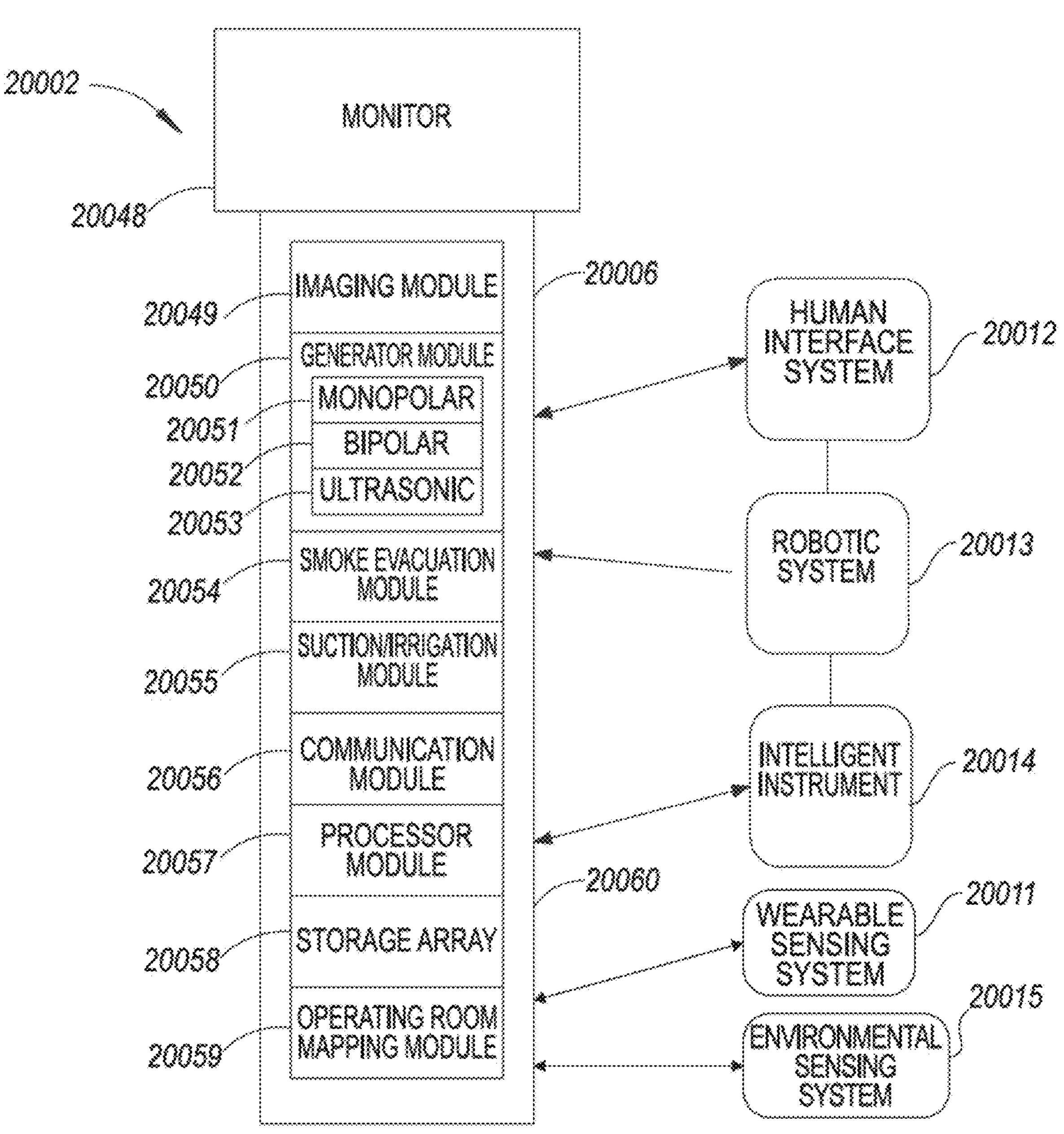
FIG. 3 illustrates an example surgical hub paired with various systems.

FIG. 3 shows an example surgeon monitoring system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be a generator module 20050 with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
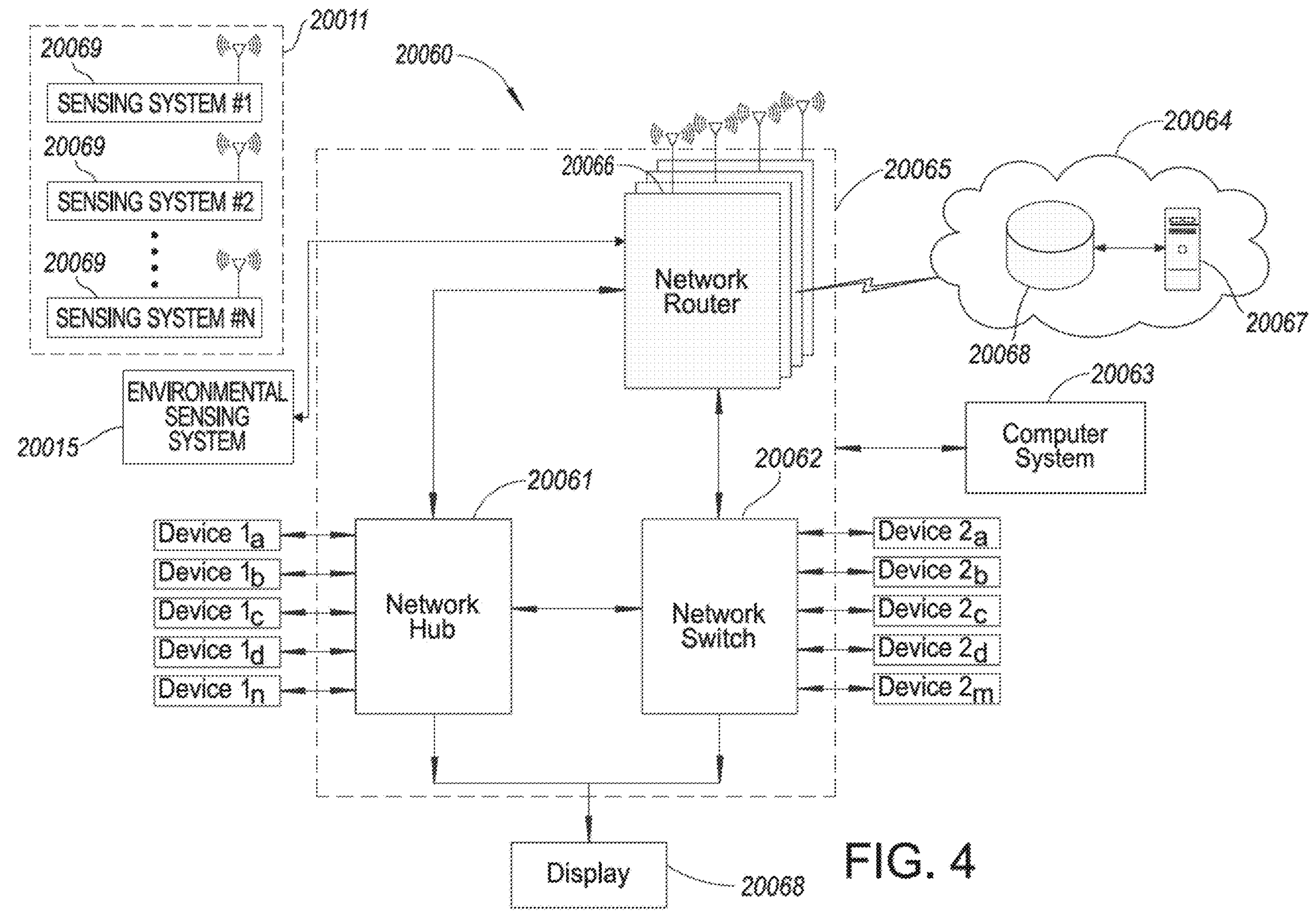
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, an environment sensing system, and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation. Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1*a*-1*n* located in the operating theater may be coupled to the modular communication hub 20065. The network hub 20061 and/or the network switch 20062 may be coupled to a network router 20066 to connect the devices 1*a*-1*n* to the cloud computing system 20064 or the local computer system 20063. Data associated with the devices 1*a*-1*n* may be transferred to cloud-based computers via the router for remote data processing and manipulation. Data associated with the devices 1*a*-1*n* may also be transferred to the local computer system 20063 for local data processing and manipulation. Modular devices 2*a*-2*m* located in the same operating theater also may be coupled to a network switch 20062. The network switch 20062 may be coupled to the network hub 20061 and/or the network router 20066 to connect the devices 2*a*-2*m* to the cloud 20064. Data associated with the devices 2*a*-2*m* may be transferred to the cloud computing system 20064 via the network router 20066 for data processing and manipulation. Data associated with the devices 2*a*-2*m* may also be transferred to the local computer system 20063 for local data processing and manipulation.

The wearable sensing system 20011 may include one or more sensing systems 20069. The sensing systems 20069 may include a surgeon sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1*a*-1*n*/2*a*-2*m*. The local computer system 20063 also may be contained in a modular control tower. The modular communication hub 20065 may be connected to a display 20068 to display images obtained by some of the devices 1*a*-1*n*/2*a*-2*m*, for example during surgical procedures. In various aspects, the devices 1*a*-1*n*/2*a*-2*m* may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1*a*-1*n*/2*a*-2*m* or the sensing systems 20069 to the cloud-base system 20064. One or more of the devices 1*a*-1*n*/2*a*-2*m* or the sensing systems 20069 coupled to the network hub 20061 or network switch 20062 may collect data or measurement data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1*a*-1*n*/2*a*-2*m* located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1*a*-1*n*/2*a*-2*m*, the surgical data network can provide improved surgical outcomes, reduced costs, and improved patient satisfaction. At least some of the devices 1*a*-1*n*/2*a*-2*m* may be employed to view tissue states to assess leaks or perfusion of sealed tissue after a tissue sealing and cutting procedure. At least some of the devices 1*a*-1*n*/2*a*-2*m* may be employed to identify pathology, such as the effects of diseases, using the cloud-based computing to examine data including images of samples of body tissue for diagnostic purposes. This may include localization and margin confirmation of tissue and phenotypes. At least some of the devices 1*a*-1*n*/2*a*-2*m* may be employed to identify anatomical structures of the body using a variety of sensors integrated with imaging devices and techniques such as overlaying images captured by multiple imaging devices. The data gathered by the devices 1*a*-1*n*/2*a*-2*m*, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, notify a patient of a complication during post-surgical period.

The operating theater devices 1*a*-1*n* may be connected to the modular communication hub 20065 over a wired channel or a wireless channel depending on the configuration of the devices 1*a*-1*n* to a network hub 20061. The network hub 20061 may be implemented, in one aspect, as a local network broadcast device that works on the physical layer of the Open System Interconnection (OSI) model. The network hub may provide connectivity to the devices 1*a*-1*n* located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1*a*-1*n* can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2*a*-2*m* may be connected to a network switch 20062 over a wired channel or a wireless channel. The network switch 20062 works in the data link layer of the OSI model. The network switch 20062 may be a multicast device for connecting the devices 2*a*-2*m* located in the same operating theater to the network. The network switch 20062 may send data in the form of frames to the network router 20066 and may work in full duplex mode. Multiple devices 2*a*-2*m* can send data at the same time through the network switch 20062. The network switch 20062 stores and uses MAC addresses of the devices 2*a*-2*m* to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1*a*-1*n*/2*a*-2*m* and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1*a*-1*n* and devices 2*a*-2*m* located in the operating theater.

In examples, the operating theater devices 1*a*-1*n*/2*a*-2*m* and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1*a*-1*n*/2*a*-2*m* and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1*a*-1*n*/2*a*-2*m* and/or the sensing systems 20069 and may handle a data type known as frames. Frames may carry the data generated by the devices 1*a*-1*n*/2*a*-2*m* and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1*a*-1*n*/2*a*-2*m*.

Figure 5:
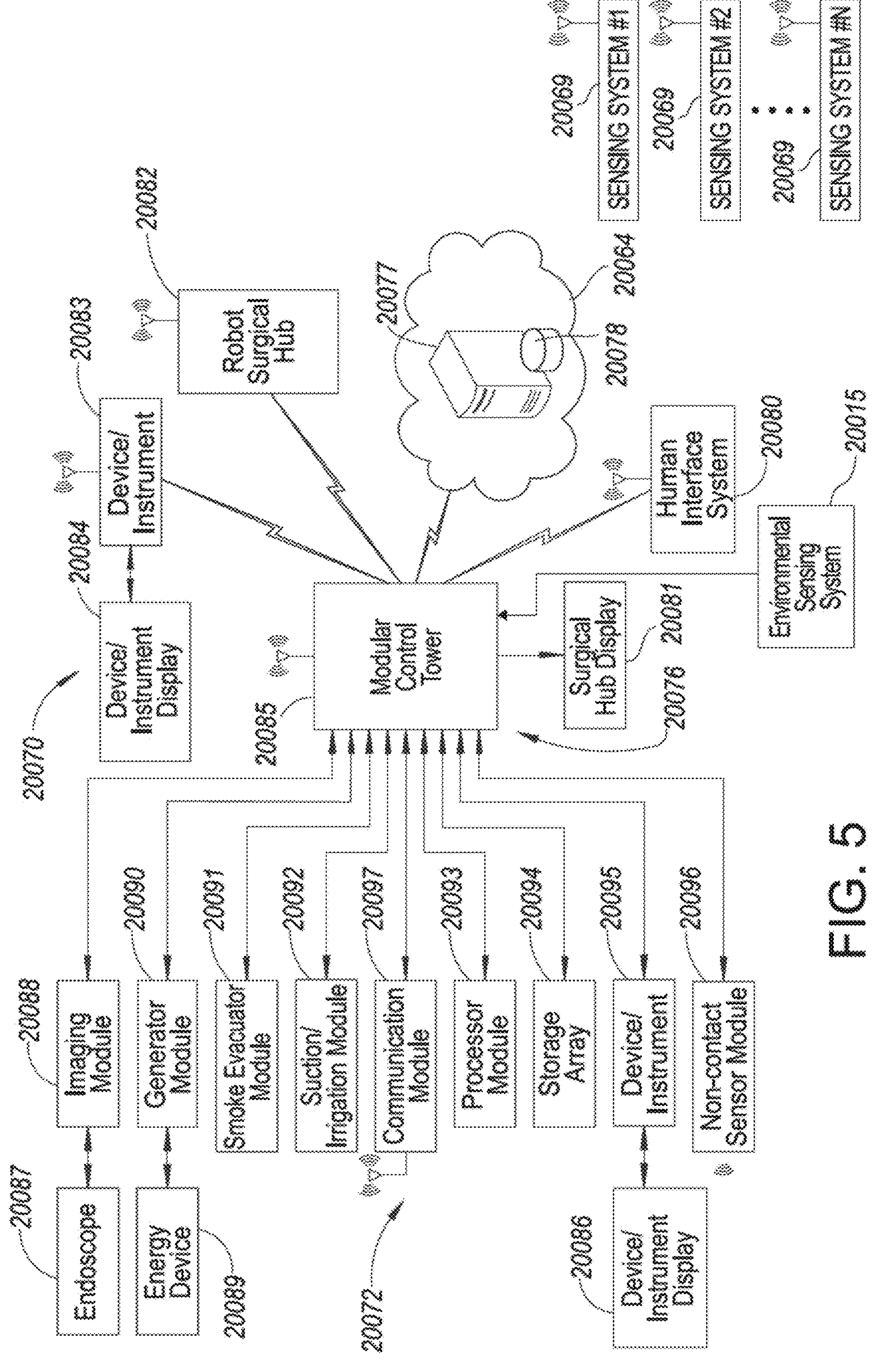
FIG. 5 illustrates an example computer-implemented interactive surgical system that may be part of a surgeon monitoring system.
Figure 6A:
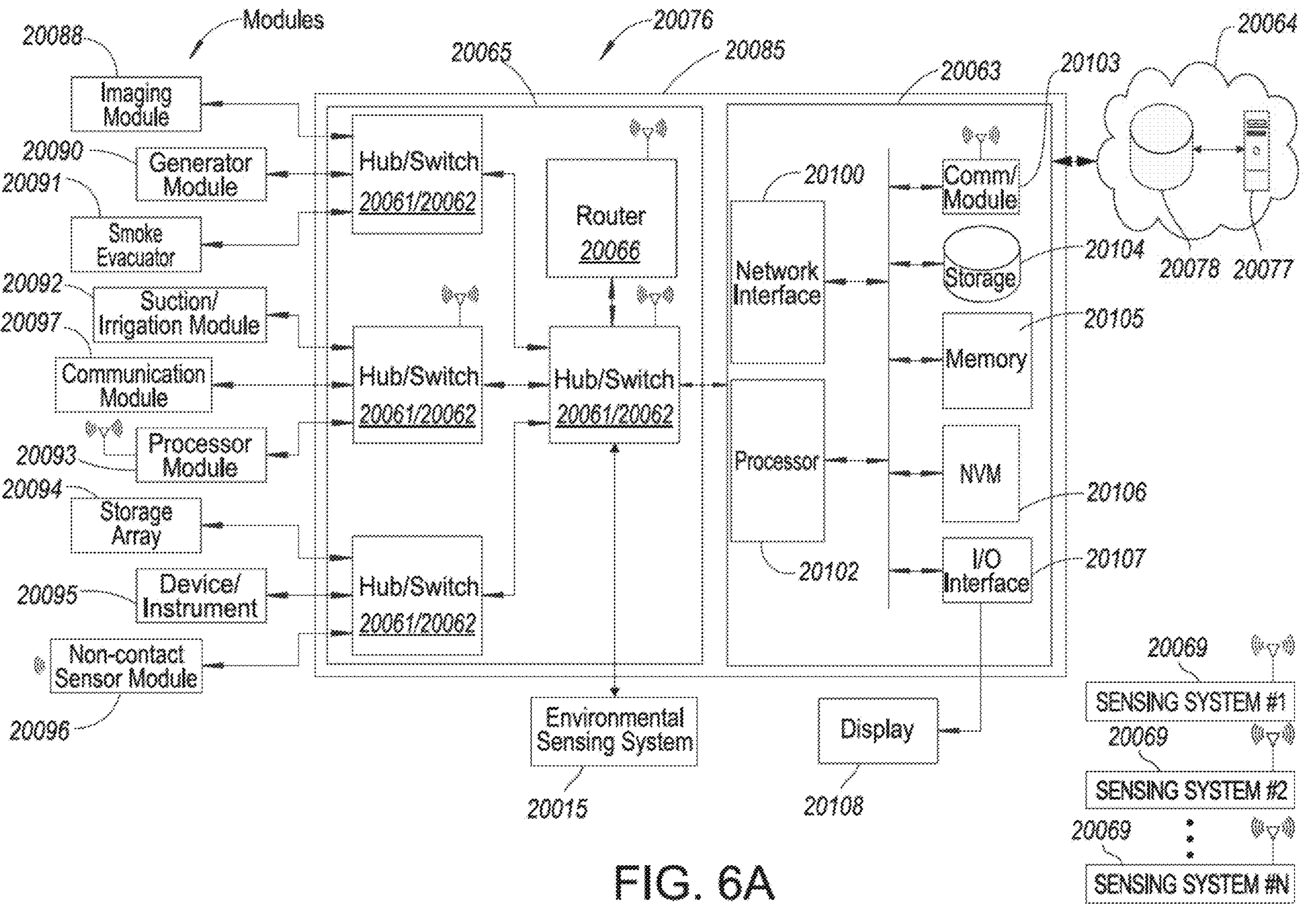
FIG. 6A illustrates a surgical hub comprising a plurality of modules coupled to a modular control tower.

FIG. 5 illustrates a computer-implemented interactive surgical system 20070 that may be a part of the surgeon monitoring system 20002. The computer-implemented interactive surgical system 20070 is similar in many respects to the surgeon sensing system 20002. For example, the computer-implemented interactive surgical system 20070 may include one or more surgical sub-systems 20072, which are similar in many respects to the surgeon monitoring systems 20002. Each sub-surgical system 20072 includes at least one surgical hub 20076 in communication with a cloud computing system 20064 that may include a remote server 20077 and a remote storage 20078. In one aspect, the computer-implemented interactive surgical system 20070 may include a modular control tower 20085 connected to multiple operating theater devices such as sensing systems (e.g., surgeon sensing systems 20002 and/or patient sensing system 20003), intelligent surgical instruments, robots, and other computerized devices located in the operating theater. As shown in FIG. 6A, the modular control tower 20085 may include a modular communication hub 20065 coupled to a local computing system 20063.

As illustrated in the example of FIG. 5, the modular control tower 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The modular control tower 20085 may also be in communication with one or more sensing systems 20069 and an environmental sensing system 20015. The sensing systems 20069 may be connected to the modular control tower 20085 either directly via a router or via the communication module 20097. The operating theater devices may be coupled to cloud computing resources and data storage via the modular control tower 20085. A robot surgical hub 20082 also may be connected to the modular control tower 20085 and to the cloud computing resources. The devices/instruments 20095 or 20084, human interface system 20080, among others, may be coupled to the modular control tower 20085 via wired or wireless communication standards or protocols, as described herein. The human interface system 20080 may include a display sub-system and a notification sub-system. The modular control tower 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control tower 20085 in conjunction with images and overlaid images.

FIG. 6A illustrates a surgical hub 20076 comprising a plurality of modules coupled to the modular control tower 20085. As shown in FIG. 6A, the surgical hub 20076 may be connected to a generator module 20090, the smoke evacuator module 20091, suction/irrigation module 20092, and the communication module 20097. The modular control tower 20085 may comprise a modular communication hub 20065, e.g., a network connectivity device, and a computer system 20063 to provide local wireless connectivity with the sensing systems, local processing, complication monitoring, visualization, and imaging, for example. As shown in FIG. 6A, the modular communication hub 20065 may be connected in a configuration (e.g., a tiered configuration) to expand a number of modules (e.g., devices) and a number of sensing systems 20069 that may be connected to the modular communication hub 20065 and transfer data associated with the modules and/or measurement data associated with the sensing systems 20069 to the computer system 20063, cloud computing resources, or both. As shown in FIG. 6A, each of the network hubs/switches 20061/20062 in the modular communication hub 20065 may include three downstream ports and one upstream port. The upstream network hub/switch may be connected to a processor 20102 to provide a communication connection to the cloud computing resources and a local display 20108. At least one of the network/hub switches 20061/20062 in the modular communication hub 20065 may have at least one wireless interface to provided communication connection between the sensing systems 20069 and/or the devices 20095 and the cloud computing system 20064. Communication to the cloud computing system 20064 may be made either through a wired or a wireless communication channel.

The surgical hub 20076 may employ a non-contact sensor module 20096 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 20063 may comprise a processor 20102 and a network interface 20100. The processor 20102 may be coupled to a communication module 20103, storage 20104, memory 20105, non-volatile memory 20106, and input/output (I/O) interface 20107 via a system bus. The system bus can be any of several types of bus structure(s) including the memory bus or memory controller, a peripheral bus or external bus, and or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 20102 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 1 analog input channels, details of which are available for the product datasheet.

In an example, the processor 20102 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during startup, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 20063 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface 20107. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

Figure 6B:
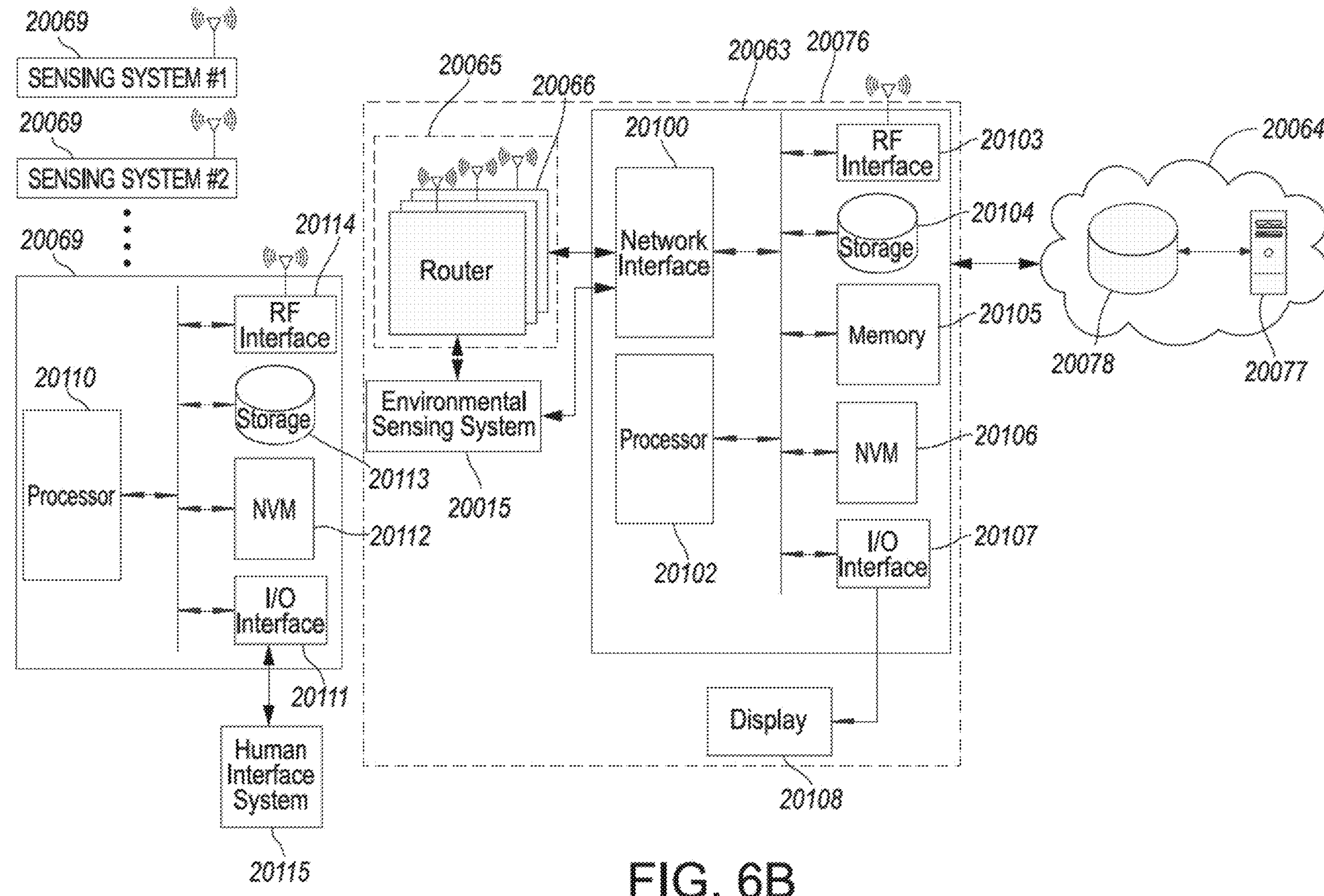
FIG. 6B illustrates an example of a controlled patient monitoring system.

In various examples, the computer system 20063 of FIG. 4, FIG. 6A and FIG. 6B, the imaging module 20088 and/or human interface system 20080, and/or the processor module 20093 of FIG. 5 and FIG. 6A may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

FIG. 6B illustrates an example of a wearable monitoring system, e.g., a controlled patient monitoring system. A controlled patient monitoring system may be the sensing system used to monitor a set of patient biomarkers when the patient is at a healthcare facility. The controlled patient monitoring system may be deployed for pre-surgical patient monitoring when a patient is being prepared for a surgical procedure, in-surgical monitoring when a patient is being operated on, or in post-surgical monitoring, for example, when a patient is recovering, etc. As illustrated in FIG. 6B, a controlled patient monitoring system may include a surgical hub system 20076, which may include one or more routers 20066 of the modular communication hub 20065 and a computer system 20063. The routers 20065 may include wireless routers, wired switches, wired routers, wired or wireless networking hubs, etc. In an example, the routers 20065 may be part of the infrastructure. The computing system 20063 may provide local processing for monitoring various biomarkers associated with a patient or a surgeon, and a notification mechanism to indicate to the patient and/or a healthcare provided (HCP) that a milestone (e.g., a recovery milestone) is met or a complication is detected. The computing system 20063 of the surgical hub system 20076 may also be used to generate a severity level associated with the notification, for example, a notification that a complication has been detected.

Figure 6C:
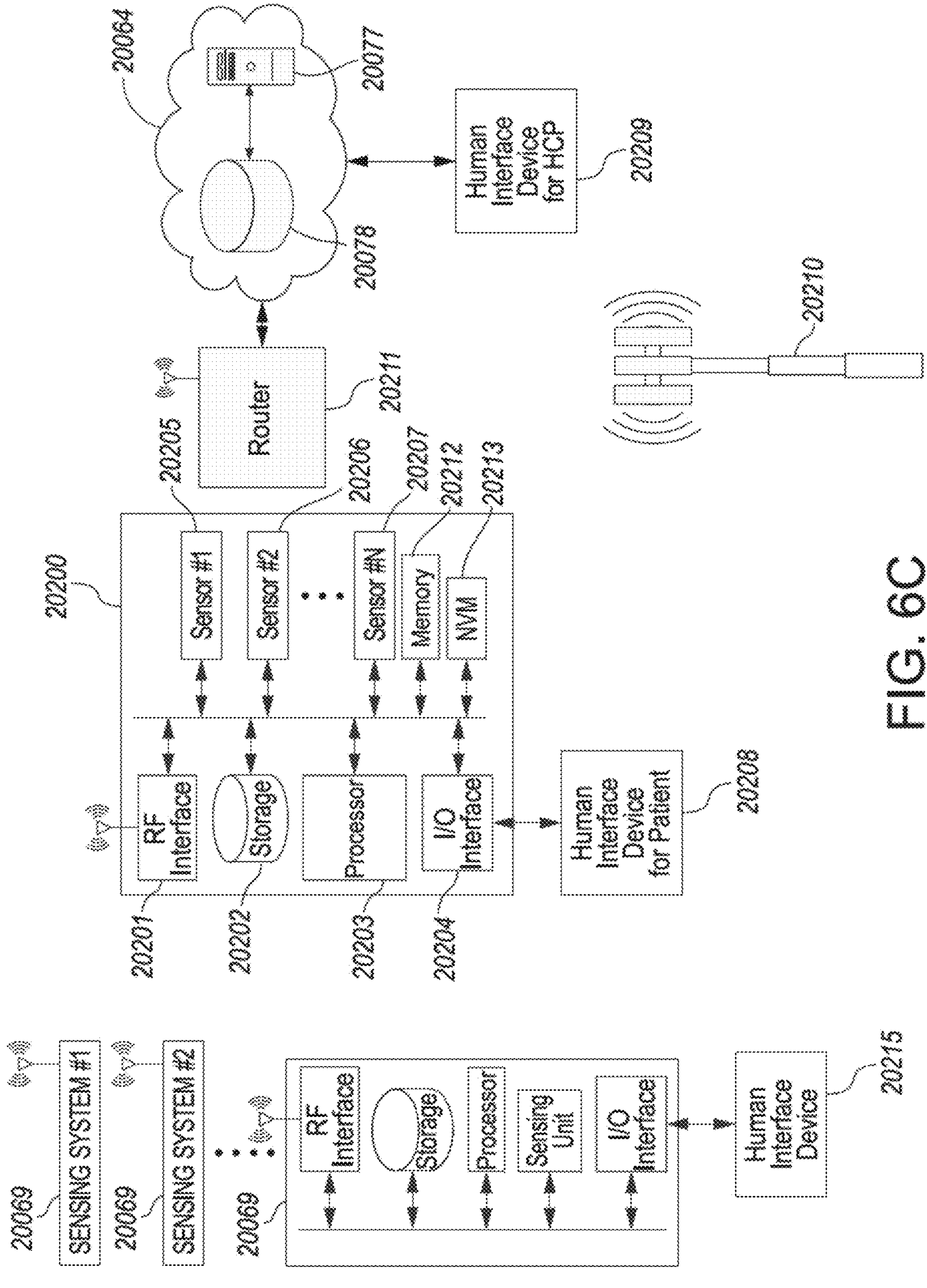
FIG. 6C illustrates an example of an uncontrolled patient monitoring system.
Figure 7A:
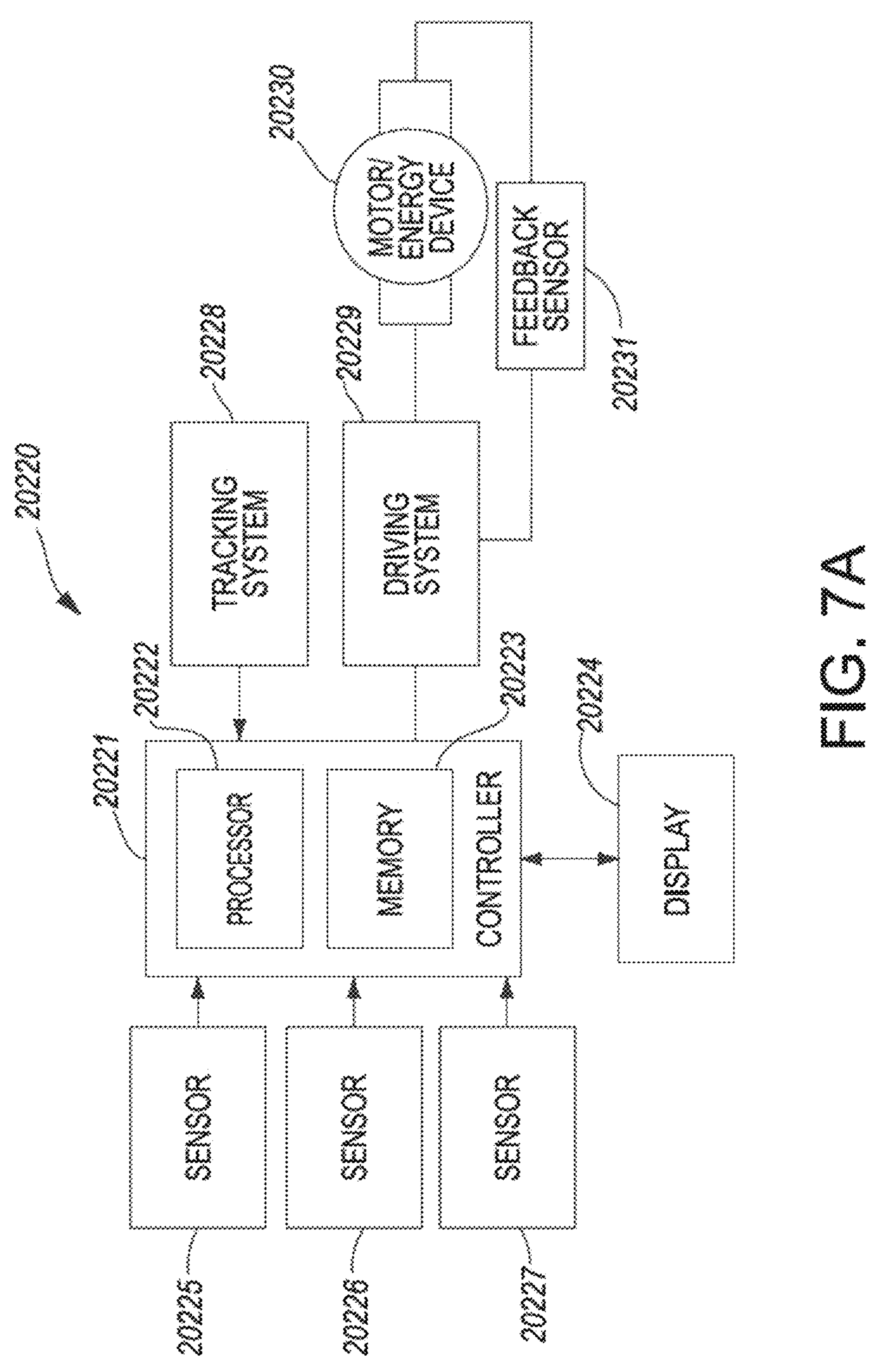
FIG. 7A illustrates a logic diagram of a control system of a surgical instrument or a tool.
Figure 7B:
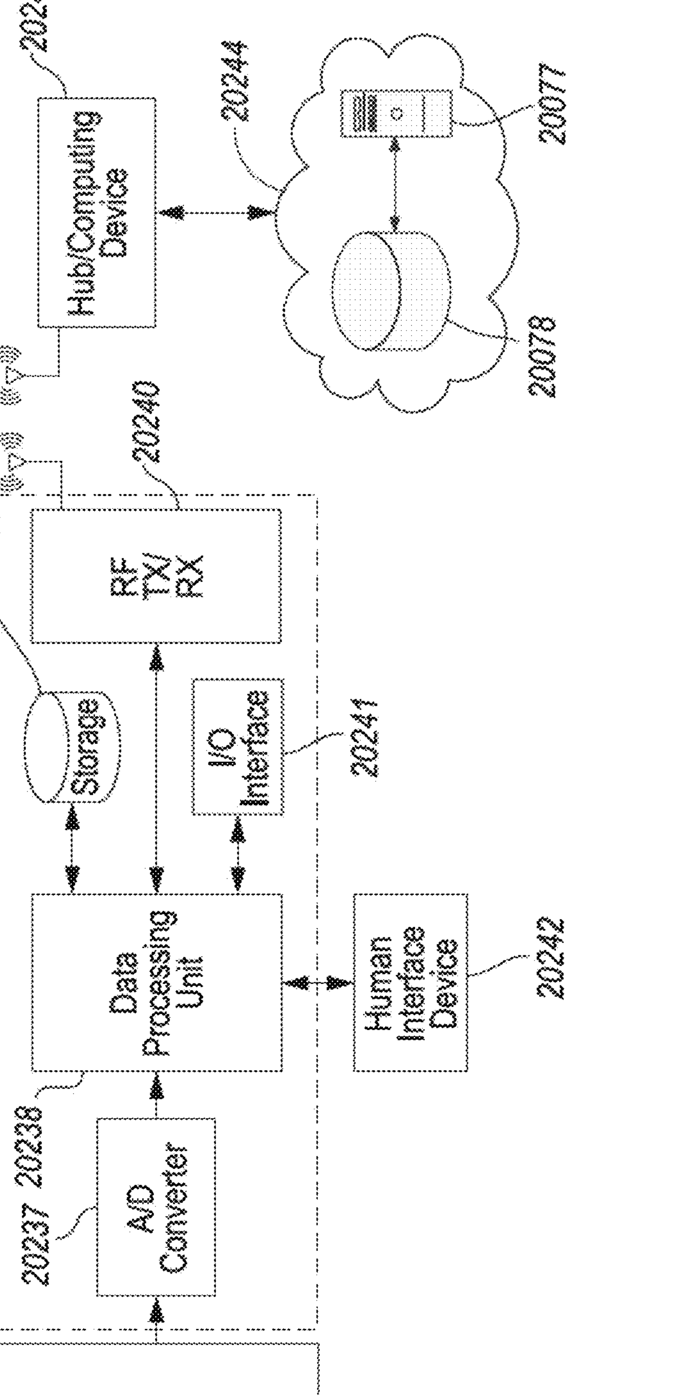
FIG. 7B shows an exemplary sensing system with a sensor unit and a data processing and communication unit.
Figure 7C:
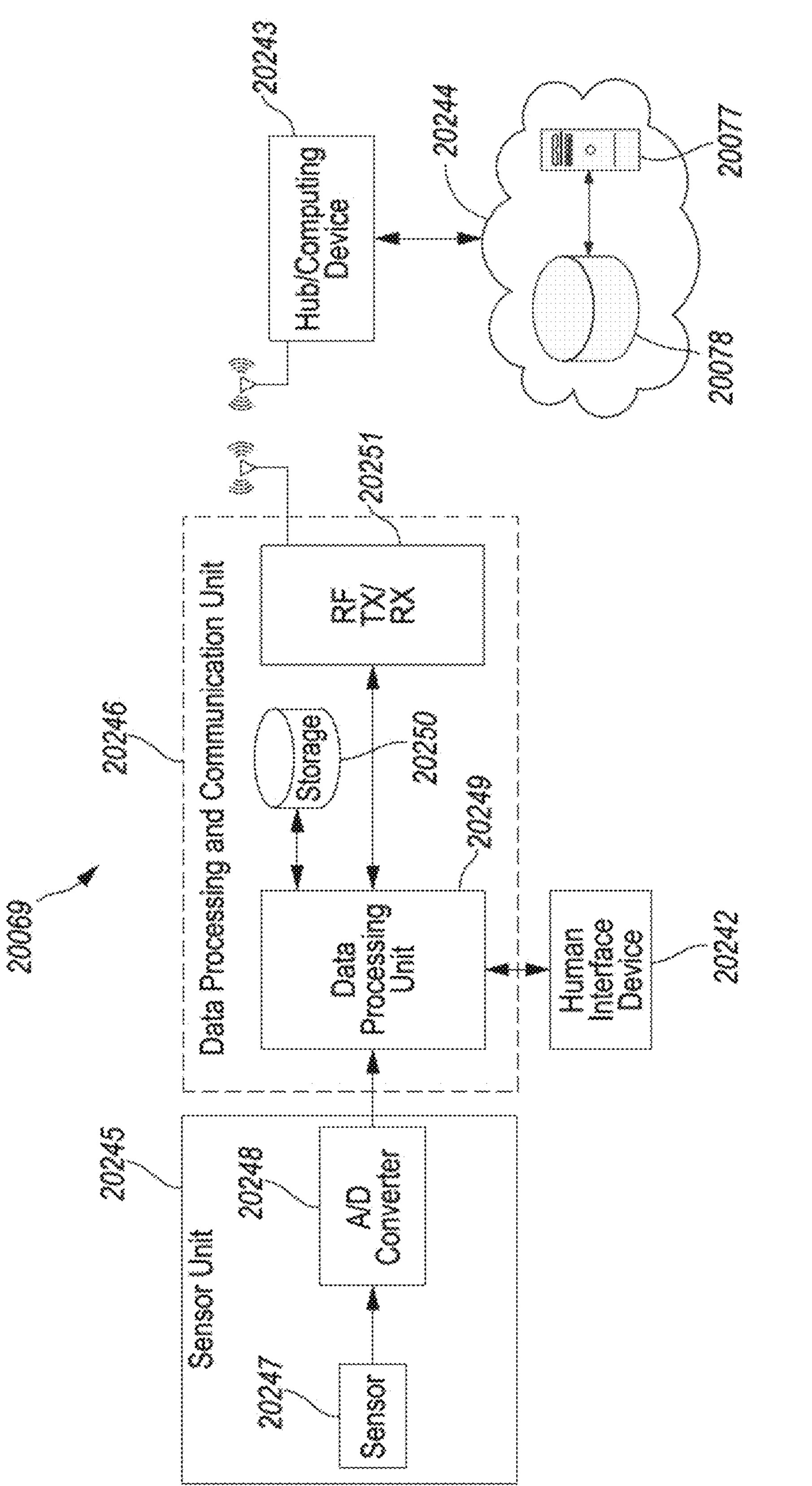
FIG. 7C shows an exemplary sensing system with a sensor unit and a data processing and communication unit.
Figure 7D:
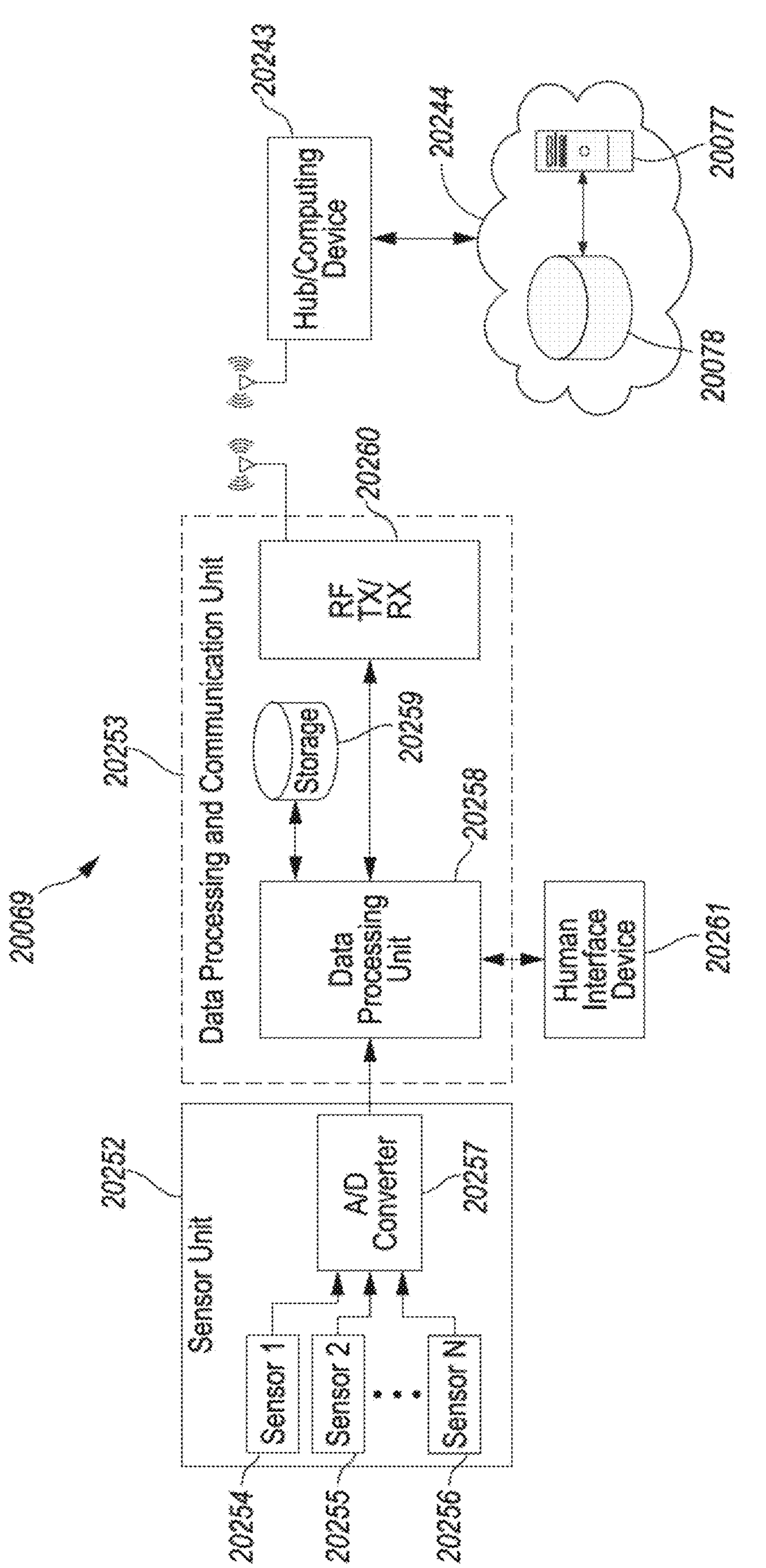
FIG. 7D shows an exemplary sensing system with a sensor unit and a data processing and communication unit.

The computing system 20063 of FIG. 4, FIG. 6B, the computing device 20200 of FIG. 6C, the hub/computing device 20243 of FIG. 7B, FIG. 7C, or FIG. 7D may be a surgical computing system or a hub device, a laptop, a tablet, a smart phone, etc.

As shown in FIG. 6B, a set of sensing systems 20069 and/or an environmental sensing system 20015 (as described in FIG. 2A) may be connected to the surgical hub system 20076 via the routers 20065. The routers 20065 may also provide a direct communication connection between the sensing systems 20069 and the cloud computing system 20064, for example, without involving the local computer system 20063 of the surgical hub system 20076. Communication from the surgical hub system 20076 to the cloud 20064 may be made either through a wired or a wireless communication channel.

As shown in FIG. 6B, the computer system 20063 may include a processor 20102 and a network interface 20100. The processor 20102 may be coupled to a radio frequency (RF) interface or a communication module 20103, storage 20104, memory 20105, non-volatile memory 20106, and input/output interface 20107 via a system bus, as described in FIG. 6A. The computer system 20063 may be connected with a local display unit 20108. In some examples, the display unit 20108 may be replaced by a HID. Details about the hardware and software components of the computer system are provided in FIG. 6A.

As shown in FIG. 6B, a sensing system 20069 may include a processor 20110. The processor 20110 may be coupled to a radio frequency (RF) interface 20114, storage 20113, memory (e.g., a non-volatile memory) 20112, and I/O interface 20111 via a system bus. The system bus can be any of several types of bus structure(s) including the memory bus or memory controller, a peripheral bus or external bus, and/or a local bus, as described herein. The processor 20110 may be any single-core or multicore processor as described herein.

It is to be appreciated that the sensing system 20069 may include software that acts as an intermediary between sensing system users and the computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

The sensing system 20069 may be connected to a human interface system 20115. The human interface system 20115 may be a touch screen display. The human interface system 20115 may include a human interface display for displaying information associated with a surgeon biomarker and/or a patient biomarker, display a prompt for a user action by a patient or a surgeon, or display a notification to a patient or a surgeon indicating information about a recovery millstone or a complication. The human interface system 20115 may be used to receive input from a patient or a surgeon. Other human interface systems may be connected to the sensing system 20069 via the I/O interface 20111. For example, the human interface device 20115 may include devices for providing a haptic feedback as a mechanism for prompting a user to pay attention to a notification that may be displayed on a display unit.

The sensing system 20069 may operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. The remote computer(s) may be logically connected to the computer system through a network interface. The network interface may encompass communication networks such as local area networks (LANs), wide area networks (WANs), and/or mobile networks. LAN technologies may include Fiber Distributed Data Interface (FDDI), Copper Distributed Data Interface (CDDI), Ethernet/IEEE 802.3, Token Ring/IEEE 802.5, Wi-Fi/IEEE 802.11, and the like. WAN technologies may include, but are not limited to, point-to-point links, circuit-switching networks like Integrated Services Digital Networks (ISDN) and variations thereon, packet-switching networks, and Digital Subscriber Lines (DSL). The mobile networks may include communication links based on one or more of the following mobile communication protocols: GSM/GPRS/EDGE (2G), UMTS/HSPA (3G), long term evolution (LTE) or 4G, LTE-Advanced (LTE-A), new radio (NR) or 5G, etc.

FIG. 6C illustrates an exemplary uncontrolled patient monitoring system, for example, when the patient is away from a healthcare facility. The uncontrolled patient monitoring system may be used for pre-surgical patient monitoring when a patient is being prepared for a surgical procedure but is away from a healthcare facility, or in post-surgical monitoring, for example, when a patient is recovering away from a healthcare facility.

As illustrated in FIG. 6C, one or more sensing systems 20069 are in communication with a computing device 20200, for example, a personal computer, a laptop, a tablet, or a smart phone. The computing system 20200 may provide processing for monitoring of various biomarkers associated with a patient, a notification mechanism to indicate that a milestone (e.g., a recovery milestone) is met or a complication is detected. The computing system 20200 may also provide instructions for the user of the sensing system to follow. The communication between the sensing systems 20069 and the computing device 20200 may be established directly using a wireless protocol as described herein or via the wireless router/hub 20211.

As shown in FIG. 6C, the sensing systems 20069 may be connected to the computing device 20200 via router 20211. The router 20211 may include wireless routers, wired switches, wired routers, wired or wireless networking hubs, etc. The router 20211 may provide a direct communication connection between the sensing systems 20069 and the cloud servers 20064, for example, without involving the local computing device 20200. The computing device 20200 may be in communication with the cloud server 20064. For example, the computing device 20200 may be in communication with the cloud 20064 through a wired or a wireless communication channel. In an example, a sensing system 20069 may be in communication with the cloud directly over a cellular network, for example, via a cellular base station 20210.

As shown in FIG. 6C, the computing device 20200 may include a processor 20203 and a network or an RF interface 20201. The processor 20203 may be coupled to a storage 20202, memory 20212, non-volatile memory 20213, and input/output interface 20204 via a system bus, as described in FIG. 6A and FIG. 6B. Details about the hardware and software components of the computer system are provided in FIG. 6A. The computing device 20200 may include a set of sensors, for example, sensor #1 20205, sensor #2 20206 up to sensor #n 20207. These sensors may be a part of the computing device 20200 and may be used to measure one or more attributes associated with the patient. The attributes may provide a context about a biomarker measurement performed by one of the sensing systems 20069. For example, sensor #1 may be an accelerometer that may be used to measure acceleration forces in order to sense movement or vibrations associated with the patient. In an example, the sensors 20205 to 20207 may include one or more of: a pressure sensor, an altimeter, a thermometer, a lidar, or the like.

As shown in FIG. 6B, a sensing system 20069 may include a processor, a radio frequency interface, a storage, a memory or non-volatile memory, and input/output interface via a system bus, as described in FIG. 6A. The sensing system may include a sensor unit and a processing and communication unit, as described in FIG. 7B through 7D. The system bus can be any of several types of bus structure(s) including the memory bus or memory controller, a peripheral bus or external bus, and/or a local bus, as described herein. The processor may be any single-core or multicore processor, as described herein.

The sensing system 20069 may be in communication with a human interface system 20215. The human interface system 20215 may be a touch screen display. The human interface system 20215 may be used to display information associated with a patient biomarker, display a prompt for a user action by a patient, or display a notification to a patient indicating information about a recovery millstone or a complication. The human interface system 20215 may be used to receive input from a patient. Other human interface systems may be connected to the sensing system 20069 via the I/O interface. For example, the human interface system may include devices for providing a haptic feedback as a mechanism for prompting a user to pay attention to a notification that may be displayed on a display unit. The sensing system 20069 may operate in a networked environment using logical connections to one or more remote computers, such as cloud computer(s), or local computers, as described in FIG. 6B.

FIG. 7A illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

In one aspect, the microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with Stellaris Ware® software, a 2 KB EEPROM, one or more PWM modules, one or more QEI analogs, and/or one or more 12-bit ADCs with 1 analog input channels, details of which are available for the product datasheet.

In one aspect, the microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

In one form, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5 and FIG. 6A.

FIG. 7B shows an example sensing system 20069. The sensing system may be a surgeon sensing system or a patient sensing system. The sensing system 20069 may include a sensor unit 20235 and a human interface system 20242 that are in communication with a data processing and communication unit 20236. The data processing and communication unit 20236 may include an analog-to-digital converted 20237, a data processing unit 20238, a storage unit 20239, and an input/output interface 20241, a transceiver 20240. The sensing system 20069 may be in communication with a surgical hub or a computing device 20243, which in turn is in communication with a cloud computing system 20244. The cloud computing system 20244 may include a cloud storage system 20078 and one or more cloud servers 20077.

The sensor unit 20235 may include one or more ex vivo or in vivo sensors for measuring one or more biomarkers. The biomarkers may include, for example, Blood pH, hydration state, oxygen saturation, core body temperature, heart rate, Heart rate variability, Sweat rate, Skin conductance, Blood pressure, Light exposure, Environmental temperature, Respiratory rate, Coughing and sneezing, Gastrointestinal motility, Gastrointestinal tract imaging, Tissue perfusion pressure, Bacteria in respiratory tract, Alcohol consumption, Lactate (sweat), Peripheral temperature, Positivity and optimism, Adrenaline (sweat), Cortisol (sweat), Edema, Mycotoxins, VO2 max, Pre-operative pain, chemicals in the air, Circulating tumor cells, Stress and anxiety, Confusion and delirium, Physical activity, Autonomic tone, Circadian rhythm, Menstrual cycle, Sleep, etc. These biomarkers may be measured using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The sensors may measure the biomarkers as described herein using one of more of the following sensing technologies: photoplethysmography, electrocardiography, electroencephalography, colorimetry, impedimentary, potentiometry, amperometry, etc.

As illustrated in FIG. 7B, a sensor in the sensor unit 20235 may measure a physiological signal (e.g., a voltage, a current, a PPG signal, etc.) associated with a biomarker to be measured. The physiological signal to be measured may depend on the sensing technology used, as described herein. The sensor unit 20235 of the sensing system 20069 may be in communication with the data processing and communication unit 20236. In an example, the sensor unit 20235 may communicate with the data processing and communication unit 20236 using a wireless interface. The data processing and communication unit 20236 may include an analog-to-digital converter (ADC) 20237, a data processing unit 20238, a storage 20239, an I/O interface 20241, and an RF transceiver 20240. The data processing unit 20238 may include a processor and a memory unit.

The sensor unit 20235 may transmit the measured physiological signal to the ADC 20237 of the data processing and communication unit 20236. In an example, the measured physiological signal may be passed through one or more filters (e.g., an RC low-pass filter) before being sent to the ADC. The ADC may convert the measured physiological signal into measurement data associated with the biomarker. The ADC may pass measurement data to the data processing unit 20238 for processing. In an example, the data processing unit 20238 may send the measurement data associated with the biomarker to a surgical hub or a computing device 20243, which in turn may send the measurement data to a cloud computing system 20244 for further processing. The data processing unit may send the measurement data to the surgical hub or the computing device 20243 using one of the wireless protocols, as described herein. In an example, the data processing unit 20238 may first process the raw measurement data received from the sensor unit and send the processed measurement data to the surgical hub or a computing device 20243.

In an example, the data processing and communication unit 20236 of the sensing system 20069 may receive a threshold value associated with a biomarker for monitoring from a surgical hub, a computing device 20243, or directly from a cloud server 20077 of the cloud computing system 20244. The data processing unit 20236 may compare the measurement data associated with the biomarker to be monitored with the corresponding threshold value received from the surgical hub, the computing device 20243, or the cloud server 20077. The data processing and communication unit 20236 may send a notification message to the HID 20242 indicating that a measurement data value has crossed the threshold value. The notification message may include the measurement data associated with the monitored biomarker. The data processing and computing unit 20236 may send a notification via a transmission to a surgical hub or a computing device 20243 using one of the following RF protocols: Bluetooth, Bluetooth Low-Energy (BLE), Bluetooth Smart, Zigbee, Z-wave, IPv6 Low-power wireless Personal Area Network (6LoWPAN), Wi-Fi. The data processing unit 20238 may send a notification (e.g., a notification for an HCP) directly to a cloud server via a transmission to a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G. In an example, the sensing unit may be in communication with the hub/computing device via a router, as described in FIG. 6A through FIG. 6C.

FIG. 7C shows an example sensing system 20069 (e.g., a surgeon sensing system or a patient sensing system). The sensing system 20069 may include a sensor unit 20245, a data processing and communication unit 20246, and a human interface device 20242. The sensor unit 20245 may include a sensor 20247 and an analog-to-digital converted (ADC) 20248. The ADC 20248 in the sensor unit 20245 may convert a physiological signal measured by the sensor 20247 into measurement data associated with a biomarker. The sensor unit 20245 may send the measurement data to the data processing and communication unit 20246 for further processing. In an example, the sensor unit 20245 may send the measurement data to the data processing and communication unit 20246 using an inter-integrated circuit (I2C) interface.

The data processing and communication unit 20246 includes a data processing unit 20249, a storage unit 20250, and an RF transceiver 20251. The sensing system may be in communication with a surgical hub or a computing device 20243, which in turn may be in communication with a cloud computing system 20244. The cloud computing system 20244 may include a remote server 20077 and an associated remote storage 20078. The sensor unit 20245 may include one or more ex vivo or in vivo sensors for measuring one or more biomarkers, as described herein.

The data processing and communication unit 20246 after processing the measurement data received from the sensor unit 20245 may further process the measurement data and/or send the measurement data to the smart hub or the computing device 20243, as described in FIG. 7B. In an example, the data processing and communication unit 20246 may send the measurement data received from the sensor unit 20245 to the remote server 20077 of the cloud computing system 20244 for further processing and/or monitoring.

FIG. 7D shows an example sensing system 20069 (e.g., a surgeon sensing system or a patient sensing system). The sensing system 20069 may include a sensor unit 20252, a data processing and communication unit 20253, and a human interface system 20261. The sensor unit 20252 may include a plurality of sensors 20254, 20255 up to 20256 to measure one or more physiological signals associated with a patient or surgeon's biomarkers and/or one or more physical state signals associated with physical state of a patient or a surgeon. The sensor unit 20252 may also include one or more analog-to-digital converter(s) (ADCs) 20257. A list of biomarkers may include biomarkers such as those biomarkers disclosed herein. The ADC(s) 20257 in the sensor unit 20252 may convert each of the physiological signals and/or physical state signals measured by the sensors 20254-20256 into respective measurement data. The sensor unit 20252 may send the measurement data associated with one or more biomarkers as well as with the physical state of a patient or a surgeon to the data processing and communication unit 20253 for further processing. The sensor unit 20252 may send the measurement data to the data processing and communication unit 20253 individually for each of the sensors Sensor 1 20254 to Sensor N 20256 or combined for all the sensors. In an example, the sensor unit 20252 may send the measurement data to the data processing and communication unit 20253 via an I2C interface.

The data processing and communication unit 20253 may include a data processing unit 20258, a storage unit 20259, and an RF transceiver 20260. The sensing system 20069 may be in communication with a surgical hub or a computing device 20243, which in turn is in communication with a cloud computing system 20244 comprising at least one remote server 20077 and at least one storage unit 20078. The sensor units 20252 may include one or more ex vivo or in vivo sensors for measuring one or more biomarkers, as described herein.

Figure 8:
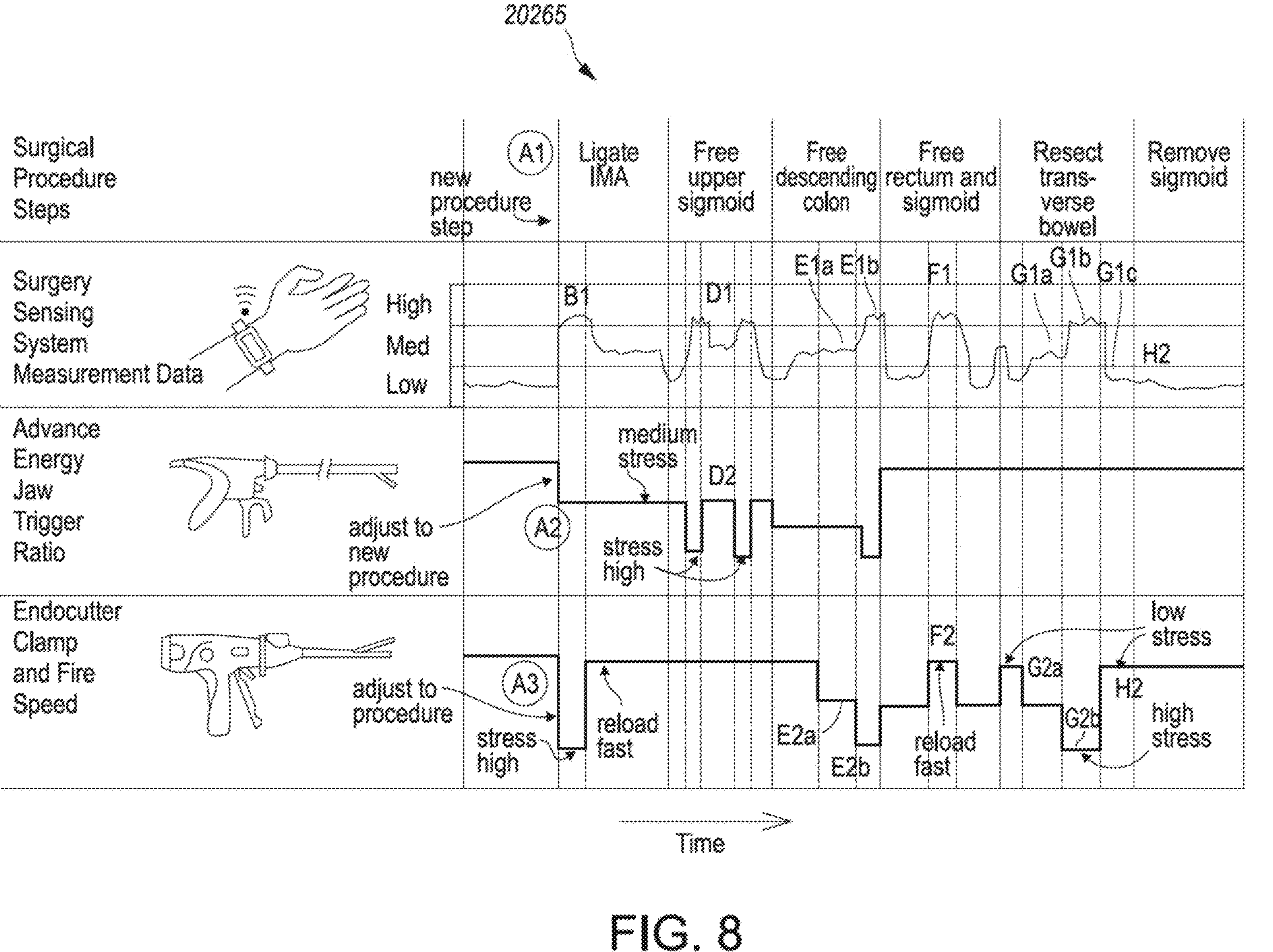
FIG. 8 illustrates an exemplary timeline of an illustrative surgical procedure indicating adjusting operational parameters of a surgical device based on a surgeon biomarker level.

FIG. 8 is an example of using a surgical task situational awareness and measurement data from one or more surgeon sensing systems to adjust surgical instrument controls. FIG. 8 illustrates a timeline 20265 of an illustrative surgical procedure and the contextual information that a surgical hub can derive from data received from one or more surgical devices, one or more surgeon sensing systems, and/or one or more environmental sensing systems at each step in the surgical procedure. The devices that could be controlled by a surgical hub may include advanced energy devices, endocutter clamps, etc. The surgeon sensing systems may include sensing systems for measuring one or more biomarkers associated with the surgeon, for example, heart rate, sweat composition, respiratory rate, etc. The environmental sensing system may include systems for measuring one or more of the environmental attributes, for example, cameras for detecting a surgeon's position/movements/breathing pattern, spatial microphones, for example to measure ambient noise in the surgical theater and/or the tone of voice of a healthcare provider, temperature/humidity of the surroundings, etc.

In the following description of the timeline 20265 illustrated in FIG. 8, reference should also be made to FIG. 5. FIG. 5 provides various components used in a surgical procedure. The timeline 20265 depicts the steps that may be taken individually and/or collectively by the nurses, surgeons, and other medical personnel during the course of an exemplary colorectal surgical procedure. In a colorectal surgical procedure, a situationally aware surgical hub 20076 may receive data from various data sources throughout the course of the surgical procedure, including data generated each time a healthcare provider (HCP) utilizes a modular device/instrument 20095 that is paired with the surgical hub 20076. The surgical hub 20076 may receive this data from the paired modular devices 20095. The surgical hub may receive measurement data from sensing systems 20069. The surgical hub may use the data from the modular device/instruments 20095 and/or measurement data from the sensing systems 20069 to continually derive inferences (i.e., contextual information) about an HCP's stress level and the ongoing procedure as new data is received, such that the stress level of the surgeon relative to the step of the procedure that is being performed is obtained. The situational awareness system of the surgical hub 20076 may perform one or more of the following: record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the FOV of the medical imaging device, change the energy level of an ultrasonic surgical instrument or RF electrosurgical instrument), or take any other such action described herein. In an example, these steps may be performed by a remote server 20077 of a cloud system 20064 and communicated with the surgical hub 20076.

As a first step (not shown in FIG. 8 for brevity), the hospital staff members may retrieve the patient's EMR from the hospital's EMR database. Based on select patient data in the EMR, the surgical hub 20076 may determine that the procedure to be performed is a colorectal procedure. The staff members may scan the incoming medical supplies for the procedure. The surgical hub 20076 may cross-reference the scanned supplies with a list of supplies that can be utilized in various types of procedures and confirms that the mix of supplies corresponds to a colorectal procedure. The surgical hub 20076 may pair each of the sensing systems 20069 worn by different HCPs.

Once each of the devices is ready and pre-surgical preparation is complete, the surgical team may begin by making incisions and place trocars. The surgical team may perform access and prep by dissecting adhesions, if any, and identifying inferior mesenteric artery (IMA) branches. The surgical hub 20076 can infer that the surgeon is in the process of dissecting adhesions, at least based on the data it may receive from the RF or ultrasonic generator indicating that an energy instrument is being fired. The surgical hub 20076 may cross-reference the received data with the retrieved steps of the surgical procedure to determine that an energy instrument being fired at this point in the process (e.g., after the completion of the previously discussed steps of the procedure) corresponds to the dissection step.

After dissection, the HCP may proceed to the ligation step (e.g., indicated by A1) of the procedure. As illustrated in FIG. 8, the HCP may begin by ligating the IMA. The surgical hub 20076 may infer that the surgeon is ligating arteries and veins because it may receive data from the advanced energy jaw device and/or the endocutter indicating that the instrument is being fired. The surgical hub may also receive measurement data from one of the HCP's sensing systems indicating higher stress level of the HCP (e.g., indicated by B1 mark on the time axis). For example, higher stress level may be indicated by change in the HCP's heart rate from a base value. The surgical hub 20076, like the prior step, may derive this inference by cross-referencing the receipt of data from the surgical stapling and cutting instrument with the retrieved steps in the process (e.g., as indicated by A2 and A3). The surgical hub 20076 may monitor the advance energy jaw trigger ratio and/or the endocutter clamp and firing speed during the high stress time periods. In an example, the surgical hub 20076 may send an assistance control signal to the advanced energy jaw device and/or the endocutter device to control the device in operation. The surgical hub may send the assistance signal based on the stress level of the HCP that is operating the surgical device and/or situational awareness known to the surgical hub. For example, the surgical hub 20076 may send control assistance signals to an advanced energy device or an endocutter clamp, as indicated in FIG. 8 by A2 and A3.

The HCP may proceed to the next step of freeing the upper sigmoid followed by freeing descending colon, rectum, and sigmoid. The surgical hub 20076 may continue to monitor the high stress markers of the HCP (e.g., as indicated by D1, E1a, E1b, F1). The surgical hub 20076 may send assistance signals to the advanced energy jaw device and/or the endocutter device during the high stress time periods, as illustrated in FIG. 8.

After mobilizing the colon, the HCP may proceed with the segmentectomy portion of the procedure. For example, the surgical hub 20076 may infer that the HCP is transecting the bowel and sigmoid removal based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. It should be noted that surgeons regularly switch back and forth between surgical stapling/cutting instruments and surgical energy (e.g., RF or ultrasonic) instruments depending upon the step in the procedure because different instruments are better adapted for particular tasks. Therefore, the sequence in which the stapling/cutting instruments and surgical energy instruments are used can indicate what step of the procedure the surgeon is performing.

The surgical hub may determine and send a control signal to surgical device based on the stress level of the HCP. For example, during time period G1b, a control signal G2b may be sent to an endocutter clamp. Upon removal of the sigmoid, the incisions are closed, and the post-operative portion of the procedure may begin. The patient's anesthesia can be reversed. The surgical hub 20076 may infer that the patient is emerging from the anesthesia based on one or more sensing systems attached to the patient.

Figure 9:
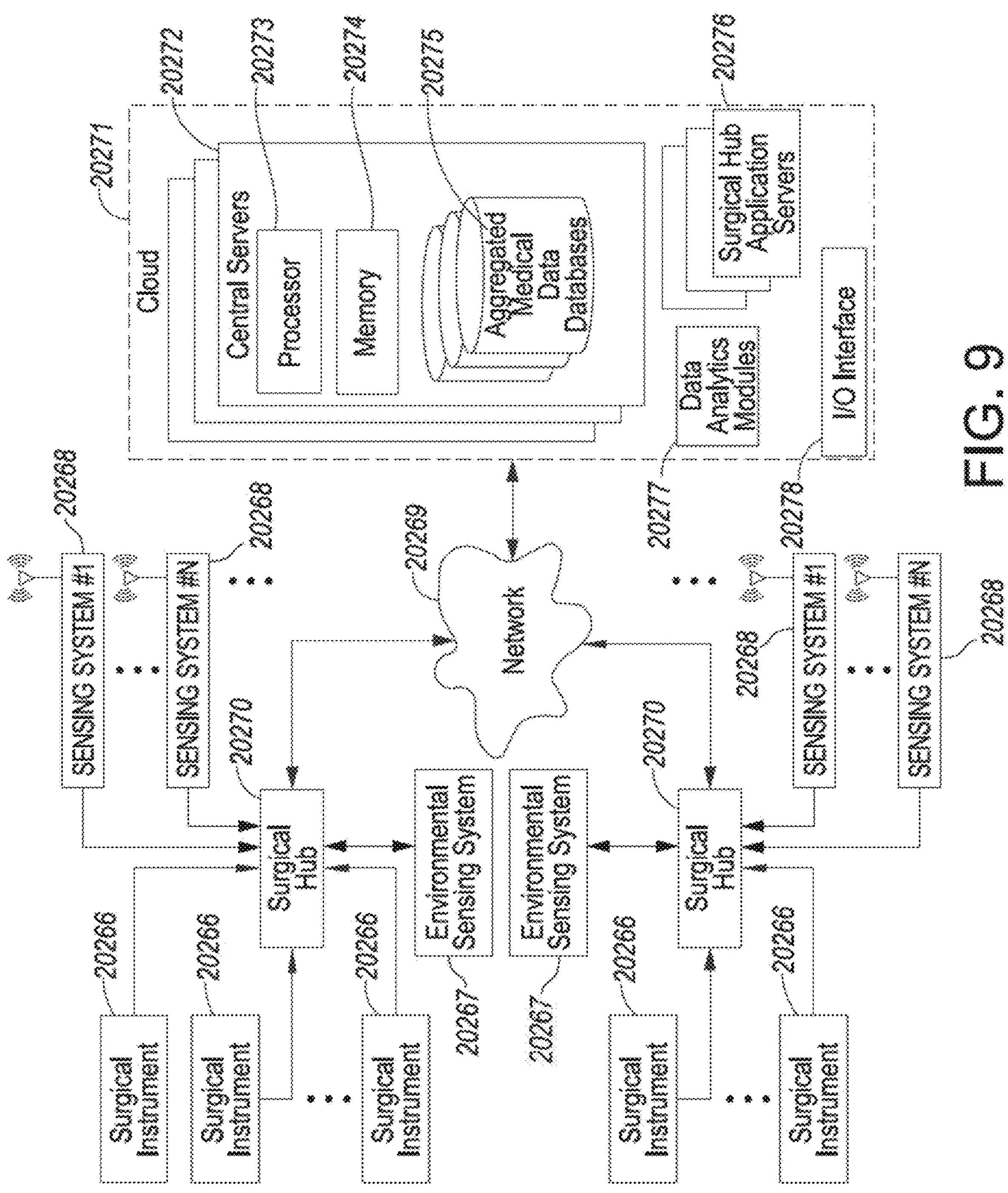
FIG. 9 is a block diagram of the computer-implemented interactive surgeon/patient monitoring system.

FIG. 9 is a block diagram of the computer-implemented interactive surgical system with surgeon/patient monitoring, in accordance with at least one aspect of the present disclosure. In one aspect, the computer-implemented interactive surgical system may be configured to monitor surgeon biomarkers and/or patient biomarkers using one or more sensing systems 20069. The surgeon biomarkers and/or the patient biomarkers may be measured before, after, and/or during a surgical procedure. In one aspect, the computer-implemented interactive surgical system may be configured to monitor and analyze data related to the operation of various surgical systems 20069 that include surgical hubs, surgical instruments, robotic devices and operating theaters or healthcare facilities. The computer-implemented interactive surgical system may include a cloud-based analytics system. The cloud-based analytics system may include one or more analytics servers.

As illustrated in FIG. 9, the cloud-based monitoring and analytics system may comprise a plurality of sensing systems 20268 (may be the same or similar to the sensing systems 20069), surgical instruments 20266 (may be the same or similar to instruments 20031), a plurality of surgical hubs 20270 (may be the same or similar to hubs 20006), and a surgical data network 20269 (may be the same or similar to the surgical data network described in FIG. 4) to couple the surgical hubs 20270 to the cloud 20271 (may be the same or similar to cloud computing system 20064). Each of the plurality of surgical hubs 20270 may be communicatively coupled to one or more surgical instruments 20266. Each of the plurality of surgical hubs 20270 may also be communicatively coupled to the one or more sensing systems 20268, and the cloud 20271 of the computer-implemented interactive surgical system via the network 20269. The surgical hubs 20270 and the sensing systems 20268 may be communicatively coupled using wireless protocols as described herein. The cloud system 20271 may be a remote centralized source of hardware and software for storing, processing, manipulating, and communicating measurement data from the sensing systems 20268 and data generated based on the operation of various surgical systems 20268.

As shown in FIG. 9, access to the cloud system 20271 may be achieved via the network 20269, which may be the Internet or some other suitable computer network. Surgical hubs 20270 that may be coupled to the cloud system 20271 can be considered the client side of the cloud computing system (e.g., cloud-based analytics system). Surgical instruments 20266 may be paired with the surgical hubs 20270 for control and implementation of various surgical procedures and/or operations, as described herein. Sensing systems 20268 may be paired with surgical hubs 20270 for in-surgical surgeon monitoring of surgeon related biomarkers, pre-surgical patient monitoring, in-surgical patient monitoring, or post-surgical monitoring of patient biomarkers to track and/or measure various milestones and/or detect various complications. Environmental sensing systems 20267 may be paired with surgical hubs 20270 measuring environmental attributes associated with a surgeon or a patient for surgeon monitoring, pre-surgical patient monitoring, in-surgical patient monitoring, or post-surgical monitoring of patient.

Surgical instruments 20266, environmental sensing systems 20267, and sensing systems 20268 may comprise wired or wireless transceivers for data transmission to and from their corresponding surgical hubs 20270 (which may also comprise transceivers). Combinations of one or more of surgical instruments 20266, sensing systems 20268, or surgical hubs 20270 may indicate particular locations, such as operating theaters, intensive care unit (ICU) rooms, or recovery rooms in healthcare facilities (e.g., hospitals), for providing medical operations, pre-surgical preparation, and/or post-surgical recovery. For example, the memory of a surgical hub 20270 may store location data.

As shown in FIG. 9, the cloud system 20271 may include one or more central servers 20272 (may be same or similar to remote server 20067), surgical hub application servers 20276, data analytics modules 20277, and an input/output ("I/O") interface 20278. The central servers 20272 of the cloud system 20271 may collectively administer the cloud computing system, which includes monitoring requests by client surgical hubs 20270 and managing the processing capacity of the cloud system 20271 for executing the requests. Each of the central servers 20272 may comprise one or more processors 20273 coupled to suitable memory devices 20274 which can include volatile memory such as random-access memory (RAM) and non-volatile memory such as magnetic storage devices. The memory devices 20274 may comprise machine executable instructions that when executed cause the processors 20273 to execute the data analytics modules 20277 for the cloud-based data analysis, real-time monitoring of measurement data received from the sensing systems 20268, operations, recommendations, and other operations as described herein. The processors 20273 can execute the data analytics modules 20277 independently or in conjunction with hub applications independently executed by the hubs 20270. The central servers 20272 also may comprise aggregated medical data databases 20275, which can reside in the memory 20274.

Based on connections to various surgical hubs 20270 via the network 20269, the cloud 20271 can aggregate data from specific data generated by various surgical instruments 20266 and/or monitor real-time data from sensing systems 20268 and the surgical hubs 20270 associated with the surgical instruments 20266 and/or the sensing systems 20268. Such aggregated data from the surgical instruments 20266 and/or measurement data from the sensing systems 20268 may be stored within the aggregated medical databases 20275 of the cloud 20271. In particular, the cloud 20271 may advantageously track real-time measurement data from the sensing systems 20268 and/or perform data analysis and operations on the measurement data and/or the aggregated data to yield insights and/or perform functions that individual hubs 20270 could not achieve on their own. To this end, as shown in FIG. 9, the cloud 20271 and the surgical hubs 20270 are communicatively coupled to transmit and receive information. The I/O interface 20278 is connected to the plurality of surgical hubs 20270 via the network 20269. In this way, the I/O interface 20278 can be configured to transfer information between the surgical hubs 20270 and the aggregated medical data databases 20275. Accordingly, the I/O interface 20278 may facilitate read/write operations of the cloud-based analytics system. Such read/write operations may be executed in response to requests from hubs 20270. These requests could be transmitted to the surgical hubs 20270 through the hub applications. The I/O interface 20278 may include one or more high speed data ports, which may include universal serial bus (USB) ports, IEEE 1394 ports, as well as Wi-Fi and Bluetooth I/O interfaces for connecting the cloud 20271 to surgical hubs 20270. The hub application servers 20276 of the cloud 20271 may be configured to host and supply shared capabilities to software applications (e.g., hub applications) executed by surgical hubs 20270. For example, the hub application servers 20276 may manage requests made by the hub applications through the hubs 20270, control access to the aggregated medical data databases 20275, and perform load balancing.

The cloud computing system configuration described in the present disclosure may be designed to address various issues arising in the context of medical operations (e.g., pre-surgical monitoring, in-surgical monitoring, and post-surgical monitoring) and procedures performed using medical devices, such as the surgical instruments 20266, 20031. In particular, the surgical instruments 20266 may be digital surgical devices configured to interact with the cloud 20271 for implementing techniques to improve the performance of surgical operations. The sensing systems 20268 may be systems with one or more sensors that are configured to measure one or more biomarkers associated with a surgeon perfuming a medical operation and/or a patient on whom a medical operation is planned to be performed, is being performed or has been performed. Various surgical instruments 20266, sensing systems 20268, and/or surgical hubs 20270 may include human interface systems (e.g., having a touch-controlled user interfaces) such that clinicians and/or patients may control aspects of interaction between the surgical instruments 20266 or the sensing system 20268 and the cloud 20271. Other suitable user interfaces for control such as auditory controlled user interfaces may also be used.

The cloud computing system configuration described in the present disclosure may be designed to address various issues arising in the context of monitoring one or more biomarkers associated with a healthcare professional (HCP) or a patient in pre-surgical, in-surgical, and post-surgical procedures using sensing systems 20268. Sensing systems 20268 may be surgeon sensing systems or patient sensing systems configured to interact with the surgical hub 20270 and/or with the cloud system 20271 for implementing techniques to monitor surgeon biomarkers and/or patient biomarkers. Various sensing systems 20268 and/or surgical hubs 20270 may comprise touch-controlled human interface systems such that the HCPs or the patients may control aspects of interaction between the sensing systems 20268 and the surgical hub 20270 and/or the cloud systems 20271. Other suitable user interfaces for control such as auditory controlled user interfaces may also be used.

Figure 10:
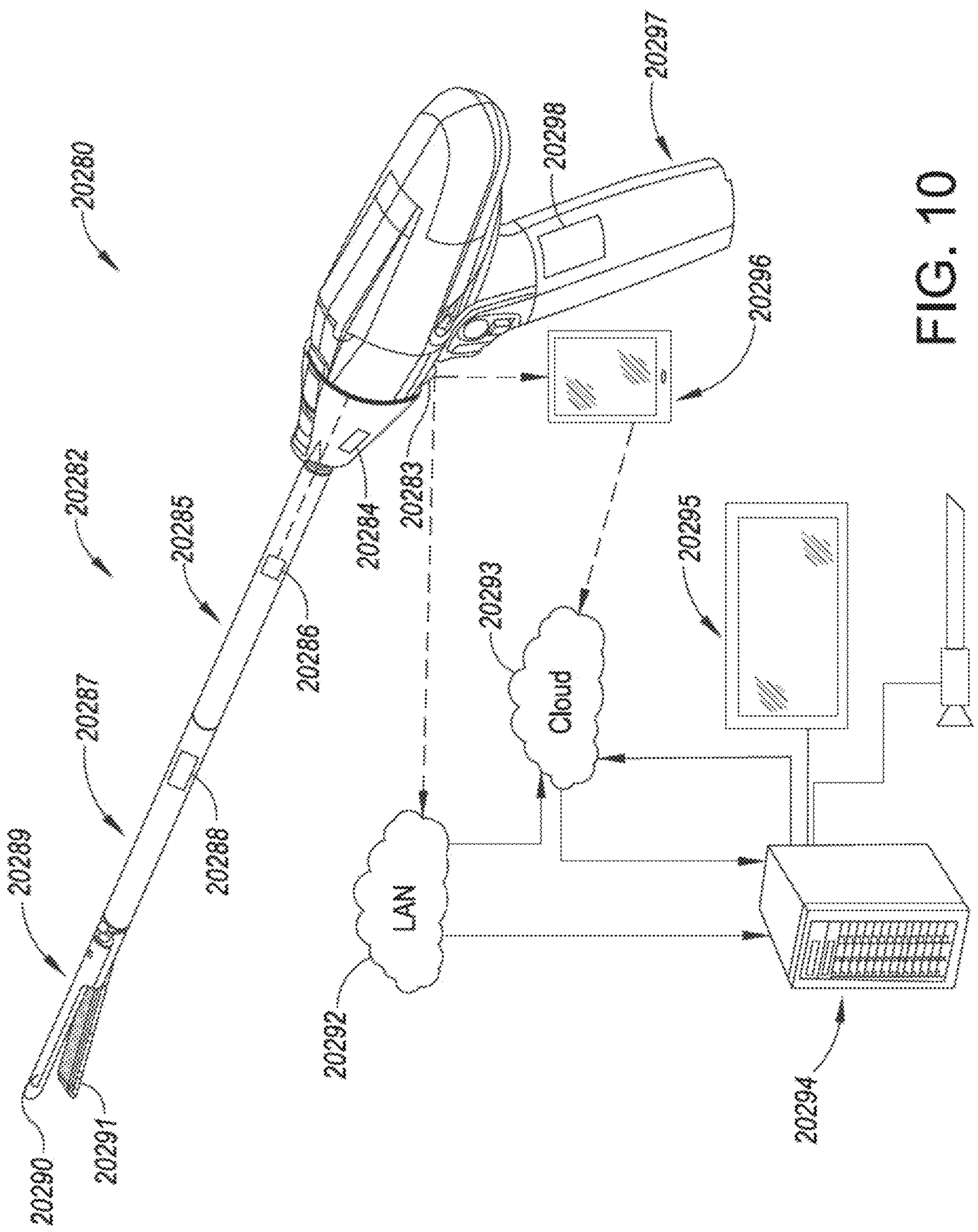
FIG. 10 shows an example surgical system that includes a handle having a controller and a motor, an adapter releasably coupled to the handle, and a loading unit releasably coupled to the adapter.

FIG. 10 illustrates an example surgical system 20280 in accordance with the present disclosure and may include a surgical instrument 20282 that can be in communication with a console 20294 or a portable device 20296 through a local area network 20292 or a cloud network 20293 via a wired or wireless connection. In various aspects, the console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub 20270, as illustrated in FIG. 9. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figures 11A, 11B, 11C, 11D:
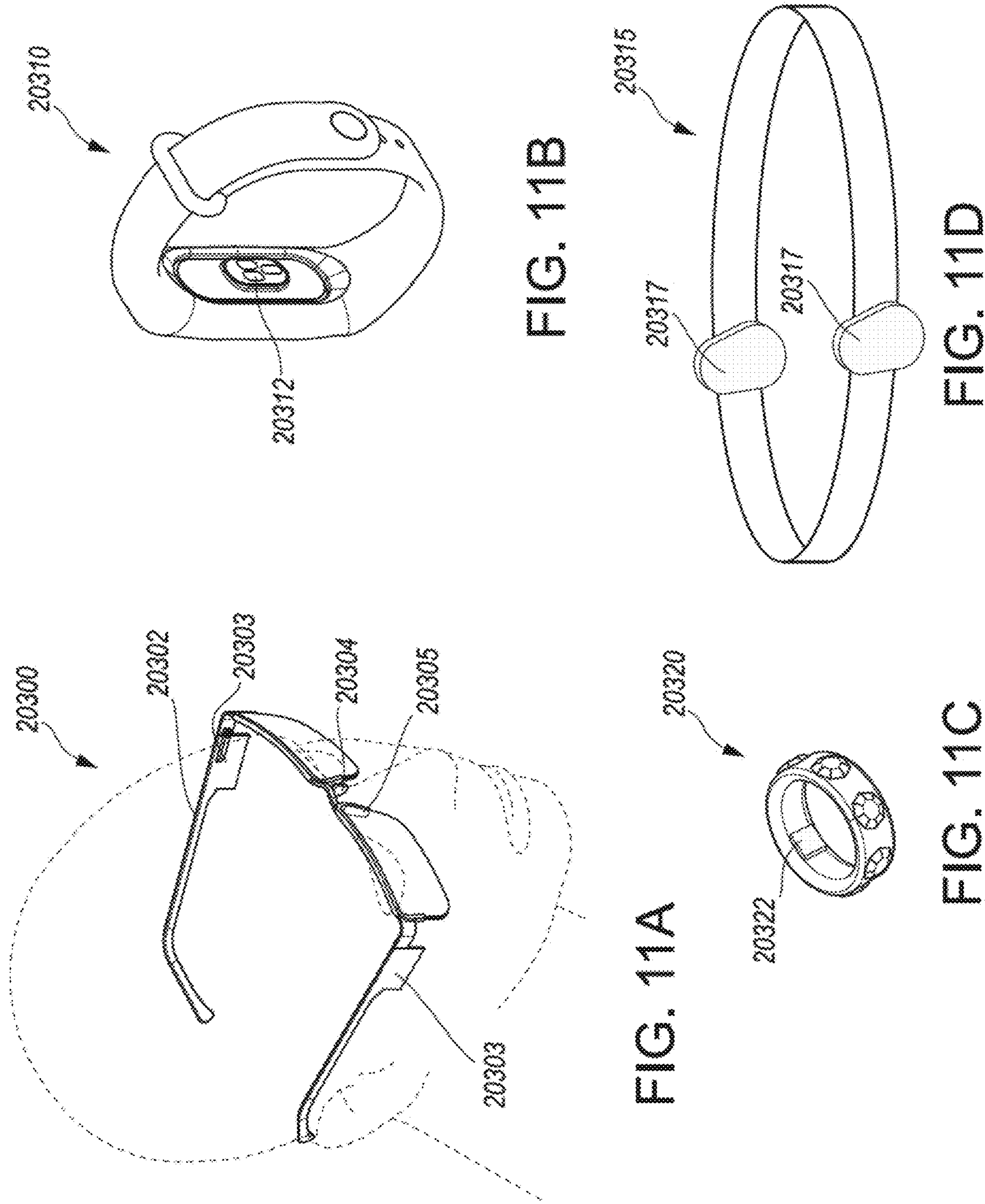
FIGS. 11A-11D illustrate examples of sensing systems that may be used for monitoring surgeon biomarkers or patient biomarkers.

FIG. 11A to FIG. 11D illustrates examples of wearable sensing systems, e.g., surgeon sensing systems or patient sensing systems. FIG. 11A is an example of eyeglasses-based sensing system 20300 that may be based on an electrochemical sensing platform. The sensing system 20300 may be capable of monitoring (e.g., real-time monitoring) of sweat electrolytes and/or metabolites using multiple sensors 20304 and 20305 that are in contact with the surgeon's or patient's skin. For example, the sensing system 20300 may use an amperometry based biosensor 20304 and/or a potentiometry based biosensor 20305 integrated with the nose bridge pads of the eyeglasses 20302 to measure current and/or the voltage.

The amperometric biosensor 20304 may be used to measure sweat lactate levels (e.g., in mmol/L). Lactate that is a product of lactic acidosis that may occur due to decreased tissue oxygenation, which may be caused by sepsis or hemorrhage. A patient's lactate levels (e.g., >2 mmol/L) may be used to monitor the onset of sepsis, for example, during post-surgical monitoring. The potentiometric biosensor 20305 may be used to measure potassium levels in the patient's sweat. A voltage follower circuit with an operational amplifier may be used for measuring the potential signal between the reference and the working electrodes. The output of the voltage follower circuit may be filtered and converted into a digital value using an ADC.

The amperometric sensor 20304 and the potentiometric sensor 20305 may be connected to circuitries 20303 placed on each of the arms of the eyeglasses. The electrochemical sensors may be used for simultaneous real-time monitoring of sweat lactate and potassium levels. The electrochemical sensors may be screen printed on stickers and placed on each side of the glasses nose pads to monitor sweat metabolites and electrolytes. The electronic circuitries 20303 placed on the arms of the glasses frame may include a wireless data transceiver (e.g., a low energy Bluetooth transceiver) that may be used to transmit the lactate and/or potassium measurement data to a surgical hub or an intermediary device that may then forward the measurement data to the surgical hub. The eyeglasses-based sensing system 20300 may use signal conditioning unit to filter and amplify the electrical signal generated from the electrochemical sensors 20305 or 20304, a microcontroller to digitize the analog signal, and a wireless (e.g., a low energy Bluetooth) module to transfer the data to a surgical hub or a computing device, for example, as described in FIGS. 7B through 7D.

FIG. 11B is an example of a wristband-type sensing system 20310 comprising a sensor assembly 20312 (e.g., Photoplethysmography (PPG)-based sensor assembly or Electrocardiogram (ECG) based-sensor assembly). For example, in the sensing system 20310, the sensor assembly 20312 may collect and analyze arterial pulse in the wrist. The sensor assembly 20312 may be used to measure one or more biomarkers (e.g., heart rate, heart rate variability (HRV), etc.). In case of a sensing system with a PPG-based sensor assembly 20312, light (e.g., green light) may be passed through the skin. A percentage of the green light may be absorbed by the blood vessels and some of the green light may be reflected and detected by a photodetector. These differences or reflections are associated with the variations in the blood perfusion of the tissue and the variations may be used in detecting the heart-related information of the cardiovascular system (e.g., heart rate). For example, the amount of absorption may vary depending on the blood volume. The sensing system 20310 may determine the heart rate by measuring light reflectance as a function of time. HRV may be determined as the time period variation (e.g., standard deviation) between the steepest signal gradient prior to a peak, known as inter-beat intervals (IBIs).

In the case of a sensing system with an ECG-based sensor assembly 20312, a set of electrodes may be placed in contact with skin. The sensing system 20310 may measure voltages across the set of electrodes placed on the skin to determine heart rate. HRV in this case may be measured as the time period variation (e.g., standard deviation) between R peaks in the QRS complex, known as R-R intervals.

The sensing system 20310 may use a signal conditioning unit to filter and amplify the analog PPG signal, a microcontroller to digitize the analog PPG signal, and a wireless (e.g., a Bluetooth) module to transfer the data to a surgical hub or a computing device, for example, as described in FIGS. 7B through 7D.

FIG. 11C is an example ring sensing system 20320. The ring sensing system 20320 may include a sensor assembly (e.g., a heart rate sensor assembly) 20322. The sensor assembly 20322 may include a light source (e.g., red or green light emitting diodes (LEDs)), and photodiodes to detect reflected and/or absorbed light. The LEDs in the sensor assembly 20322 may shine light through a finger and the photodiode in the sensor assembly 20322 may measure heart rate and/or oxygen level in the blood by detecting blood volume change. The ring sensing system 20320 may include other sensor assemblies to measure other biomarkers, for example, a thermistor or an infrared thermometer to measure the surface body temperature. The ring sensing system 20320 may use a signal conditioning unit to filter and amplify the analog PPG signal, a microcontroller to digitize the analog PPG signal, and a wireless (e.g., a low energy Bluetooth) module to transfer the data to a surgical hub or a computing device, for example, as described in FIGS. 7B through 7D.

FIG. 11D is an example of an electroencephalogram (EEG) sensing system 20315. As illustrated in FIG. 11D, the sensing system 20315 may include one or more EEG sensor units 20317. The EEG sensor units 20317 may include a plurality of conductive electrodes placed in contact with the scalp. The conductive electrodes may be used to measure small electrical potentials that may arise outside of the head due to neuronal action within the brain. The EEG sensing system 20315 may measure a biomarker, for example, delirium by identifying certain brain patterns, for example, a slowing or dropout of the posterior dominant rhythm and loss of reactivity to eyes opening and closing. The ring sensing system 20315 may have a signal conditioning unit for filtering and amplifying the electrical potentials, a microcontroller to digitize the electrical signals, and a wireless (e.g., a low energy Bluetooth) module to transfer the data to a smart device, for example, as described in FIGS. 7B through 7D.

Figure 12:
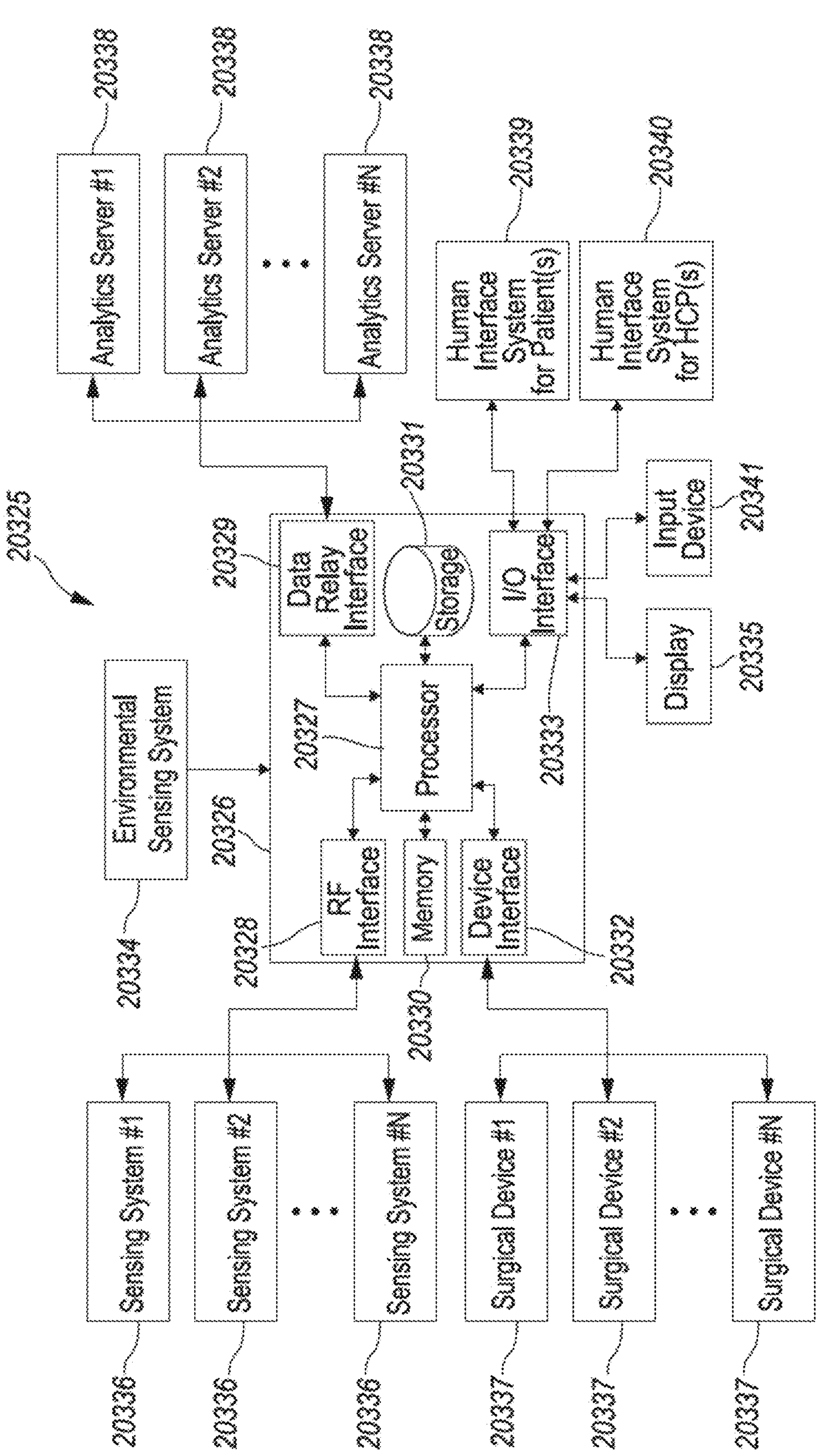
FIG. 12 is a block diagram of a patient monitoring system or a surgeon monitoring system.

FIG. 12 illustrates a block diagram of a computer-implemented patient/surgeon monitoring system 20325 for monitoring one or more patient or surgeon biomarkers prior to, during, and/or after a surgical procedure. As illustrated in FIG. 12, one or more sensing systems 20336 may be used to measure and monitor the patient biomarkers, for example, to facilitate patient preparedness before a surgical procedure, and recovery after a surgical procedure. Sensing systems 20336 may be used to measure and monitor the surgeon biomarkers in real-time, for example, to assist surgical tasks by communicating relevant biomarkers (e.g., surgeon biomarkers) to a surgical hub 20326 and/or the surgical devices 20337 to adjust their function. The surgical device functions that may be adjusted may include power levels, advancement speeds, closure speed, loads, wait times, or other tissue dependent operational parameters. The sensing systems 20336 may also measure one or more physical attributes associated with a surgeon or a patient. The patient biomarkers and/or the physical attributes may be measured in real time.

The computer-implemented wearable patient/surgeon wearable sensing system 20325 may include a surgical hub 20326, one or more sensing systems 20336, and one or more surgical devices 20337. The sensing systems and the surgical devices may be communicably coupled to the surgical hub 20326. One or more analytics servers 20338, for example part of an analytics system, may also be communicably coupled to the surgical hub 20326. Although a single surgical hub 20326 is depicted, it should be noted that the wearable patient/surgeon wearable sensing system 20325 may include any number of surgical hubs 20326, which can be connected to form a network of surgical hubs 20326 that are communicably coupled to one or more analytics servers 20338, as described herein.

In an example, the surgical hub 20326 may be a computing device. The computing device may be a personal computer, a laptop, a tablet, a smart mobile device, etc. In an example, the computing device may be a client computing device of a cloud-based computing system. The client computing device may be a thin client.

In an example, the surgical hub 20326 may include a processor 20327 coupled to a memory 20330 for executing instructions stored thereon, a storage 20331 to store one or more databases such as an EMR database, and a data relay interface 20329 through which data is transmitted to the analytics servers 20338. In an example, the surgical hub 20326 further may include an I/O interface 20333 having an input device 20341 (e.g., a capacitive touchscreen or a keyboard) for receiving inputs from a user and an output device 20335 (e.g., a display screen) for providing outputs to a user. In an example, the input device and the output device may be a single device. Outputs may include data from a query input by the user, suggestions for products or a combination of products to use in a given procedure, and/or instructions for actions to be carried out before, during, and/or after a surgical procedure. The surgical hub 20326 may include a device interface 20332 for communicably coupling the surgical devices 20337 to the surgical hub 20326. In one aspect, the device interface 20332 may include a transceiver that may enable one or more surgical devices 20337 to connect with the surgical hub 20326 via a wired interface or a wireless interface using one of the wired or wireless communication protocols described herein. The surgical devices 20337 may include, for example, powered staplers, energy devices or their generators, imaging systems, or other linked systems, for example, smoke evacuators, suction-irrigation devices, insufflation systems, etc.

In an example, the surgical hub 20326 may be communicably coupled to one or more surgeon and/or patient sensing systems 20336. The sensing systems 20336 may be used to measure and/or monitor, in real-time, various biomarkers associated with a surgeon performing a surgical procedure or a patient on whom a surgical procedure is being performed. A list of the patient/surgeon biomarkers measured by the sensing systems 20336 is provided herein. In an example, the surgical hub 20326 may be communicably coupled to an environmental sensing system 20334. The environmental sensing systems 20334 may be used to measure and/or monitor, in real-time, environmental attributes, for example, temperature/humidity in the surgical theater, surgeon movements, ambient noise in the surgical theater caused by the surgeon's and/or the patient's breathing pattern, etc.

When sensing systems 20336 and the surgical devices 20337 are connected to the surgical hub 20326, the surgical hub 20326 may receive measurement data associated with one or more patient biomarkers, physical state associated with a patient, measurement data associated with surgeon biomarkers, and/or physical state associated with the surgeon from the sensing systems 20336, for example, as illustrated in FIG. 7B through 7D. The surgical hub 20326 may associate the measurement data, e.g., related to a surgeon, with other relevant pre-surgical data and/or data from situational awareness system to generate control signals for controlling the surgical devices 20337, for example, as illustrated in FIG. 8.

In an example, the surgical hub 20326 may compare the measurement data from the sensing systems 20336 with one or more thresholds defined based on baseline values, pre-surgical measurement data, and/or in surgical measurement data. The surgical hub 20326 may compare the measurement data from the sensing systems 20336 with one or more thresholds in real-time. The surgical hub 20326 may generate a notification for displaying. The surgical hub 20326 may send the notification for delivery to a human interface system for patient 20339 and/or the human interface system for a surgeon or an HCP 20340, for example, if the measurement data crosses (e.g., is greater than or lower than) the defined threshold value. The determination whether the notification would be sent to one or more of the to the human interface system for patient 20339 and/or the human interface system for an HCP 2340 may be based on a severity level associated with the notification. The surgical hub 20326 may also generate a severity level associated with the notification for displaying. The severity level generated may be displayed to the patient and/or the surgeon or the HCP. In an example, the patient biomarkers to be measured and/or monitored (e.g., measured and/or monitored in real-time) may be associated with a surgical procedural step. For example, the biomarkers to be measured and monitored for transection of veins and arteries step of a thoracic surgical procedure may include blood pressure, tissue perfusion pressure, edema, arterial stiffness, collagen content, thickness of connective tissue, etc., whereas the biomarkers to be measured and monitored for lymph node dissection step of the surgical procedure may include monitoring blood pressure of the patient. In an example, data regarding postoperative complications could be retrieved from an EMR database in the storage 20331 and data regarding staple or incision line leakages could be directly detected or inferred by a situational awareness system. The surgical procedural outcome data can be inferred by a situational awareness system from data received from a variety of data sources, including the surgical devices 20337, the sensing systems 20336, and the databases in the storage 20331 to which the surgical hub 20326 is connected.

The surgical hub 20326 may transmit the measurement data and physical state data it received from the sensing systems 20336 and/or data associated with the surgical devices 20337 to analytics servers 20338 for processing thereon. Each of the analytics servers 20338 may include a memory and a processor coupled to the memory that may execute instructions stored thereon to analyze the received data. The analytics servers 20338 may be connected in a distributed computing architecture and/or utilize a cloud computing architecture. Based on this paired data, the analytics system 20338 may determine optimal and/or preferred operating parameters for the various types of modular devices, generate adjustments to the control programs for the surgical devices 20337, and transmit (or "push") the updates or control programs to the one or more surgical devices 20337. For example, an analytics system 20338 may correlate the perioperative data it received from the surgical hub 20236 with the measurement data associated with a physiological state of a surgeon or an HCP and/or a physiological state of the patient. The analytics system 20338 may determine when the surgical devices 20337 should be controlled and send an update to the surgical hub 20326. The surgical hub 20326 may then forward the control program to the relevant surgical device 20337.

Additional detail regarding the computer-implemented wearable patient/surgeon wearable sensing system 20325, including the surgical hub 30326, one or more sensing systems 20336 and various surgical devices 20337 connectable thereto, are described in connection with FIG. 5 through FIG. 7D.

Machine learning may be supervised (e.g., supervised learning). A supervised learning algorithm may create a mathematical model from training a dataset (e.g., training data). The training data may consist of a set of training examples. A training example may include one or more inputs and one or more labeled outputs. The labeled output(s) may serve as supervisory feedback. In a mathematical model, a training example may be represented by an array or vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function may determine the output for one or more inputs that may not have been a part of the training data. Example algorithms may include linear regression, logistic regression, and neutral network. Example problems solvable by supervised learning algorithms may include classification, regression problems, and the like.

Machine learning may be unsupervised (e.g., unsupervised learning). An unsupervised learning algorithm may train on a dataset that may contain inputs and may find a structure in the data. The structure in the data may be similar to a grouping or clustering of data points. As such, the algorithm may learn from training data that may not have been labeled. Instead of responding to supervisory feedback, an unsupervised learning algorithm may identify commonalities in training data and may react based on the presence or absence of such commonalities in each train example. Example algorithms may include Apriori algorithm, K-Means, K-Nearest Neighbors (KNN), K-Medians, and the like. Example problems solvable by unsupervised learning algorithms may include clustering problems, anomaly/outlier detection problems, and the like Machine learning may include reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP)) and may be used when exact models may not be feasible. Reinforcement learning algorithms may be used in autonomous vehicles or in learning to play a game against a human opponent.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

The output of machine learning's training process may be a model for predicting outcome(s) on a new dataset. For example, a linear regression learning algorithm may be a cost function that may minimize the prediction errors of a linear prediction function during the training process by adjusting the coefficients and constants of the linear prediction function. When a minimal may be reached, the linear prediction function with adjusted coefficients may be deemed trained and constitute the model the training process has produced. For example, a neural network (NN) algorithm (e.g., multilayer perceptrons (MLP)) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic functions. The NN algorithm may include a cost function to minimize classification errors by adjusting the biases and weights through a process of feedforward propagation and backward propagation. When a global minimum may be reached, the optimized hypothesis function with its layers of adjusted biases and weights may be deemed trained and constitute the model the training process has produced.

Data collection may be performed for machine learning as a first stage of the machine learning lifecycle. Data collection may include steps such as identifying various data sources, collecting data from the data sources, integrating the data, and the like. For example, for training a machine learning model for predicting surgical complications and/or post-surgical recovery rates, data sources containing pre-surgical data, such as a patient's medical conditions and biomarker measurement data, may be identified. Such data sources may be a patient's electronical medical records (EMR), a computing system storing the patient's pre-surgical biomarker measurement data, and/or other like datastores. The data from such data sources may be retrieved and stored in a central location for further processing in the machine learning lifecycle. The data from such data sources may be linked (e.g. logically linked) and may be accessed as if they were centrally stored. Surgical data and/or post-surgical data may be similarly identified, collected. Further, the collected data may be integrated. In examples, a patient's pre-surgical medical record data, pre-surgical biomarker measurement data, pre-surgical data, surgical data, and/or post-surgical may be combined into a record for the patient. The record for the patient may be an EMR.

Data preparation may be performed for machine learning as another stage of the machine learning lifecycle. Data preparation may include data preprocessing steps such as data formatting, data cleaning, and data sampling. For example, the collected data may not be in a data format suitable for training a model. In an example, a patient's integrated data record of pre-surgical EMR record data and biomarker measurement data, surgical data, and post-surgical data may be in a rational database. Such data record may be converted to a flat file format for model training. In an example, the patient's pre-surgical EMR data may include medical data in text format, such as the patient's diagnoses of emphysema, pre-operative treatment (e.g., chemotherapy, radiation, blood thinner). Such data may be mapped to numeric values for model training. For example, the patient's integrated data record may include personal identifier information or other information that may identifier a patient such as an age, an employer, a body mass index (BMI), demographic information, and the like. Such identifying data may be removed before model training. For example, identifying data may be removed for privacy reasons. As another example, data may be removed because there may be more data available than may be used for model training. In such case, a subset of the available data may be randomly sampled and selected for model training and the remainder may be discarded.

Data preparation may include data transforming procedures (e.g., after preprocessing), such as scaling and aggregation. For example, the preprocessed data may include data values in a mixture of scales. These values may be scaled up or down, for example, to be between 0 and 1 for model training. For example, the preprocessed data may include data values that carry more meaning when aggregated. In an example, there may be multiple prior colorectal procedures a patient has had. The total count of prior colorectal procedures may be more meaningful for training a model to predict surgical complications due to adhesions. In such case, the records of prior colorectal procedures may be aggregated into a total count for model training purposes.

Model training may be another aspect of the machine learning lifecycle. The model training process as described herein may be dependent on the machine learning algorithm used. A model may be deemed suitably trained after it has been trained, cross validated, and tested. Accordingly, the dataset from the data preparation stage (e.g., an input dataset) may be divided into a training dataset (e.g., 60% of the input dataset), a validation dataset (e.g., 20% of the input dataset), and a test dataset (e.g., 20% of the input dataset). After the model has been trained on the training dataset, the model may be run against the validation dataset to reduce overfitting. If accuracy of the model were to decrease when run against the validation dataset when accuracy of the model has been increasing, this may indicate a problem of overfitting. The test dataset may be used to test the accuracy of the final model to determine whether it is ready for deployment or more training may be required.

Model deployment may be another aspect of the machine learning lifecycle. The model may be deployed as a part of a standalone computer program. The model may be deployed as a part of a larger computing system. A model may be deployed with model performance parameters(s). Such performance parameters may monitor the model accuracy as it is used for predicating on a dataset in production. For example, such parameters may keep track of false positives and false positives for a classification model. Such parameters may further store the false positives and false positives for further processing to improve the model's accuracy.

Post-deployment model updates may be another aspect of the machine learning cycle. For example, a deployed model may be updated as false positives and/or false positives are predicted on production data. In an example, for a deployed MLP model for classification, as false positives occur, the deployed MLP model may be updated to increase the probably cutoff for predicting a positive to reduce false positives. In an example, for a deployed MLP model for classification, as false negatives occur, the deployed MLP model may be updated to decrease the probably cutoff for predicting a positive to reduce false negatives. In an example, for a deployed MLP model for classification of surgical complications, as both false positives and false negatives occur, the deployed MLP model may be updated to decrease the probably cutoff for predicting a positive to reduce false negatives because it may be less critical to predict a false positive than a false negative.

For example, a deployed model may be updated as more live production data become available as training data. In such case, the deployed model may be further trained, validated, and tested with such additional live production data. In an example, the updated biases and weights of a further-trained MLP model may update the deployed MLP model's biases and weights. Those skilled in the art recognize that post-deployment model updates may not be a one-time occurrence and may occur as frequently as suitable for improving the deployed model's accuracy.

The computing system may perform a learned behavior, such as a learned behavior determined using artificial intelligence and/or machine learning. Computing systems, such as cloud computing systems, may be provided to provide learning and/or adaptive system behavior to improve local data collection algorithms and control functions. A computing system may provide machine learning adaptation of one or more wearable devices and/or sensor collections of data to improve operability. For example, the operability of a wearable device, a sensor system, a surgical system, and the like may be improved by a computing system that may use machine learning.

A computing system may use an adaptive learning algorithm, which may be cloud based, to aggregate one or more data streams. A computing system may use an adaptive learning algorithm to aggregate meta-data from data collection. Machine learning and/or an adaptive learning algorithm may be used to improve the processing of data, the transportation of data, the storage of data. A computing system may use machine learning to determine one or more improvements that may be made in the collection and/or processing of data from one or more sensor feeds. For example, a computing system may use machine learning improved data collection to produce an improved power instrument algorithm that may contribute to a desired outcome, such as a surgical outcome. The desired outcome, which may be a surgical outcome, may include reduced complications, improved recovery rates, low false positive sensing issues, faster learning cycle of machine learning and/or artificial intelligence algorithms, a creation of advanced instrument operations, and the like.

The computing system may perform predictive or prognostic model generation. The computing system may generate one or more improvements to an algorithm and/or control of a wearable device, which may improve the relevancy of data that may come from the wearable device. The computing system may employ one or more machine learning techniques to improve one or more sensed data streams.

The computing system may generate one or more improvements to the learned efficiency and effectiveness of one or more machine learning algorithms. The computing system may employ machine learning to improve the artificial intelligence (AI) algorithm iterations. For example, the computing system may use machine learning to improve the training of another machine learning algorithm.

The computing system may allow user input, such as user feedback, to a random dataset generated based on data in the field for machine learning, such as continuous machine learning. The computing system may generate random dataset. The generated random dataset may improve a round (e.g., each round) the user or HCP runs a program. An HCP, such as a surgeon, may set what he/she would flag as high risk, medium risk, or low risk. The surgeon may mark what level of notification he/she would like to receive based on that specific generated dataset and/or whether he/she would like to be notified in one case versus another. Another HCP may handle the flag. One or more improvements may occur over time with datasets from patients (e.g., actual patients) and a HCP's (e.g., a surgeon) activity level of machine teaching and/or model training sessions. One or more improvements to a model may be made by receiving feedback from an HCP, which may occur when the HCP is on break, in between surgeries, and/or after an initial number of runs, when starting the program to teach the system, and the like. At a point, the machine learning and/or the dataset may transition from surgeon input to verification from the surgeon that the proper notifications and risk levels that the machine learning model may execute are correct. The computing system may output an overlay of the knowledge or understanding from the machine learning of how to react verses the surgeon's input(s). Such output may guide determining the need for more machine learning training and/or teaching sessions. The output may be used as a teaching tool for residents and nurses under a surgeon to give a visual representation on how to handle certain cases and overlay the output with the surgeon's input(s). Under such an approach, the computing system may minimize an overload of notifications and/or resources that may have bene used to annotate the data. The computing system may personalize the machine learning for a surgeon such that a surgical device and/or the machine learning may be tailored to the surgeon.

The computing system may perform machine learning and may adjust a sensitivity of the machine learning. The computing system may perform dynamic learning of a magnitude of conservation regarding given one or more complications and one or more predicted complications. For example, a false positive may be weighed similarly to a false negative with regards to whether the machine was correct or not, which may influence the machine learning algorithm. The weight of the false negative may be adjusted to be scrutinized in the machine learning algorithm to lean toward a false positive in output versus a false negative that may be tailored to one or more complications.

Machine learning may be used to generate one or more datasets. The generation of the one or more datasets may be based on prioritizing areas, cases, situations, and the like that machine learning may not be familiar with. The generation of the one or more data sets may be based on a situation that the machine learning may not have seen yet. As such, the machine learning may generate a dataset, the machine learning may be trained, or the machine learning may be prepared when case such area, cases, and situations may occur.

The computing system may provide and/or perform one or more improvements to the aggregating of data. The computing system may provide and/or may perform a prediction of surgical complications, patient complications, recovery milestones, and the like. The computing system may employ machine learning to improve one or more patient monitoring measures. Machine learning adaptation of sensing and/or indications may be performed. Risk probability aggregation may be provided. For example, risk probability aggregation may be used to choose a system response.

A machine learning database may be provided. The machine learning database may include a data collection, one or more artificial intelligence models, and the like. Data used by the machine learning may include one or more contexts that may be associated with or tailored to a predictive model. For example, a machine learning model for <3 days post-op may be generated. For example, a machine learning model for patient with an underlying condition may be generated. For example, a machine learning model for one or more biomarkers during exercise may be generated. For example, a machine learning model for one or more biomarkers of patients with hypertension while eating may be generated.

The computing system may improve wearable milestone(s), threshold(s), and/or interrelationship(s). As the data for any of the procedure types (e.g., colorectal, Bariatric, Thoracic, GYN) may be processed for procedure steps and instrument use, the wearables pre-cursor information may be integrated and may allow the machine learning system to identify other interrelated wearable datasets that may provide indicators of the procedural complications (e.g., one or more surgical complications). Thresholds and algorithms associated with the data may be downloaded back to the computing system (e.g., a surgical hub) and may be sent to the wearables through the computing system with improved monitoring algorithms of threshold points to indicate complications on future procedures.

The computing system may improve communication and interconnecting methods. As the automated pairing systems may identify systems with which that may interact with or may not interact with, the machine learning may identify one or more ways for the systems to interact or spoof the wearable into believing the wearable was attached to a system that the wearable may interact with and provide data to. Example machine learning systems may be include distributed training, Jupyter Notebooks, continues integration/continuous delivery (CI/CD), hyperparameter optimization, feature stores, and the like.

Disclosed herein are methods, systems, and apparatus to provide machine learning that may be used to improve artificial intelligence algorithms and may reduce the iterations used to train artificial intelligence algorithms. Adaptive learning algorithms may be used to aggregate one or more data streams. Adaptive learning algorithms may be used to generate and/or determine meta-data from a data collection. Adaptive learning algorithms may be used to process data, determine an efficient way to transport data, determine an efficient way to store data, and the like. Adaptive learning may be used to determine one or more improvements from a previous machine learning analysis. Improvements in the collection and or processing of sensor feeds, data feeds, and/or biomarker feeds may be used to produce improved power instrument algorithms. For example, improvements may be used to produce improved power instrument algorithms based on a desired outcome (e.g., a surgical outcome).

A computing system and/or a method may be used for applying machine learning to a data collection to improve a surgical outcome. The computing system may comprise a processor that may perform the method. A data collection that includes one or more biomarkers may be determined. The data collection and/or the one or more biomarkers may indicate that an operational behavior of a surgical device may be suboptimal. A model may be determined using machine learning and the data collection. The model may optimize and/or improve the operational behavior of the surgical device to improve a surgical outcome. The model may be updated using a feedback given by a healthcare provider (HCP) to improve the model. A control program update may be generated using the model and the collection data. The control program update may be configured to alter a manner in which a control program operates the surgical device during a surgical procedure. The control program update may be sent to the surgical device.

A computing system and/or method may be used for applying machine learning to a data collection to improve a surgical outcome. The computing system may comprise a processor that may perform the method. It may be determined from a data collection that includes one or more biomarkers that an operational behavior of a surgical device may be suboptimal. A model that optimizes and/or improves the operational behavior of the surgical device and may predict a surgical complication may be determined using machine learning and the data collection. The model may be updated using a feedback given by a healthcare provider (HCP) to improve the model. The control program update may be generated using the model and the data collection. The control program update may be configured to alter a manner in which a control program may operate the surgical device during a surgical procedure to prevent the surgical complication. The control program update may be sent to the surgical device.

A computing system and/or a method may be used for applying machine learning to a data collection to improve a surgical outcome. The computing system may comprise a processor that may perform the method. It may be determined that an operational behavior of a surgical device may be suboptimal using a surgical device data and a biomarker from a sensing system. A model that optimizes and/or improves the operational behavior of a surgical device to improve the surgical outcome may be determined using machine learning, the surgical device data, and the biomarker. The model may be updated using a feedback given by a healthcare provider (HCP) to improve the model. A control program update may be generated using the biomarker and the surgical device data. The control program update may be configured to alter a manner in which a control program may operate the surgical device during a surgical procedure. The control program update may be sent to the surgical device.

Machine learning models may be generated from various data sources, such as patient EMR data, pre-surgical biomarker measurement data, surgical biomarker measurement data, surgical sensor measurement data, post-surgical biomarker measurement data, and biomarker sensor thresholds data. The machine learning models may predict surgical complications and/or post-surgical recovery milestones related to a patient's surgical procedure.

For example, such machine learning models may be created and trained locally at a computing system (e.g., a surgical hub) using data sources that may be connected with the computing system.

For example, machine learning models may be created and/or trained by a group of interconnected computing systems (e.g., surgical hubs) that may be at a physical location (e.g., in an operating room). Machine learning models be created and/or trained using data sources that may be collected by a group of computing systems. A group of interconnected computing systems may communicate with one another to detect an unused processing capacity and/or an unused data storage capability on another computing system and may distribute processing tasks to an underutilized computing system. The of processing tasks may include data collection, data preparation, model training, model validation, and/or model testing.

Embodiments disclosed herein may use distributed processing. Distributed processing may be coordinated by a first computing system, which may be in the operating room. The first computing system may direct a second computing system. The distributed processing may be coordinated using a peer-to-peer communication protocol.

Machine learning models may be created and/or trained at a server, at a cloud system, and the like. A cloud system that may have trained a machine learning model may be connected with one or more computing systems, which may be in various geographical locations. The cloud computing system may provide the one or more computing systems with access to one or more data sources.

One or more sensing systems may be located in an operating room and may be used to distribute the processing of sensor measurement data. For example, a first sensing system may not have sufficient capacity to process measurement data locally and may rely on a second sensing system and/or a computing system to process the measurement data. In an example, a first sensing system and/or a first computing system may be able to detect a second computing system and/or a second sensing system that may have an unused processing capacity. And the first sensing system and/or the first computing system may distribute processing to the second computing system and/or the second sensing system. For example, a first surgical hub in an operating room may determine that a second surgical hub in the operating room may have an unused processing capacity and the first surgical hub may distribute one or more processing tasks to the second surgical hub.

The computing system (e.g., a surgical hub) may adjust a data sampling rate and/or a data precision of a sensing system during a surgical procedure. For example, in a procedure step, the computing system may determine that it may not be necessary for the data sampling rate and/or data precision for biomarker measurement data from sensing system A to remain the same as that of the previous procedure step. In such case, the computing system may request sensing system A to scale down the data sampling rate and/or data precision. The computing system may determine the biomarker measurement data from a sensing system B to be more relevant. The computing system may request sensing system A to scale up the data sampling rate and/or data precision. The sensing system B may have sufficient processing capacity to scale up the data sampling rate and/or data precision as requested. The sensing system B may have insufficient processing capacity and may share processing tasks with the sensing system A and/or with the computing system.

The computing system may scale up data sampling rate and/or data precision of a sensing system during a surgical procedure based on a machine learning model's prediction(s). In an example, a machine learning model may be created and/or trained to predict probabilities of surgical complications. In such example, the machine learning model may predicate a probability of a surgical complication. Based on the predicted probability of the surgical complication, the computing system may determine request a sensing system C to scale up its data sampling rate and/or data precision based on the sensing system C biomarker measurement data's relevance with the predicted complication. The request may be to scale up a heart rate variability measurement from one measurement per minute (e.g., on an Apple Watch) to one measurement per second. The request may be to scale up a heart rate variability measurement from one decimal place to three decimal places. The request may be to scale up the complexity of a heart rate variability measurement from a mean score to a mean score with an associated standard deviation.

In response to the request to scale up data sampling rate, data precision, and/or data complexity, the sensing system C may scale up as requested. The sensing system C may not have sufficient processing capacity to scale up as data may be more frequently collected. The sensing system C may not have sufficient processing capacity to scale up as more data is being collected. The sensing system C may indicate to the computing system that sensing system C may lack processing capacity and the computing system may request the sensing system C to transmit raw measurement data without processing to the computing system for further processing at the computing system. The computing system request one or more other sensing systems (e.g. sensing system A and/or sensing system B) to scale down a data sampling and/or a data precision to reduce an amount of bandwidth that may be used within an operating room. (e.g., to mitigate the potential communication bandwidth bottlenecks).

Figure 13:
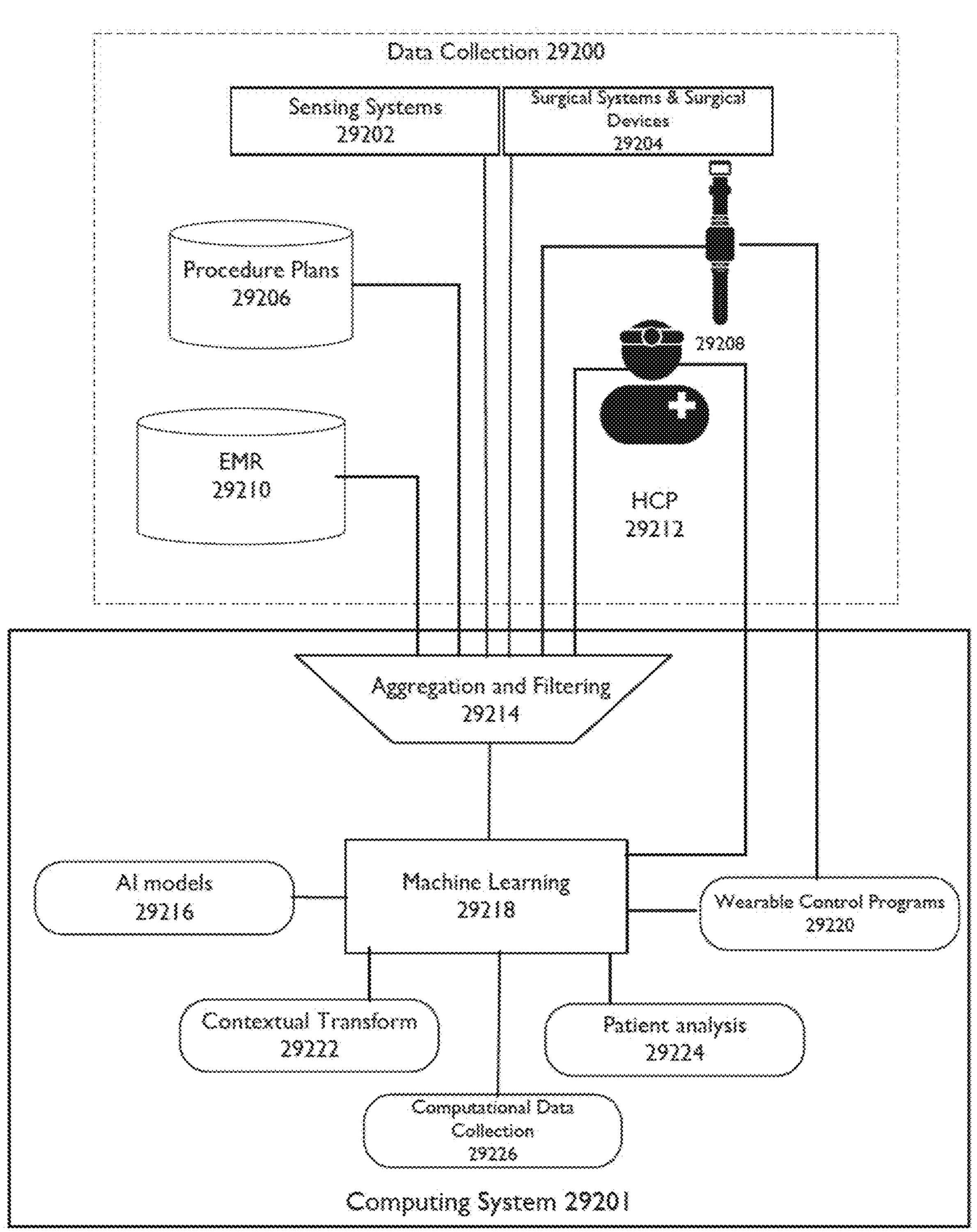
FIG. 13 depicts a block diagram for applying machine learning to improve algorithms and/or controls of the one or more wearables.

FIG. 13 depicts a block diagram for applying machine learning to improve algorithms and/or controls of one or more wearables.

The computing system 29201 may include computing hardware including a processor, memory, input/output subsystems, and the like. The processor may be configured (via application specific hardware, software, firmware, or the like) to transform received data and to derive contextualized for output. For example, the processor may include a microprocessor, a microcontroller, a FPGA, and an application-specific integrated circuit (ASIC), a system-on-a-chip (SOIC), a digital signal processing (DSP) platform, a real-time computing system, or the like. For example, processor may be configured to implement computing functions and/or modules as disclosed herein. For example, the processor may be configured for aggregation and/or filtering 29214, machine learning 29218, contextual transform 29222 (e.g., including real-time intra-operative processing), artificial intelligence models 29216, patient analysis 29224, wearable control programs 29220, wearable device data collection 29226, and the like.

The computing system 29201 may be any device suitable for processing sensor, health record data, EMR data, user input, training a machine learning model, deploying a machine learning model, creating a machine learning model, and the like. The computing system 29201 may be any device suitable for using a machine learning model to determine and/or predict one or more surgical outcomes, one or more surgical complications, and the like.

The computing system 29201 may be any device suitable to transform data and derive computational data for output, such as computational data collection 29226. Computational data collection 29226 may include contextualized data. Computational data collection 29226 may include a prediction, a machine learning model, and artificial intelligence model, pre-surgical data, surgical data, post-surgical data, a biomarker, a sensor measurement, and the like. Computational data collection 29226 may include contextualized data that may include a context. A context, for example, may be additional information that may be relevant to an understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins.

The computing system 29201 may be incorporated with any method suitable for implementation of the functionality disclosed herein. For example, the computing system 29201 may be incorporated as a stand-alone computing system. For example, the computing system may be incorporated into a surgical hub, such as that disclosed in FIG. 1. For example, the computing system 29201 may be incorporated into a sensing system itself (e.g., sensing both pre-surgical and surgical data and providing contextualized data as an output). For example, the computing system 29201 may be incorporated into a surgical device itself (e.g., receiving, pre-surgical, surgical data, and post-surgical data and providing computational data, contextualized data, and/or alerts as an output).

A data collection, such as data collection 29200 may be provided. Machine learning may use the data collection, such as data collection 29200. Data collection 29200 may be used by machine learning to train a model, verify a model, determine a model, and the like.

Data collection 29200 may include one or more data sources. For example, data collection 29200 may include a pre-surgical data collection, a surgical data collection, a post-surgical data collection, contextualized surgical data collection, and the like. Data collection 29294 may include one or more biomarkers. The one or more biomarkers may come from one or more computing systems, surgical sensing systems, wearable devices, displays, surgical instruments, surgical devices, sensor systems, devices, and the like. The data collection 29200 may include electronic medical records for a patient, data for a patient, data for other patients, data regarding past procedures, data regarding research for procedures, medical data, instructions from a health care provider, plans for a surgical procedure, and the like.

Data collection 29200 may include data from a one or more data sources. For example, the sources may include procedure plans database 29206, EMR 29210, sensing systems 29202, surgical systems & surgical devices 29204, wearable device 29208, and data from HCP 29212.

Data collection 29294 may include a pre-surgical data collection. The pre-surgical data collection may include data from one or more data sources. The pre-surgical data collection may include data that is related to a patient that may be recorded prior to a surgery. The pre-surgical data collection may include one or more biomarkers they may have been recorded for a patient prior to a surgery. For example, a heart rate and blood glucose level for a patient may be recorded for a patient prior to a surgery.

The pre-surgical data collection may include data from sensing systems 29202, such as pre-surgical sensing system. The pre-surgical sensing system may include any configuration of hardware and software devices suitable for sensing and presenting patient parameters and/or biomarkers that may be relevant before, during, or after a surgical procedure. Such a pre-surgical sensing system may include any of the sensing and monitoring systems disclosed herein, including uncontrolled patient monitoring systems, controlled patient monitoring systems, and the like. For example, pre-surgical sensing system may include a wearable patient sensor system. The pre-surgical sensing system may provide data suitable for establishing baselines of patient biomarkers for use in contextual determination during and/or after surgery. The pre-surgical sensing system may incorporate or be incorporated into the sensing system 20001 as shown in FIG. 1B.

The pre-surgical data collection may include data from wearable device 29208. Wearable device 29208 may include any configuration of hardware and software devices suitable for sensing and presenting patent parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at home for four weeks prior to a surgical procedure. And/or, via a controlled patient monitoring system, a HCP may monitor the same and/or analogous biomarkers using facility equipment during time the patient is prepped immediately before the surgical procedure. For example, the wearable device 29208 may provide data suitable for establishing baselines of patient biomarkers for use in contextual determination during and/or after surgery. Wearable device 29208 may include any of those disclosed herein, such as those with reference to FIG. 1B for example.

The pre-surgical data collection may include procedure plans 29206. Procedure plans 29206 may include any data source relevant to a health procedure (e.g., relevant to a health procedure in view of a particular patient and/or facility). Procedure plan 29206 may include structured data indicative of the desired end result, the surgical tactics to be employed, the operation logistics, and the like. Procedure plan 29206 may include an accounting of the equipment to be used and/or the techniques to be used. Procedure plan 29206 may include an order. Procedure plan 29206 may include a timeline. The structured data may include defined fields and/or data tags associated corresponding values. The structured data may include codes associated with one or more processes of a surgical procedure (e.g., surgical procedure steps).

The pre-surgical data collection may include EMR 29210. EMR 29210 may include any data source relevant to a patient in view of a health procedure, such a surgical procedure. EMR 29210 may include information such as allergies and/or adverse drug reactions, chronic diseases, family medical history, illnesses and/or hospitalizations, imaging data, laboratory test results, medications and dosing, prescription record, records of surgeries and other procedures, vaccinations, observations of daily living, information collected by sensing system 29202 (e.g., pre-surgical), information collected by wearable device 29208, and the like.

The pre-surgical data collection may include data from a pre-surgical healthcare provider, such as HCP 29212. Data from HCP 29212 may include any data relevant to a pre-surgical sensing system, a patient record, a procedure plan, and the like. Data from HCP 29212 may include data that may be relevant to an operation, configuration, and/or management of a computing system, such as computing system 29201. For example, data from HCP 29212 include feedback that may be provided to a machine learning module, such a machine learning 29218. The data from HCP 29212 may include manually entering data that may not be received directly for a relevant source (such as manually entering a manually taken biomarker reading, for example).

Data collection 29294 may include a surgical data collection. The surgical data collection may include data from one or more data sources. The surgical data collection may include data that may be related to a patient that may be recorded during a surgery. The surgical data collection may include one or more biomarkers they may have been recorded for a patient during a surgery. For example, a heart rate and blood glucose level for a patient may be recorded for a patient during a surgery.

The surgical data collection may include one or more data sources. The surgical data collection may include data from sensing systems 29202, HCP 29212, surgical systems & surgical devices 29204, and wearable device 29208.

The surgical data collection may include data from sensing system 29202, such as a surgical sensing system. The surgical sensing system may include any configuration of hardware and software devices suitable for sensing and presenting parameters patient biomarkers that may be relevant during a surgical procedure. The surgical sensing system may include the sensing and monitoring systems disclosed herein, including controlled patient monitoring systems, surgeon monitoring systems, environmental sensing systems, and the like.

The surgical data collection may include data from wearable device 29208. Wearable device 29208 may include any configuration of hardware and software devices suitable for sensing and presenting patent parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at during a surgical procedure. And/or, via a controlled patient monitoring system, a HCP may monitor the same and/or analogous biomarkers using facility equipment during time of the surgical procedure. For example, the wearable device 29208 may provide data suitable for use in a contextual determination during and/or after surgery. Wearable device 29208 may include any of those disclosed herein, such as those with reference to FIG. 1B for example.

Surgical systems & surgical devices 29204 may include any surgical equipment suitable for providing operative data regarding its configuration, use, and/or present condition and/or status, for example. Surgical systems & surgical devices 29204 may include equipment in the surgical theater. Surgical systems & surgical devices 29204 may include any equipment employed in the surgical theater, such as that disclosed with reference to FIG. 1, FIG. 7A, FIG. 10, and throughout the present application, for example. The surgical systems & surgical devices 29204 may include surgical fixtures of a general nature, such as a surgical table, lighting, anesthesia equipment, robotic systems, and/or life-support equipment. Surgical systems & surgical devices 29204 may include surgical fixtures that may be related to the procedure at-hand, such as imaging devices, surgical staplers, energy devices, endocutter clamps, and the like. For example, surgical systems & surgical devices 29204 may include be one or more of a powered stapler, a powered stapler generator, an energy device, an energy device generator, an in-operating-room imaging system, a smoke evacuator, a suction-irrigation device, an insufflation system, or the like.

The surgical systems & surgical devices 29204 may include at least one of a surgical instrument, surgical visualization system, monitor, sound system, energy devices, a wearable, and the like. For example, the surgical system may include a surgical hub. For example, the surgical system may include a surgical stapler. For example, the surgical system may include an endocutter, for example. Data from the surgical instrument may include surgical instrument parameters. The surgical instrument parameters may include surgical instrument power, for example. Data from the surgical visualization system may include the location of surgical instruments in relation to a patient surgical site and/or organ. For example, data may include the distance between a surgical stapler and a close vital organ.

Surgical data collection may include data from a surgical HCP, such as HCP 29212. Data from HCP 29212 may include any data relevant to a surgical sensing system, a wearable device, a surgical system, a machine learning, a patient analysis, a surgical device control program, a wearable control program, a contextual transform, an artificial intelligence model, and the like. For example, HCP 29212 may provide data that may be associated with surgical systems & surgical devices 29204, wearable device 29208, sensing system 29202, machine learning 29218, and the like. For example, the HCP 29212 may provide data that may trigger an interaction with the context transform 29222 and/or machine learning 29218. The data from HCP 29212 may include manually entering data not received directly for any relevant source (such as manually entering a manually taken biomarker reading, for example).

The data received from data collection 29200 may be subject to aggregation and/or filtering 29214. Aggregation and/or filtering 29214 may perform pre-processing on data received from data collection 29200. Aggregation and/or filtering 29214 may be used to prepare and format the data for use by computing system 29201. For example, aggregation and/or filtering 29214 may prepare data to be processed by machine learning 29218, contextual transform 29222, artificial intelligence models 29218, patient analysis 29224, wearable device data collection 29226, and wearable control programs 29220.

Processing the data received from data collection 29200 by aggregation and/or filtering 29214 may include filtering (e.g., to select sensor data from the stream of data from pre-surgical sensing system). Aggregation and/or filtering 29214 may use filtering to help reject noise in data from data collection 29200. Aggregation and/or filtering 29214 may use a method to establish a baseline for a biomarker from data collection 29200. Aggregation and/or filtering 29214 may perform time mapping on data from data collection 29200 (e.g., to place received values from different sources in alignment with each other in regard to time). Time mapping may aid in correlation and ratio analysis, which may occur in contextual transform 29222.

Aggregation and/or filtering 29214 may translate data from data collection 29200. The translation of data may include coordinating formats, coordinating data types, translating from one format to another format, translating from one data type, to another data type, accounting for a difference between a data source data format, and accounting for a data type expected by another module, such as machine learning 29218. Translating may include translating the data into a format suitable for machine learning, for artificial intelligence models, for patient analysis, for use by a surgical device control program, and/or for use by a wearable control program.

Contextual transform 29222 may operate to provide a context for data from data collection 29200. For example, contextual transform 29266 may transform data into contextualized surgical data. To illustrate, as an input the contextual transform may receive surgical data that includes, for example, a measurement time, a sensor system identifier, and a sensor value. Contextual transform 29222 may output contextualized surgical data. Contextual transform 29222 may output data that may be modified and/or enhanced by machine learning 29218, patient analysis 29224, wearable control programs 29220, wearable device data collection 29226, and artificial intelligence models 29216.

Contextual transform 29222 may determine and/or store data that may be related. Contextual transform 29222 may determine how data may be related. For example, contextual transform 29222 may determine that data from the surgical data collection may be related to data from the pre-surgical data collection. Contextual transform 29222 may determine a context for the data. Context, for example, additional information relevant to the present understanding and/or interpretation of the sensor measurement.

Computational data collection 29266 may be determined and/or generated by machine learning 29218. For example, machine learning 29218 may receive data from data collection 29200, may apply a machine learning model, and may use the machine learning model to generate the computational data collection 29226.

Computational data collection 29226 may include one or more biomarkers that may be augmented and/or enhanced by a machine learning model. For example, one or more biomarkers may be modified to make the one or more biomarkers more accurate using the machine learning model. Computational data collection 29226 may include one or more predictions and/or probabilities That may be associated with a patient, a surgical outcome, a diagnosis, a morbidity, and the like.

Computational data collection 29226 may include feedback from an HCP, such as HCP 29212. The feedback may be regarding a training of an artificial intelligence model, an accuracy of a biomarker, an accuracy of a prediction, A modification of a control program for a wearable device, a modification of a control program for a surgical device, and the like. For example, computational data collection 29226 may include feedback that indicates that an artificial intelligence model may be improving surgical outcomes when a surgical device is used with the modified control program generated by the artificial intelligence model. The computational data collection 29226, may include correlation analysis (e.g., to establish a baseline for relationships between and/or among biomarkers from the data collection 29200).

Computation data collection 29226 may include context, for example, additional information relevant to the present understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins. Computational data collection 29226 may include data sent to or received from surgical systems & surgical devices 29204, wearable device 29208, sensing systems 29202, procedure plans 29206, EMR 29210, and/or HCP 29212. Computational data collection 29226 may be created, modified, received by and/or sent by machine learning 29218, contextual transform 29222, artificial intelligence models 29216, patient analysis 29224, wearable control programs 29220, and/or any combination thereof.

Computational data collection 29226 may include data that may provide a context. The context may include additional information that may have been created and/determined by machine learning 29218 that may place a biomarker into a specific context for the healthcare providers. For example, computational data collection 29226 may include instructions and/or information about a baseline value for a sensor value, an alert of a deviation, relevant information from the patient's record, relevant information to a procedural element of the surgery, surgical device settings, and/or any information the healthcare provider might find relevant to have at the moment of the sensor's measurement itself. Computational data collection 29226 may include one or more data tags. The data tags may include logging data (indicating that that a specific transform or other processing has occurred).

Computational data collection 29226 may include data that may be provided by HCP 29212 and may have been modified and/or augmented by machine learning 29218. For example, HCP 29212 may provide feedback regarding data provided by machine learning 29218. Computational data collection 29226 may include data that may be sent to HCP 29212. For example, HCP 29212 may receive data provided by machine learning 29218. Data from HCP 29212 may include any data relevant to a surgical sensing system, a wearable device, a surgical system, a machine learning, a patient analysis, a surgical device control program, a wearable control program, a contextual transform, an artificial intelligence model, and the like.

Computational data collection 29226 may include data from wearable device 29208. For example, device may be received from wearable device 29208 and may be processed by machine learning 29208. Machine learning 29218 may modify the data received from wearable device 29208 and may I put that data as computational data collection 29226. Machine learning 29208 may augment the data received from wearable device 29208. For example, one or more biomarkers received from 29208 may be improved by machine learning 29218 by augmenting the one or more biomarkers Machine learning 29218 may create, generate, train, and/or determine artificial intelligence (AI) models. The AI models may be stored in AI models 29216. Machine learning 29218 may create, generate, train, and/or determine artificial AI models using data collection 29200. Machine learning 29218 may generate data, such as computational data collection 29226, using one or more AI models.

Machine learning 29218 may use data collection 29200 to create and/or training a model for wearable device 29208. Machine learning 29218 may create, train, generate, and/or determine a model to improve an algorithm or control of wearable device 29208. For example, machine learning 29218 may train a model using data from data collection 29200. The model may indicate that an operation of wearable device 29208 may be improved. The model may determine one or more parameters of wearable device 29208 that may be adjusted to improve the operation of wearable device 29208. The model may determine that a wearable control program, which may be a firmware associated with wearable device 29208, may be created, updated, or modified to improve an operational of the wearable device 29208.

Machine learning 29218 may determine train a model using data collection 29200 and may deploy that model to wearable device 29208 to improve an operational of wearable device 29208, such as an ability of wearable device 29208 to predict a surgical complication and/or measure one or more biomarkers.

Machine learning 29218 may prepare data from data collection 29200 (which may be processed by aggregation and filtering 29214). For example, machine learning 29218 use one or more machine learning algorithms to prepare data for contextual transform 29222, computational data collection 29226, patient analysis 29224, wearable control programs 29220, and AI models 29216.

In an example, machine learning 29218 may create a data field and appending it to each data record in a dataset. The data field may indicate whether there was a surgical bleeding complication during a respective surgical procedure derived from surgical data from collected from surgical systems & surgical devices 29204. The data field may serve as a desired output label for training a surgical wearable AI model, such as a model from AI models 29216 and/or machine learning 29218, with supervised machine learning for adjusting a wearable control program 29220, which may be deployed to wearable device 29208.

Machine learning 29218 may perform model training, model validation, model testing for a wearable device AI model and/or a wearable control program associated with wearable device 29208. For example, machine learning 29218 may train a decision tree algorithm-based wearable AI model. Those of skill in the art will recognize any other suitable machine learning algorithm may be used to build and/or train a model. The model may learn a pattern (e.g., among other patterns) that a surgical bleeding complication occurs (e.g., at a dissection/mobilization procedure step) when at least two condition occur as part of a patent analysis process, such as may occur with patient analysis 29224. A condition may be that pre-surgical data from wearable device 29208 may indicate at least one of a heart rate elevated above a threshold, blood pressure above a threshold, blood pH below a threshold, or an edema measurement above a threshold. A condition may be that surgical data from wearable device 29208 conform another conditional identified using the pre-surgical data.

AI models 29216 may be a database of one or more models. AI models 29216 may be a software module that may execute one or more models. AI models 29216 may include one or more models that may have been created, generated, and/or determined by machine learning 29218. Ai models 29216 may include one or more models that may have been or may be trained by machine learning 29218. AI models 29216 may include one or more models that may be deployed to machine learning 29218, wearable device 29208, surgical systems & surgical devices 29204, and sensing systems, 29202.

AI models 29216 may include models that may be specific to a context. For example, AI models 29216 may include a first model that may predict a surgical complication for a patient with high blood pressure and AI models 29216 may include a second model that may predict a surgical complication for a patient with normal blood pressure.

Machine learning 29218 may be configured to update to wearable control program 29220, which may be sent to wearable device 29208. Machine learning 29218 may run a model that may determine that the wearable control program associated with 29208 may need to be updated to monitor a patient to detect and/or prevent a surgical complication. For example, the model may determine that a surgical procedure (e.g., a sigmoid colectomy procedure) may have entered a dissection/mobilization procedure step. It may be determined that the wearable control program associated with wearable device 29208 may be updated to increase a data sampling rate (e.g., from once per minute to once per second). The update to the wearable control program may be generated by machine learning 29218 and/or by wearable control programs 29220 and may be sent to wearable device 29208. The update to may be to increase the data sampling rate (e.g., from once per minute to once per second). Machine learning 29218 may be configured to send an update to a second wearable control program for a second wearable device (e.g., configured for measuring biomarkers for determining tissue thickness irregularities) when the sigmoid colectomy procedure is detected to have entered an access procedure step. The update to the second wearable control program may be to decrease the data sampling rate (e.g., from once per five seconds to once per minute).

When an AI model has been deployed to a wearable device (e.g., as a part of machine learning 29218 in production) biomarker measurement data related to a surgical complication (e.g. bleeding complications) may be sent to the HCP 29212 to equip the HCP 29212 with more relevant data to prevent/mitigate potential bleeding complications. Additionally, such the AI model may prevent biomarker measurement data that may be unrelated to bleeding complications from being reported to reduce distractions by less relevant data to the HCP 29212.

Patient analysis 29224 may include an analytical model. The analytical model may include computer implemented software, a series of parameters, or a probability, for example. The analytical model may include an artificial intelligence model. The artificial intelligence model may be trained. For example, the AI model may be trained at machine learning 29218. The analytical model may be trained to recognize patterns within a dataset, such as the data collection. The analytical model may be deployed. The analytical model may be deployed to apply the recognized patterns to data, such as biomarkers, to improve performance without human guidance. The analytical model may be deployed as a computer implemented program. The analytical model may be deployed as a part of a larger computing system. The analytical model may be deployed with a model performance parameter.

In an example, the analytical model may be deployed to an embedded device, such as a wearable. The analytical model may analyze received data, such as incoming patient data. The analytical model may perform an analysis. The analytics model may perform an analysis based on the received patient data. The analysis may generate an output, including but not limited to, a diagnosis, a notification, surgical complication, and the like. For example, a wearable may use an analytics model to analyze incoming heart rate data. The wearable may determine the heart rate indicates sepsis based on the analytics model and the heart rate data. The wearable may send a notification to the HCP based on the indicated sepsis.

Figure 14:
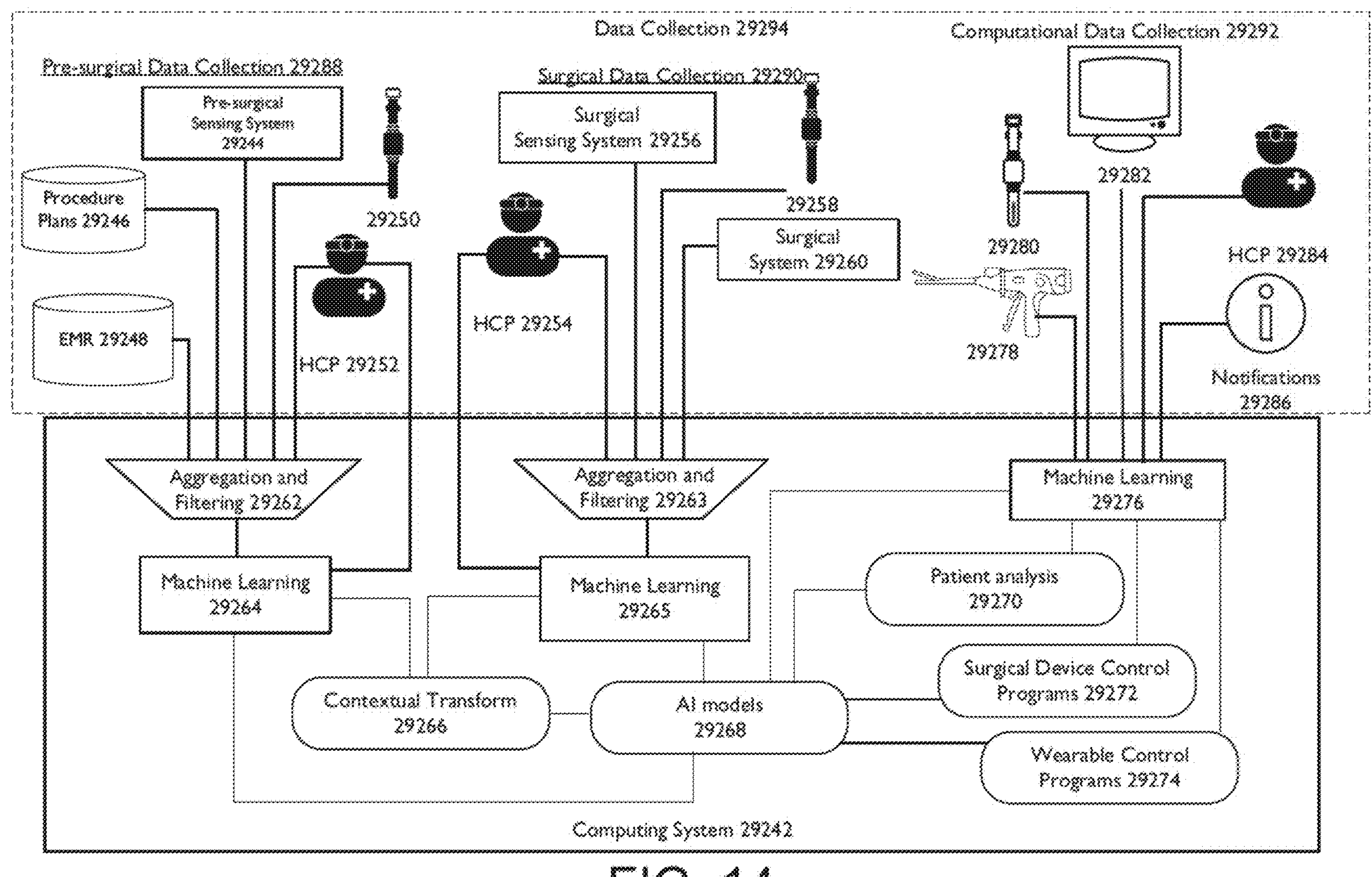
FIG. 14 depicts a block diagram for applying machine learning to improve artificial intelligence algorithms and/or iterations of learning for artificial intelligence algorithms.

FIG. 14 depicts a block diagram for applying machine learning to improve artificial intelligence algorithms and/or iterations of learning for artificial intelligence algorithms. The computing system 29242 may include computing hardware including a processor, memory, input/output sub-systems, and the like. The processor may be configured (via application specific hardware, software, firmware, or the like) to transform received data and to derive contextualized for output. For example, the processor may include a microprocessor, a microcontroller, a FPGA, and an application-specific integrated circuit (ASIC), a system-on-a-chip (SOIC), a digital signal processing (DSP) platform, a real-time computing system, or the like. For example, processor may be configured to implement computing functions and/or modules as disclosed herein. For example, the processor may be configured for aggregation and/or filtering 29262, aggregation and/or filtering 29263, machine learning 29264, machine learning 29265, machine learning 29276, contextual transform 29266 (e.g., including real-time intra-operative processing), artificial intelligence models 29268, patient analysis 29270, surgical device control programs 29272, wearable control programs 29274, and the like.

The computing system 29242 may be any device suitable for processing sensor, health record data, user input, and the like, to transform the data and derive computational data for output. The computational output may include a sensor measurement. The computational output may include contextual information or a context, for example, which may include additional information relevant to the present understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins.

The computing system 29242 may be incorporated into the system 29240 with any method suitable for implementation of the functionality disclosed herein. For example, the computing system 29242 may be incorporated as a stand-alone computing system. For example, the computing system may be incorporated into a surgical hub, such as that disclosed in FIG. 1. For example, the computing system 29242 may be incorporated into a sensing system itself (e.g., sensing both pre-surgical and surgical data and providing contextualized data as an output). For example, the computing system 29242 may be incorporated into a surgical device itself (receiving both pre-surgical and surgical data and providing contextualized data, computational data, and/or alerts as an output).

A data collection, such as data collection 29294 may be provided. Machine learning may use the data collection, such as data collection 29294. Data collection 29294 may be used by machine learning to train a model, verify a model, create a model, determine a model, and the like.

Data collection 29294 may include one or more data sources. For example, data collection 29294 may include pre-surgical data collection 29290, surgical data collection 29290, and computational surgical data 29292. Data collection 29294 may include one or more biomarkers. The one or more biomarkers may come from one or more computing systems, surgical sensing systems, wearable devices, displays, surgical instruments, surgical devices, sensor systems, devices, and the like. The data collection 29294 may include electronic medical records for a patient, data for a patient, data for other patients, data regarding past procedures, data regarding research for procedures, medical data, instructions from a health care provider, plans for a surgery, and the like.

Data collection may include data from a number of different sources. For example, the sources may include procedure plans database 29246, EMR 29248, pre-surgical sensing system 29244, wearable device 29250, data from health care provider 29252, surgical sensing system 29256, health care provider 29254, wearable device 29258, surgical system 29260, wearable device 29280, surgical instrument 29278, human-interface device 29282, data from health care provider 29284, and data related to notifications 29286.

Data collection 29294 may include pre-surgical data collection 29288. Pre-surgical data collection 29288 may include data from one or more data sources. Pre-surgical data collection 29288 may include data that is related to a patient that may be recorded prior to a surgery. Pre-surgical data collection 29288 may include one or more biomarkers they may have been recorded for a patient prior to a surgery. For example, a heart rate and blood glucose level for a patient may be recorded for a patient prior to a surgery.

Pre-surgical data collection 29288 may include data from pre-surgical sensing system 29244. Pre-surgical sensing system 29244 may include any configuration of hardware and software devices suitable for sensing and presenting patient parameters and/or biomarkers that may be relevant before, during, or after a surgical procedure. Such a pre-surgical sensing system 29244 may include any of the sensing and monitoring systems disclosed herein, including uncontrolled patient monitoring systems, controlled patient monitoring systems, and the like. For example, pre-surgical sensing system 29244 may include a wearable patient sensor system. The pre-surgical sensing system 29244 may provide data suitable for establishing baselines of patient biomarkers for use in contextual determination during and/or after surgery. The pre-surgical sensing system 29244 may provide data suitable for establishing baselines of patient biomarkers for use in making predications and/or creating computational data. The pre-surgical sensing system 29244 may incorporate or be incorporated into the sensing system 20001 as shown in FIG. 1B.

Pre-surgical data collection 29288 may include data from wearable device 29250. Wearable device 29250 may include any configuration of hardware and software devices suitable for sensing and presenting patient parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at home for four weeks prior to a surgical procedure. And/or, via a controlled patient monitoring system, a HCP may monitor the same and/or analogous biomarkers using facility equipment during time the patient is prepped immediately before the surgical procedure. For example, the wearable device 29250 may provide data suitable for establishing baselines of patient biomarkers for use in contextual determination and/or for use in creating computational data. Wearable device 29250 may include any of those disclosed herein, such as those with reference to FIG. 1B for example.

Pre-surgical data collection 29288 may include procedure plans 29248. Procedure plans 29248 may include any data source relevant to a health procedure (e.g., relevant to a health procedure in view of a particular patient and/or facility). Procedure plan 29248 may include structured data indicative of the desired end result, the surgical tactics to be employed, the operation logistics, and the like. Procedure plan 29248 may include an accounting of the equipment to be used and/or the techniques to be used. Procedure plan 29248 may include an order. Procedure plan 29248 may include a timeline. The structured data may include defined fields and/or data tags associated corresponding values. The structured data may include codes associated with surgical steps.

Pre-surgical data collection 29288 may include EMR 29248. EMR 29248 may include any data source relevant to a patient in view of a health procedure, such a surgical procedure. EMR 29248 may include information such as allergies and/or adverse drug reactions, chronic diseases, family medical history, illnesses and/or hospitalizations, imaging data, laboratory test results, medications and dosing, prescription record, records of surgeries and other procedures, vaccinations, observations of daily living, information collected by pre-surgical sensing system 29244, information collected by wearable device 29250, and the like.

Pre-surgical data collection 29288 may include data from a pre-surgical healthcare provider, such as HCP 29252. Data from HCP 29252 may include any data relevant to a pre-surgical sensing system, a patient record, a procedure plan, and the like. Data from HCP 29252 may include data that may be relevant to an operation, configuration, and/or management of a computing system, such as computing system 29242. For example, data from HCP 29252 include feedback that may be provided to a machine learning module, such a machine learning module 29264. The data from HCP 29252 may include manually entering data that may not be received directly for a relevant source (such as manually entering a manually taken biomarker reading, for example).

Data collection 29294 may include surgical data collection 29290. Surgical data collection 29290 may include data from one or more data sources. Surgical data collection 29290 may include data that may be related to a patient that may be recorded during a surgery. Surgical data collection 29290 may include one or more biomarkers they may have been recorded for a patient during a surgery. For example, a heart rate and blood glucose level for a patient may be recorded for a patient during a surgery.

Surgical data collection 29290 may include one or more data sources. Surgical data collection 29290 may include data from surgical sensing system 29256, HCP 2954, surgical system 29260, and wearable device 29258.

Surgical data collection 29290 may include data from surgical sensing system 29256. Surgical sensing system 29256 may include any configuration of hardware and software devices suitable for sensing and presenting parameters patient biomarkers that may be relevant during a surgical procedure. Surgical sensing system 29256 may include the sensing and monitoring systems disclosed herein, including controlled patient monitoring systems, surgeon monitoring systems, environmental sensing systems, and the like.

Surgical data collection 29290 may include data from surgical sensing system 29256. Surgical sensing system 29256 may include any configuration of hardware and software devices suitable for sensing and presenting parameters patient biomarkers that may be relevant during a surgical procedure. Surgical sensing system 29256 may include one or more of the sensing and monitoring systems disclosed herein, including controlled patient monitoring systems, surgeon monitoring systems, environmental sensing systems, and the like.

Surgical data collection 29290 may include data from wearable device 29258. Wearable device 29258 may include any configuration of hardware and software devices suitable for sensing and presenting patent parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at during a surgical procedure. And/or, via a controlled patient monitoring system, a healthcare provider may monitor the same and/or analogous biomarkers using facility equipment during time of the surgical procedure. For example, the wearable device 29258 may provide data suitable for use in a contextual determination and/or in a creation of computational data. Wearable device 29258 may include any of those disclosed herein, such as those with reference to FIG. 1B for example.

Surgical system 29260 may include any surgical equipment suitable for providing operative data regarding its configuration, use, and/or present condition and/or status, for example. Surgical system 29260 may include equipment in the surgical theater. Surgical system 29260 may include any equipment employed in the surgical theater, such as that disclosed with reference to FIG. 1, FIG. 7A, FIG. 10, and throughout the present application, for example. The surgical system 29260 may include surgical fixtures of a general nature, such as a surgical table, lighting, anesthesia equipment, robotic systems, and/or life-support equipment. Surgical system 29260 may include surgical fixtures that may be related to the procedure at-hand, such as imaging devices, surgical staplers, energy devices, endocutter clamps, and the like. For example, surgical system 29260 may include be one or more of a powered stapler, a powered stapler generator, an energy device, an energy device generator, an in-operating-room imaging system, a smoke evacuator, a suction-irrigation device, an insufflation system, or the like.

The surgical system 29260 may include at least one of a surgical instrument, surgical visualization system, monitor, sound system, energy devices, a wearable, and the like. For example, the surgical system may include a surgical hub. For example, the surgical system may include a surgical stapler. For example, the surgical system may include an endocutter, for example. Data from the surgical instrument may include surgical instrument parameters. The surgical instrument parameters may include surgical instrument power, for example. Data from the surgical visualization system may include location of surgical instruments in relation to a patient surgical site and/or organ. For example, data may include the distance between a surgical stapler and a close vital organ.

Surgical data collection 29290 may include data from a surgical HCP, such as HCP 29254. Data from HCP 29254 may include any data relevant to a surgical sensing system, a wearable device, a surgical system, a machine learning, a patient analysis, a surgical device control program, a wearable control program, a contextual transform, an artificial intelligence model, and the like. For example, HCP 29254 may provide data that may be associated with surgical system 29260, wearable device 29258, surgical sensing system 29256, machine learning 29265, and the like. For example, the HCP 29254 may provide data that may trigger an interaction with the context transform 29266 and/or machine learning 29265. The data from HCP 29254 may include manually entering data not received directly for any relevant source (such as manually entering a manually taken biomarker reading, for example).

The data received from the pre-surgical data sources, such as pre-surgical data collection 29288, may be subject to aggregation and/or filtering 29262. Aggregation and/or filtering 29262 may perform pre-processing on data received from pre-surgical data collection 29288. The data received from the surgical data sources, such as surgical data collection 29290, may be subject to aggregation and/or filtering 29263. Aggregation and/or filtering 29263 may perform per-processing on data received from surgical data collection 29290. Aggregation and/or filtering 29262 and aggregation and/or filtering 29263 may be used to prepare and format the data for use by computing system 29242. For example, aggregation and/or filtering 29262 and aggregation and/or filtering 29263 may prepare data to be processed by machine learning 29264, machine learning 29265, machine learning 29276, contextual transform 29266, artificial intelligence models 29268, surgical device control programs 29272, and wearable control programs 29274.

Processing the data received from the pre-surgical data collection 29288 by aggregation and/or filtering 29262 may include filtering (e.g., to select sensor data from the stream of data from pre-surgical sensing system 29244). Aggregation and/or filtering 29262 may use filtering to help reject noise in data from pre-surgical data collection 29244. Aggregation and/or filtering 29262 may use a method to establish a baseline for a biomarker from pre-surgical data collection 29288. Aggregation and/or filtering 29262 may perform time mapping on data from pre-surgical data collection 29288 (e.g., to place received values from different sources in alignment with each other in regard to time). Time mapping may aid in correlation and ratio analysis, which may occur in contextual transform 29266.

Aggregation and/or filtering 29262 may translate data from pre-surgical data collection 29288. The translation of data may include coordinating formats, coordinating data types, translating from one format to another format, translating from one data type, to another data type, accounting for a difference between a data source data format, and accounting for a data type expected by another module, such as machine learning 29264. Translating may include translating the data into a format suitable for machine learning, for artificial intelligence models, for patient analysis, for use by a surgical device control program, and/or for use by a wearable control program. Data from the pre-surgical data collection 29288 may be translated into a notification for display, such as display on a human-interface device 29282. Data from pre-surgical data collection 29288 may be translated into a setting for the surgical device 29278. Data from surgical collection 29290 may be translated into data that may be included and/or used for notifications 29287.

Processing the data received from surgical data collection 29290 by aggregation and/or filtering 29263 may include filtering (e.g., to select sensor data from the stream of data from surgical system 29260). Aggregation and/or filtering 29263 may use a method to establish a baseline for a biomarker from surgical data collection 29290. Aggregation and/or filtering 29263 may use filtering to help reject noise in data from surgical data collection 29290. Aggregation and/or filtering 29263 may perform time mapping on data from surgical data collection 29290 (e.g., to place received values from different sources in alignment with each other in regard to time). Time mapping may aid in correlation and ratio analysis, which may occur in contextual transform 29266.

Aggregation and/or filtering 29263 may translate data from surgical data collection 29290. The translation of data may include coordinating formats, coordinating data types, translating from one format to another format, translating from one data type, to another data type, accounting for a difference between a data source data format, and accounting for a data type expected by another module, such as machine learning 29265. Translating may include translating the data into a format suitable for machine learning, for artificial intelligence models, for patient analysis, for use by a surgical device control program, and/or for use by a wearable control program. Data from the surgical data collection 29290 may be translated into a notification for display, such as display on a human-interface device 29282. Data from surgical data collection 29290 may be translated into a setting for the surgical device 29278. Data from surgical collection 29292 may be translated into data that may be included and/or used for notifications 29287.

Contextual transform 29266 may operate to provide a context for data, such as pre-surgical data collection 29288 and/or surgical data collection 29290. For example, contextual transform 29266 may transform data into contextualized surgical data, which may be included in computational data collection 29292. To illustrate, as an input the contextual transform may receive surgical data that includes, for example, a measurement time, a sensor system identifier, and a sensor value. Contextual transform 29266 may output contextualized surgical data. Contextual transform 29266 may output data that may be modified and/or enhanced by machine learning 29264, machine learning 29265, machine learning 29276, patient analysis 29270, surgical device control programs 29272, wearable control programs 29274, and artificial intelligence models 29268.

Contextual transform 29266 may determine and/or store data that may be related to each other. Contextual transform 29266 may determine how data may be related to each other. For example, contextual transform 29266 may determine that data from surgical data collection 29290 may be related to data from pre-surgical data collection 29290. Contextual transform 29266 may determine a context for the data. Context, for example, additional information relevant to the present understanding and/or interpretation of the sensor measurement.

Computational data collection 29292 may include data that may be generated, created, determined, and/or computed by computing system 29242. For example, computational data collection 29292 may include models output from machine learning, data generated by machine learning, biomarkers processed by computing system 29242, augmented data, predictive probabilities, firmware, firmware updates, parameters for surgical devices, surgical device control program, updates to surgical device control programs, wearable control programs, parameters for wearable devices, parameters for controlling surgical devices, electronic medical records, contextual data, contextual surgical data, notifications, requests for feedback, messages to healthcare providers, and the like.

Computational data collection 29292 may include context, for example, additional information relevant to the present understanding and/or interpretation of the sensor measurement. For example, the context may include presurgery and/or pre-therapy baselines. For example, the context may include situational awareness of incorrectly connected and/or incorrectly operating surgical and/or sensing systems. For example, the context may include adjustments to products, surgical plans, and/or margins. Computational data collection 29292 may include data sent to or received from surgical device 29278, wearable device 29280, human-interface device 29282, health care provider 29284, and notifications 29286. Computational data collection 29292 may be created, modified, received by and/or sent by machine learning 29264, machine learning 29265, machine learning 29276, contextual transform 29266, artificial intelligence models 29268, patient analysis 29270, surgical device control programs 29272, wearable control programs 29274, and/or any combination thereof.

Computational data collection 29292 may include data that provides a context. The context may include additional information that may place a biomarker into a specific context for the healthcare providers. For example, computational data collection 29292 may include instructions and/or information about a baseline value for a sensor value, an alert of a deviation, relevant information from the patient's record, relevant information to a procedural element of the surgery, surgical device settings, and/or any information the healthcare provider might find relevant to have at the moment of the sensor's measurement itself. The context may be determined by machine learning, such as by machine learning 29264, machine learning 29265, and/or machine learning 29276. Computational data collection 29292 may include one or more data tags. The data tags may include logging data (indicating that that a specific transform or other processing has occurred).

Computational data collection 29292 may include data that may be provided by HCP 29284. For example, HCP 29284 may provide feedback regarding data provided by machine learning 29276. Computational surgical data 29292 may include data that may be sent to HCP 29284. For example, HCP 29284 may receive data provided by machine learning 29276. Data from HCP 29284 may include any data relevant to a surgical sensing system, a wearable device, a surgical system, a machine learning, a patient analysis, a surgical device control program, a wearable control program, a contextual transform, an artificial intelligence model, and the like. For example, HCP 29284 may provide data that may be associated with surgical device 29278, wearable device 29280, a patent, human-interface device 29282, notifications 29286, computing system 29242, and/or any combination thereof. For example, the HCP 29284 may provide data that may trigger an interaction with the context transform 29266 and/or machine learning 29276. The data from HCP 29284 may include manually entering data not received directly for any relevant source (such as manually entering a manually taken biomarker reading, for example).

Human-interface device 29282 may include any device suitable for producing a perceptible representation of computational data, such as computational data collection 29292. The perceptible representation may include a visual indication, an audible indication, or the like. The human-interface device 29282 may include a computer display. For example, the human-interface device 29282 may include a visual representation including text and/or images on a computer display. The human-interface device 29282 may include a text-to-speech device. For example, the human-interface device 29282 may include synthesized language prompt over an audio speaker. The human-interface device 29282 may communicate the computational data to the surgeon and/or surgical team. The human-interface device 29282 may include and/or be incorporated into any suitable device disclosed herein. For example, the human-interface device 29282 may include and/or be incorporated into any of the primary display 20023, a first non-sterile human interactive device 20027, and/or a second non-sterile human interactive device 20029, such as that disclosed in FIG. 2A for example. For example, the human-interface device 29282 may include and/or be incorporated into a human interactive device 20046, such as that disclosed in FIG. 2B. For example, the human-interface device 29282 may include and/or be incorporated into the display 20224 of a surgical instrument, such as that disclosed in FIG. 7A for example.

The notifications 29286 may include any device suitable for generating a perceptible indication that relevant computational data is available and/or has changed. The indication may include a visual indication, an audible indication, a haptic indication, and the like. The notifications 29286 may incorporate any of the human-interface devices 27020 disclosed here. The notifications 29286 may include non-verbal and/or non-textual indications to represent contextual data is available and/or has changed. For example, the alert system may include audio tones, visual color changes, lights, and the like. For example, the notification may include a haptic tap on a wearable device, such as a smartwatch worn by the surgeon. Notifications 29286 may include computational data, pre-surgical data, surgical data, and/or post-surgical data. Notifications 29286 may include a request from a machine learning algorithm for a HCP to provide feedback regarding data, a recommendation, an accuracy of an artificial intelligence model, an accuracy of training data, an accuracy of machine learning, a diagnosis, an indication of a problem, data generated by machine learning, a patient analysis, a conclusion regarding a patient analysis, a modification to a surgical device control program, a surgical device control program, wearable control program, any combination thereof, and the like. For example, notifications 29286 may request that HCP 29284 provide feedback regarding a surgical device control program that may be sent to surgical device 29278.

The surgical device 29278 may include any equipment employed for a surgical procedure (such as surgical systems 29260) that may have a configurable aspect to its operation. The configurable aspect of the equipment may include any adjustment or setting that may influence the operation of the equipment. For example, surgical device 29278 may have software and/or firmware adjustable settings. Surgical device 29278 may be hardware and/or structurally adjustable settings. In an example, the surgical device 29278 may report its present settings information to the computing system 29242. In an example, the surgical device 29278 may include an artificial intelligence model that may be deployed by computing system 29242, trained at computing system 29242, modified by computing system 29242, any combination thereof, and the like.

Example device settings for surgical device 29278 may include placement, imaging technology, resolution, brightness, contrast, gamma, frequency range (e.g., visual, near-infrared), filtering (e.g., noise reduction, sharpening, high-dynamic-range), and the like for imaging devices; placement, tissue precompression time, tissue precompression force, tissue compression time, tissue compression force, anvil advancement speed, staple cartridge type (which may include number of staples, staple size, staple shape, etc.), and the like for surgical stapling devices; and placement, technology type (such as harmonic, electrosurgery/laser surgery, mono-polar, bi-polar, and/or combinations of technologies), form-factor (e.g., blade, shears, open, endoscopic, etc.) coaptation pressure, blade amplitude, blade sharpness, blade type and/or shape, shears size, tip shape, shears knife orientation, shears pressure profile, timing profile, audio prompts, and the like for energy devices, for example.

Computational data collection 29292 may include data from wearable device 29280. Wearable device 29280 may include any configuration of hardware and software devices suitable for sensing and presenting patent parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at during a surgical procedure. And/or, via a controlled patient monitoring system, a healthcare provider may monitor the same and/or analogous biomarkers using facility equipment during time of the surgical procedure. For example, the wear able device 29280 may provide data suitable for use in a contextual determination during and/or after surgery. Wearable device 29280 may include any of those disclosed herein, such as those with reference to FIG. 1B for example.

Computational data collection 29292 may include a wearable control program that may have been sent by wearable control programs 29274 wearable device 29280. Computational data collection 29292 may include an artificial intelligence model that may be sent to wearable device 29280.

The machine learning module 29264 may perform data preparation as described herein with the pre-surgical data collection 29288 (e.g., a dataset). In an example, the data preparation may further include the machine learning module 29264 receiving input from an HCP 29252 labeling a subset of the data records in the dataset for training a pre-surgical patient analysis model (e.g. a training dataset). The pre-surgical patient analysis model may stored at and/or or included within AI model 29268. The pre-surgical patient analysis model may be a training data set with supervised machine learning for patient analysis 29270 (e.g., a probability of surgical complications during a surgical procedure). For example, machine learning 29264 may receive data to from pre-surgical data collection 29288 that may be used to train a model that may be stored at AI model 29268 and may be deployed at patient analysis 29270.

Those of skill in the art will recognize any suitable machine learning algorithm may be used to build the model 29268. For example, the input from HCP 29252 may include a "high risk" label when a patient's data record from patent records 29248 indicates a risk of surgical complications related to adhesions due to a history of multiple prior colorectal surgical procedures and pre-surgical biomarker measurement data from a pre-surgical sensing system 29244 or a wearable device 29250 indicating a probability of presence of chronic inflammation response. For example, the input from HCP 29252 may include a "medium risk" label when a patient's data record indicates a risk of surgical complications related to adhesions due to a history of multiple prior colorectal surgical procedures without any indication from pre-surgical biomarker measurement data that there is a probability of presence of chronic inflammation response. For example, the input from HCP 29252 may include label "low risk" a when a patient's data record indicates a risk of surgical complications related to adhesions due to a history of a single prior colorectal surgical procedure without any another indication of a probability of adhesion. The labels provided by HCP 29252 may be machine learning 29264 to train one or more models that may be used for patient analysis, modification and/or creation of surgical device control programs, and modification and/or creation of wearable control programs. The model may be stored at AI models 29268 and may be deployed at machine learning 29264, patient analysis 29270, surgical device control programs 29272, and/or warble control programs 29274.

Further, the input from HCP 29252 may include a notification level setting associated with each high-risk label, medium-risk label, or low-risk label. For example, a notification level setting may used by machine learning module 29264 to train a model to send a notification to HCP 29252 and/or HCP 29284 when the model may predict a high risk of surgical complication. In an example, a notification level may be used by the model when deployed at machine learning 29264 to send a notification to HCP 29252 when the model predicts a high risk of surgical complication. The HCP 29252 may respond to the notification with feedback, and the model may further be trained using the feedback. In an example, a notification level may be used by the model when deployed at patient analysis 29270 to send a notification to HCP 29284 and/or notifications 29286 when the model predicts a high risk of surgical complication. The HCP 29284 may respond to the notification with feedback, and the model may further be trained using the feedback.

The data preparation may also include the machine learning module 29264 receiving input from an HCP 29252 labeling a second subset of the data records in the dataset for validating a model (e.g., a validation dataset) with supervised machine learning.

The machining learning process 29264 may perform model training for the model. The machining learning process 29264 may perform model validation with the validation dataset after model may be deem trained (e.g., when a neutral network-based model's cost function has reached a global minimum).

Upon completing model validation, the machine learning module 29264 may perform model testing using a third subset of the data records in the dataset (e.g., an unlabeled dataset) for testing a model. The machine learning module 29264 may send predictions produced by the model to HCP 29252 for verification and/or HCP 29284. For example, the model may predict a high risk of surgical complication and an associated notification level of high-risk surgical complications. The machine learning module 29264 may send the high-risk prediction, notification level of high risk only, and decision points that may have led to such prediction (e.g., from the model 29268 trained with a decision tree machine learning algorithm).

In an example, based on the training dataset labeled by the HCP 29252, the model that may have been trained with a decision tree machine learning algorithm may learn a pattern (e.g., among other patterns) that a high-risk level of surgical complications may correlate with the combination of three or more prior colorectal surgical procedures and pre-surgical measurement data for at least one biomarker associated with a probability of chronic inflammation response (e.g., a high skin conductance level, a low tissue oxygenation level, and the like). Such a pattern may be a decision point in a decision tree algorithm-based model. The machine learning module 29264 may send a decision point along with the high-risk prediction and the notification level of high risk to the HCP 29252 and/or HCP 29284. machine learning module 29264 may send a decision point along with the high-risk prediction and the notification level of high risk to notifications 29286. In response, the HCP 29252 and/or HCP 29284 may provide a response verifying that the prediction is accurate. The verification may contribute to a success metric for meeting an accuracy parameter for deploying the model in a production environment (e.g. may be used on patients without supervision). A response from the HCP 29252 and/or HCP 29284 indicating the predication may be inaccurate may contribute to a failure metric for preventing model deployment due to inaccurate model predictions (e.g. may be used on patients with supervision).

The machine learning module 29264 may output the decision tree from the model. For example, the decision tree may be stored in AI models 29268. The decision tree may be sent to HCP 29252 and/or HCP 29284 to allow the decision tree to be verified holistically as opposed to one predication at a time.

Upon successful model testing with the test dataset, the computing system 29242 may deploy the model to a production environment production. For example, the model may be deployed to machine learning 29264, machine learning 29265, machine learning 29276, and patient analysis 29270. The deployed model 29268 may be further improved (e.g., for patient analysis purposes) in production. For example, patient analysis 29270, machine learning 29264, and/or machine learning 28276 may use feedback from a HCP to improve the model.

For example, the model may produce false negative predictions and/or false positive predictions. Feedback for such false negative and/or false positive predictions may be sent to the machine learning module 29276. In an example, the model may incorrectly predict a high risk of surgical complication. When the machine learning module 29276 sends an associated notification 29286, which may be sent to HCP 29284, the HCP 29284 may provide a response to the machine learning module 29276 indicating the prediction is a false positive. In such case, the machine learning module 29276 may not update the model threshold for predicting a positive prediction for surgical complications. The model may be stored and/or updated in AI models 29268 such that another deployment of the model may benefit from the feedback improvements.

In an example, the model may incorrectly predict no risk of a surgical complications. The machine learning module 29276 may fail to send a notification, such as notifications 29286, to HCP 29284. HCP 29284 may not be provided with an opportunity to provide feedback. In such a case, the machine learning module 29276 may detect the error by checking the model prediction against the surgical outcome data from surgical system 29260 (e.g., which may be a surgical hub). The machine learning module 29276 may lower the model threshold for predicting a positive prediction for surgical complications to reduce the possibility of predicting false negatives. The model may be stored and/or updated in AI models 29268 such that another deployment of the model may benefit from the feedback improvement and/or detection of the error.

The machine learning module 29265 may perform data preparation as described herein with the surgical data collection 29290 (e.g., a dataset) for creating and training a model, which may be a surgical device control program model. The model may be stored and/or deployed at AI models 29268. The model may be deployed at machine learning 29265, machine learning 29276, and/or surgical device control programs 29272. In an example, the data preparation may further include creating a data field and appending it to a (e.g., each) data record in the dataset. The data field may indicate whether there was a surgical complication during a respective surgical procedure derived from surgical data from collected from a surgical system 29260 (e.g., a surgical hub). The data field may indicate whether an operation of a surgical device or a wearable device may be improved (e.g. the device may have sub-optimally operated). The data field may serve as a desired output label for training the model with supervised machine learning for improving a model and/or a surgical device control program that may be determined and/or deployed at device control program 29272 to improve a surgical outcome. For example, the model may be deployed at surgical device control program 29272 and may be used to improve a surgical device program associated with surgical device 29278.

The machine learning module 29265 may perform model training, model validation, model testing for an artificial intelligence algorithm that may be used to create a model, such as a decision tree algorithm model. Those of skill in the art will recognize any other suitable machine learning algorithm may be used to build the model. The model may learn a pattern (e.g., among other patterns) that a surgical complication (e.g., a bleeding complication) occurs when a first condition and a second condition occur. The first condition may be that data from surgical sensing system 29256 and/or wearable device 29258 indicates at least one of: heart rate elevated above a threshold A, blood pressure above a threshold B, blood pH below a threshold C, or an edema measurement above a threshold D. The second condition may be that a control program associated with surgical device 29278 (e.g., a linear stapler) may be configured to compress tissue with a compression force below a threshold E. The model may learn another pattern (e.g., among other patterns) that a surgical complication (e.g., a bleeding complication) does not occur when the first condition and the second condition occur. A third condition may be that a control program associated with surgical device 29278 (e.g., a linear stapler) may be configured to compress tissue with a compression force above the threshold E.

Upon model testing using a test dataset, the computing system 29242 may deploy model to a production environment as a part of the machine learning module 29276. For example, the model may be deployed at machine learning 29264, machine learning 29265, machine learning 29276, AI models 29268, patient analysis 29272, surgical device control programs 29272, and/or wearable control programs 29274. During an operation in production, the model may detect a data pattern that the model may have learned during model training. For example, the model may receive input data indicating heart rate elevated above threshold A and indicating that a control program for surgical device 29278 is configured to apply a compression force below threshold E. In response, the model may predict a surgical complication and the machine learning module 29276 may update a deployed model, may update a model for generating a surgical device control program, may send updated parameters to the surgical device, or may send an updated surgical device control program to the surgical device to, for example, increase the compression force to be above threshold E.

The machine learning module 29265 may perform data preparation as described herein for creating and training a model, which may be a model for a wearable device such as wearable device 29258, using the pre-surgical data collection 29288 (e.g., a pre-surgical dataset) and the surgical data collection 29290 (e.g., a surgical dataset). In an example, the data preparation may further include creating a data field and appending it to a (e.g., each) data record in the dataset. The data field may indicate whether there may have been a surgical bleeding complication during a respective surgical procedure derived from surgical data from collected from a surgical system 29260 (e.g., a surgical hub). The data field may serve as a desired output label for training the model with supervised machine learning for adjusting a wearable control program, which may be stored at wearable control program 29272 and may be deployed at wearable device 29280, for improved sensed data relevancy.

For example, the machine learning module 29265 may perform model training, model validation, model testing for a model, such as a decision tree algorithm model. Those of skill in the art will recognize any other suitable machine learning algorithm may be used to build the model. The model may learn a pattern (e.g., among other patterns) that a surgical bleeding complication occurs (e.g., at a dissection/mobilization procedure step) when at least two conditions occur. One condition may be that pre-surgical data from pre-surgical sensing system 29244 and/or wearable device 29250 indicates at least one of: heart rate elevated above a threshold A, blood pressure above a threshold B, blood pH below a threshold C, or an edema measurement above a threshold D. Another condition may be that surgical data from surgical sensing system 29256 and/or wearable device 29258 indicates at least one of: heart rate elevated above a higher threshold A' (e.g., as compared to threshold A), blood pressure above a higher threshold B' (e.g., as compared to threshold B), blood pH below a lower threshold C' (e.g., as compared to threshold C), or an edema measurement above a higher threshold D' (e.g., as compared to threshold D).

The machine learning module 29265 may be configured to send update a model for a wearable control program. For example, machine learning module 29265 may update a model that may be deployed at machine learning 29264, machine learning 29265, machine learning 29276, wearable control programs 29274, wearable device 29250, wearable device 29258, wearable device 29280 and the like. The machine learning module 29265 may be configured to update a wearable control program that may be stored and/or deployed at wearable control programs 29274, wearable device 29250, wearable device 29258, and/or wearable device 29280. For example, an update may be sent to update the wearable control program of wearable device 29280 (e.g., configured for measuring heart rate, blood pressure, blood pH, and/or edema) when a surgical procedure (e.g., a sleeve gastrectomy procedure) is detected to have entered a dissection/mobilization procedure step. The update to the wearable control program may be to increase the data sampling rate (e.g., from once per minute to once per second). During the model operation (e.g., after model deployment) as a part of the machine learning module 29276 in production, such increased data sampling rate (e.g., during the dissection/mobilization) of biomarker measurement data related to bleeding complications may be sent to the HCP 29254 and/or HCP 29284 (e.g., via device 29282) to equip the HCP 29284 with more relevant data to prevent/mitigate potential bleeding complications.

Patient analysis 29270 may include software that may be used to provide analysis on a patient. For example, the analysis may indicate a probability of a surgical complication, a probability of surgical success, a diagnosis of a disease, a probability of a disease, a probability of a patient recovery, and the like. Patient analysis 29270 may include a model. The model may be stored outpatient analysis 29270 and/or deployed at patient analysis 29270. Patient analysis 29270 may include a number of models. For example, patient analysis 29270 may include one model for high blood pressure, a second model for normal blood pressure, and the third model for patients with diabetes. A model deployed at patient analysis 29270 may be from machine learning 29264, machine learning 29265, machine learning 29276, and/or AI models 29268. Patient analysis 29270 may include computational data.

Surgical device control programs 29272 may include software that may be used to provide control programs for surgical devices. Surgical device control programs 29272 may include device control programs, such as firmware, that may be stored for surgical devices. Surgical device control programs 29272 may include one or more parameters that may be used to configure, modify, operate, or control a surgical device. Surgical device control programs 29272 may include a model. For example, surgical device control programs 29272 may store a model that may be used for a surgical device, may deploy a model that may be used for a surgical device, or may update a model that may be used for a surgical device. A model deployed at surgical device control programs 29272 may be from machine learning 29264, machine learning 29265, machine learning 29276, and/or AI models 29268. Surgical device control programs 29272 may include computational data.

Wearable control programs 29274 may include software that may be used to provide control programs for wearable devices. Wearable control programs 29274 may include device control programs, such as firmware, that may be stored for wearable devices. Wearable control programs 29274 may include one or more parameters that may be used to configure, modify, operate, or control a wearable device. Wearable control programs 29274 may include a model. For example, wearable control programs 29274 may store a model that may be used for a wearable device, may deploy a model that may be used for a wearable device, or may update a model that may be used for a wearable device. A model deployed at wearable control programs 29274 may be from machine learning 29264, machine learning 29265, machine learning 29276, and/or AI models 29268. Wearable control programs 29274 may include computational data.

Figure 15:
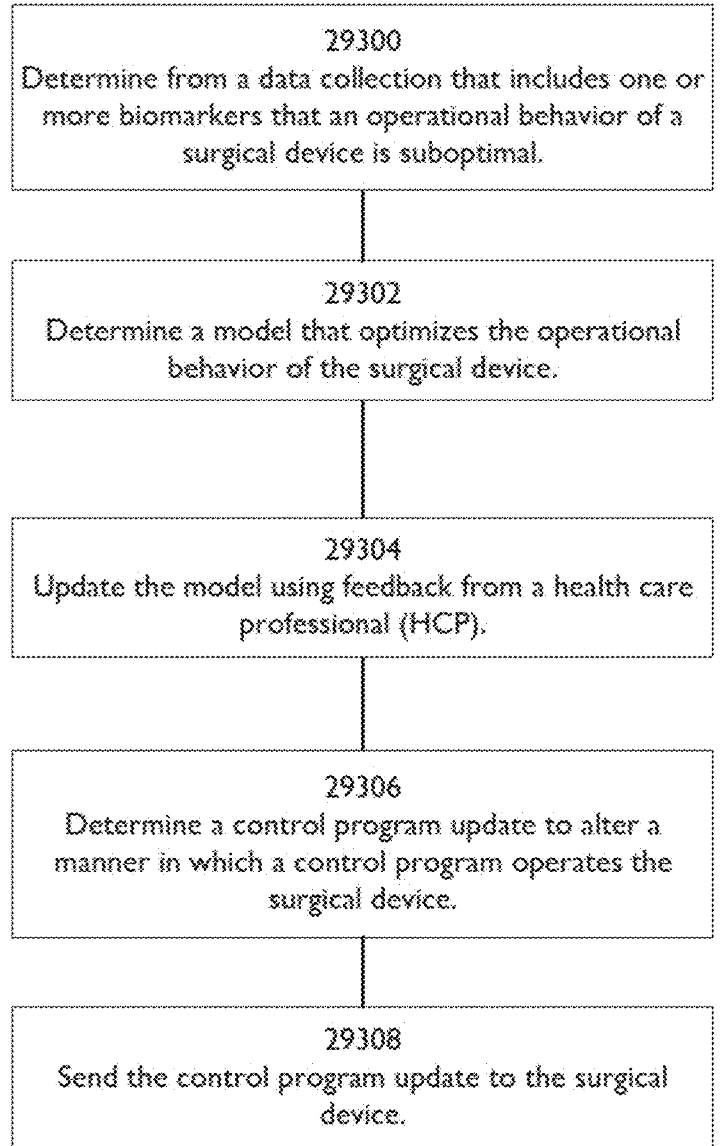
FIG. 15 depicts a method for applying machine learning to a data collection to improve a surgical outcome.

FIG. 15 depicts a method for applying machine learning to a data collection to improve a surgical outcome. The method may be implemented in a computing system. At 29300, an operational behavior of a surgical device may be determined to be suboptimal using a surgical device data and/or a biomarker from a sensing system. The operational behavior of the surgical device may be indicative of how the surgical device may potentially operate or may be operating during the operation. For example, the operational behavior of the surgical device may indicate that the surgical device is a stapler that is firing at a specific power. As another example, the operational behavior of the surgical device may indicate that the surgical device is an endocutter that may be operating at a specific parameter. The operational behavior may include one or more parameters that may control an operation of the surgical device. The operational behavior may include an indication of how the surgical device may perform, a prediction of how the surgical device may perform, an indication of how the surgical device is performing, an indication of a task being performed by the surgical device, an indication of a task being performed by a user (e.g., an HCP) holding the surgical device, and the like.

An indication that an operational behavior is suboptimal may be an indication that the operational behavior may be improved. For example, an operation of a device may be improved when there is an indication that the operational of the device is suboptimal.

The data collection may include one more biomarkers. The one or more biomarkers may be related to a patient that may be planning to go under surgery. For example, a biomarker may be a baseline heart rate for a patient. The one or more biomarkers may be related to a patient that may be undergoing surgery. For example, a surgical device may be used during the surgery on the patient and one or more biomarkers may be recorded (e.g., received from a sensing system) as the surgical device may be used. The one or more biomarkers may indicate how the surgical device may be affecting the patient. For example, it may be expected that a biomarker may be within a range when a surgical device is used. When the biomarker is outside the range, it may indicate that the surgical device may not be operating optimally. In an example, the biomarker that may be outside the range may indicate that an improvement may be made to the surgical device. In an example, the biomarker may indicate that the surgical device may be contributing to a surgical complication and the operational behavior of the surgical device may be considered suboptimal.

At 29302, a model may be determined to optimize and/or improve the operational behavior of the surgical device to improve a surgical outcome using machine learning, the surgical device data, and the biomarker. For example, the machine learning model may be trained to detect a data pattern that a second surgical device operational parameter may be correlated to an absence of a surgical complication under a physiological condition state represented by the biomarker measurement data. The model may be predictive of how a surgical device may operate, may be predictive of how a wearable device may operate, may be predictive of a surgical complication, may be predictive of a surgical outcome may be predictive of a surgical success rate, and the like. The model may diagnose a disease, for example, by indicating a probability that a disease may occur or may be occurring. The model may optimize the operational behavior of the surgical device by determining a surgical outcome and by determining one or more parameters that may be adjusted on the surgical device to improve the surgical outcome. The model may optimize the operational behavior of the surgical device by determining a surgical outcome and by determining that a control program for the surgical device may be modified, updated, and or generated to modify the operational behavior of the surgical device.

A model may be created to be trained using input data, such as surgical device operational parameters recorded during surgical procedures, biomarker measurement data recorded prior to and during surgical procedures, and surgical data such as surgical complications recorded during surgical procedures. The machine learning model may be trained to detect a data pattern that a first surgical device operational parameter may be correlated to a surgical complication under certain physiological state represented by the biomarker measurement data.

In an example, a model may be trained with data from the data collection. The model may predict one or more surgical outcomes. The model may predict one or more surgical complications. The models may be used to determine one or more parameters and/or a control program that may be used to improve and operational behavior of a surgical device to improve one or more surgical outcomes.

At 29304, the model may be updated using a feedback given by a health care processional (HCP) to improve the model. For example, the model's predictions of surgical complications and/or absence of surgical complications may be sent to an HCP for validation. In response, the HCP may provide positive or negative feedback to update the machine learning model to improve model prediction accuracy.

It may be determined that feedback from the HCP may be useful for improving the model. For example, it may be determined that data may be insufficient to provide an accurate prediction for one or more surgical outcomes. It may be determined that feedback from the HCP may be useful for improving the accuracy of a prediction for a surgical outcome. A request for feedback may be sent to the HCP. Feedback from the HCP may be received. The model may be updated using the feedback from the HCP.

At 29306, a control program update may be determined, generated, and/or configured using the model and the surgical device data to alter a manner in which a control program operates the surgical device during a surgical procedure. For example, based on the data pattern for surgical complications and the data pattern for an absence of surgical complications detected by the machine learning model, a control program update, such as an update to use the second surgical device, may be generated for the surgical device on the condition that the surgical device operational parameters and biomarker measure data during actual surgical procedures match the data pattern for surgical complications. in an an example, the control program maybe a model. The model may be associated with and or deployed on the surgical device. For example, surgical device may have artificial intelligence. It may be determined that the model on the surgical device may need to be updated to improve how the surgical device may operate. The control program update may be an improved model, training data for a deployed model, and or other data to update a model on the surgical device. For example, an improved model may be trained and the improved model may be included in a control program update such that the improved model may alter the manner in which the control program operates the surgical device.

In an example, the control program may include surgical device parameters that may change how the surgical device may operate. The surgical device may have a number of parameters that may be adjusted. By adjusting the parameters, the way in which the surgical device may operate may change. For example, the parameters may affect the firing power of a surgical stapler. As another example, the parameters may affect the power given to an endocutter. A control program update may be determined to adjust one or more parameters for the surgical device to alter the manner in which the surgical device operates.

In an example, the surgical device may include a control program, which may be firmware, that may control how the surgical device operates. For example, the control program may be software that operates the hardware on the surgical device. Updates to the control program may include parameters, updates to the firmware, optimizations to the hardware on the surgical device, optimizations to the software on the surgical device and the like. A control program update may be designed to improve, replace, update, or augment the control program that may be operating on the surgical device. For example, the control program update may be designed to provide an advanced feature that may not have been included with the control program currently operating on the surgical device. The control program update may be set to the surgical device to operate the control program on the surgical device. And the surgical device may have the advanced feature upgrade after installing the control program update.

At 29308, the control program update may be sent to the surgical device. For example, the determined control program update to use the second surgical device parameter may be sent to the surgical device for use during a surgical procedure. As another example, the control program update may update a model, a control program, and or other software that may be used by or operating on the surgical device.

A computing system and/or a method may be provided for applying machine learning to a data collection to improve a surgical outcome. The computing system may comprise a processor. The processor may be configured to perform a method and/or a number of actions. An indication may be determined. The indication may indicate that an operational behavior of a surgical device may be suboptimal or may be improved. For example, a data collection may include one or more biomarkers that may be used to determine an indication that an operational behavior of a surgical device may be suboptimal or may be improved. A model that may optimize and/or improve the operational behavior of the surgical device to improve a surgical outcome may be determined using machine learning and/or the data collection. The model may be updated using feedback given by a healthcare provider (HCP) to improve the model. A control program update may be determined and/or generated using the model and the data collection. The control program update may be configured to alter a manner in which a control program operates the surgical device during a surgical procedure. The control program update may be sent to the surgical device.

In an example, a request for feedback may be determined. The request for feedback may result in a faster learning cycle for training the model that optimize and/or improves the operational behavior of the surgical device. The request for feedback may result in a faster training cycle that may optimize and/or improve the operational behavior of the surgical device. For example, the feedback may reduce the amount of data used to train the model, may reduce the amount of time used to train the model, may reduce the amounts of information needed from a user to train the model, and the like, the request for feedback may be sent to the HCP.

In an example, it may be determined that an advanced instrument operation may reduce a complication for a patient and/or may improve a recovery rate for the patient. For example, it may be determined from the model that an advanced instrument operation may reduce a complication for a patient and/or improve a recovery rate for the patient. The control program update may be generated using the model and the data collection, for example, by altering the manner in which the control program operates the surgical device during the surgical procedure to provide the advanced instrument operation.

In an example, the model may further provide a risk level assessment and the feedback given by the HCP may further include a risk level verification that may indicate that the HCP agrees with the risk level assessment provided by the model. For example, the model may determine a risk level using one or more biomarkers for a patient and may provide the risk level 2 and HCP. The HCP may indicate that they agree with the risk level provided by the model.

In an example, the model may provide a notification level. The notification level may enable improvement in the model by seeking feedback from the HCP during the surgical procedure. The notification level may be set so as to seek feedback from the HCP without distracting the HCP during a surgery. The notification level may be set so as to prevent a surgical complication by reducing a distraction to the HCP during a surgery.

In an example, the model may provide a notification level that may reduce one or more distractions to the HCP during the surgical procedure.

In an example, the model may provide a notification level that may improve a quality of the model by seeking feedback from the HCP during the surgical procedure while minimizing one or more distractions to the HCP during the surgical procedure.

In an example, a previous model associated with the control program that may operate the surgical device during the surgery may be determined. The model that may optimize and/or improve and/or improve the operational behavior of the surgical device to improve the surgical outcome may be determined, generated, and/or trained using the machine learning, the data collection, and the previous model.

A computing system and/or a method may be provided for applying machine learning to a data collection to improve a surgical outcome. It may be determined from a data collection that may include one or more biomarkers that an operational behavior of a surgical device may be suboptimal or may be improved. A model that may optimize and/or improve the operational behavior of the surgical device and may predict a surgical complication may be determined. For example, the model may be determined using machine learning and the data collection. The model may be updated using feedback given by a healthcare provider (HCP) to improve the model. A control program update may be generated using the model and the data collection. The control program update may be configured to alter a manner in which a control program may operate the surgical device during a surgical procedure to prevent the surgical complication. The control program update may be sent to the surgical device.

In an example, the control program may be a first control program update and the control program update may be a first control program update. A second control program update may be generated using the model and the data collection. The second control program update may be configured to alter the manner in which a second control program operates a sensing system associated with a patient to monitor for the surgical complication. For example, the first control program update may change how the surgical device operates during the surgical procedure to prevent the surgical complication and the second control program update may change how the sensor system monitors the patient.

In an example, a request for feedback may be determined. The request for the feedback may be for a feedback that may result in a faster learning cycle or training cycle for determining the model that may optimize and/or improve the operational behavior of the surgical device and may predict the surgical complication.

In an example, feedback may be given by the HCP provider. The feedback may include a surgical complication verification that may indicate that the HCP agrees with the surgical complication predicted by the model.

In an example, the model may provide a risk level assessment for the surgical complication. The feedback given by the HCP may include a risk level verification that may indicate that the HCP agrees with the risk level assessment for a surgical complication provided by the model. For example, the model may predict that the patient may experience the surgical complication.

In an example, the model may provide a notification level to improve a quality of the model by seeking feedback about the surgical complication from the HCP during the surgical procedure. For example, the model may determine that it may not have enough information regarding a surgical procedure. The model may determine that feedback from the HCP may benefit the model. The model may set and/or determine the notification level such that the notification level may increase the amount of feedback provided by the HCP, for example, to improve the model.

In an example, the model may provide a notification level to prevent a surgical complication by reducing one or more distraction to the HCP during the surgical procedure.

A computing system and/or a method may be provided for applying machine learning to a data collection to improve a surgical outcome. The computing system may comprise a processor. The processor may be configured to perform a number of actions and/or the method. It may be determined that an operational behavior of a surgical device may be suboptimal or may be improved using a surgical device data and a biomarker from a sensing system. A model that improves the operational behavior of the surgical device to improve a surgical outcome may be determined using machine learning, the surgical device data, and the biomarker. The model may be updated using feedback given by an HCP to improve the model. A control program update may be generated and/or determined using the model and the surgical device data. The control program update may be configured to alter a manner in which a control program operates the surgical device during a surgical procedure.

In an example, a data collection improvement may be determined using the biomarker and the feedback. A model may be updated using the data collection improvement. The data collection improvement may be one or more of an improved data set, a data set with improved accuracy, an improved method of data collection, an improved prediction provided by data, a removal of a false positive, an improvement in data filtering, and the like.

In an example, the biomarker may be a first biomarker, and the sensing system may be a first sensing system. A sensor feedback improvement may be determined using the model and the feedback. A second biomarker may be determined from a second sensing system using the sensor feedback improvement. The model may be updated using the second biomarker. The sensor feedback improvement may be an indication that the second sensing system may provide improved biomarker tracking as compared to the first sensing system. The sensor feedback improvement may be an indication that the second biomarker may improve a diagnosis made with the first biomarker, may improve the accuracy of the first biomarker, may be complementary to the first biomarker, may confirm a prediction based on the first biomarker, may be used with the first biomarker to improve a prediction, and the like.

In an example, the surgical outcome may include one or more of a reduced complication for a patient, an improved recovery rate for the patient, a low false positive sensing issue for the sensing system, and the like.

In an example, improving a surgical outcome may include improving a surgical procedure outcome by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Figure 16:
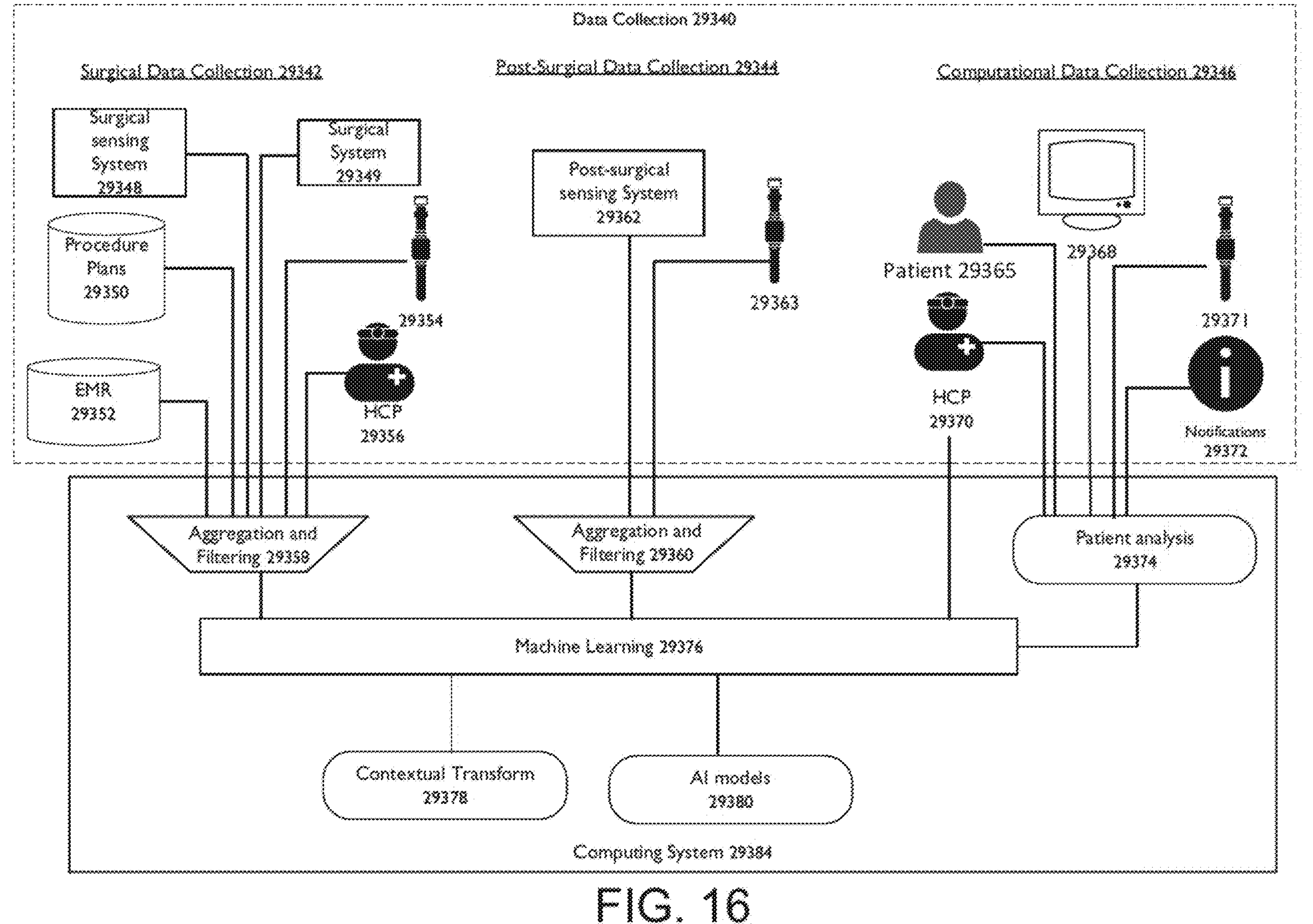
FIG. 16 depicts a flow diagram for applying machine learning to improve one or more patient monitoring measures.

FIG. 16 depicts a flow diagram for applying machine learning to improve one or more patient monitoring measures.

The computing system 29384 may include computing hardware including a processor, memory, input/output subsystems, and the like. The processor may be configured (via application specific hardware, software, firmware, or the like) to transform received data and to derive contextualized for output. For example, the processor may include a microprocessor, a microcontroller, a FPGA, and an application-specific integrated circuit (ASIC), a system-on-a-chip (SOIC), a digital signal processing (DSP) platform, a real-time computing system, or the like. For example, processor may be configured to implement computing functions and/or modules as disclosed herein. For example, the processor may be configured for aggregation and/or filtering 29358, aggregation and/or filtering 29360, machine learning 29376, contextual transform 29378 (e.g., including real-time intra-operative processing), artificial intelligence models 29380, patient analysis 29374, and the like.

The computing system 29384 may be any device suitable for processing sensor, health record data, user input, and the like, before and during surgery, to transform the data and derive computational data for output. The computational output may include a sensor measurement. The computational data may include contextualized data. The computational data may include a context, for example, which may include additional information relevant to the present understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins.

The computing system 29384 may be incorporated with any method suitable for implementation of the functionality disclosed herein. For example, the computing system 29384 may be incorporated as a stand-alone computing system. For example, the computing system may be incorporated into a surgical hub, such as that disclosed in FIG. 1, for example. For example, the computing system 29384 may be incorporated into a sensing system itself (e.g., sensing both pre-surgical and surgical data and providing contextualized data as an output). For example, the computing system 29384 may be incorporated into a surgical device itself (receiving both pre-surgical and surgical data and providing contextualized data and/or alerts as an output).

A data collection, such as data collection 29340 may be provided. Machine learning 29376 may use the data collection, such as data collection 29340. Data collection 29340 may be used by machine learning 29376 to train a model, verify a model, determine a model, and the like.

Data collection 29340 may include one or more data sources. For example, data collection 29340 may include surgical data collection 29342, post-surgical data collection 29344, and computational data 29346. Data collection 29340 may include one or more biomarkers. The one or more biomarkers may come from one or more computing systems, surgical sensing systems, wearable devices, displays, surgical instruments, surgical devices, sensor systems, devices, and the like. The data collection 29340 may include electronic medical records for a patient, data for a patient, data for other patients, data regarding past procedures, data regarding research for procedures, medical data, instructions from a health care provider, plans for a surgery, and the like.

Data collection 29340 may include data from a number of different sources. For example, the sources may include procedure plans database 29350, EMR 29352, surgical sensing system 29348, surgical system 29349, wearable device 29354, data from health care provider 29356, post-surgical sensing system 29362, and wearable device 29363.

Data collection 29340 may include surgical data collection 29342. Surgical data collection 29342 may include data from one or more data sources. Surgical data collection 29342 may include data that may be related a patient that may be recorded during to a surgery. Surgical data collection 29342 may include one or more biomarkers they may have been recorded for a patient during a surgery. For example, a heart rate and blood glucose level for a patient may be recorded for a patient during a surgery.

Surgical data collection 29342 may include data from surgical sensing system 29348. Surgical sensing system 29348 may include any configuration of hardware and software devices suitable for sensing and presenting patient parameters and/or biomarkers that may be relevant before, during, or after a surgical procedure. Such a surgical sensing system 29348 may include any of the sensing and monitoring systems disclosed herein, including uncontrolled patient monitoring systems, controlled patient monitoring systems, and the like. For example, surgical sensing system 29348 may include a wearable patient sensor system. The surgical sensing system 29348 may provide data suitable for establishing baselines of patient biomarkers for use in determining computational data during and/or after surgery. The surgical sensing system 29348 may incorporate or be incorporated into the sensing system 20001 as shown in FIG. 1B.

Surgical data collection 29342 may include data from wearable device 29354. Wearable device 29354 may include any configuration of hardware and software devices suitable for sensing and presenting patent parameters and/or biomarkers that may be relevant before, during, or after a surgical procedure. For example, the wearable device 29354 may provide data suitable for establishing baselines of patient biomarkers for use in determining computational data during and/or after surgery. Wearable device 29354 may include any of those disclosed herein, such as those with reference to FIG. 1B for example.

Surgical data collection 29342 may include procedure plans 29350. Procedure plans 29350 may include any data source relevant to a health procedure (e.g., relevant to a health procedure in view of a particular patient and/or facility). Procedure plan 29248 may include structured data indicative of the desired end result, the surgical tactics to be employed, the operation logistics, and the like. Procedure plan 29350 may include an accounting of the equipment to be used and/or the techniques to be used. Procedure plan 29350 may include an order. Procedure plan 29350 may include a timeline. The structured data may include defined fields and/or data tags associated corresponding values. The structured data may include codes associated with surgical steps.

Surgical data collection 29342 may include EMR 29352. EMR 29352 may include any data source relevant to a patient in view of a health procedure, such a surgical procedure. EMR 29352 may include information such as allergies and/or adverse drug reactions, chronic diseases, family medical history, illnesses and/or hospitalizations, imaging data, laboratory test results, medications and dosing, prescription record, records of surgeries and other procedures, vaccinations, observations of daily living, information collected by surgical sensing system 29348, information collected by wearable device 29354, and the like.

Surgical data collection 29342 may include data from a surgical healthcare provider, such as HCP 29356. Data from HCP 29356 may include any data relevant to a pre-surgical sensing system, a patient record, a procedure plan, and the like. Data from HCP 29356 may include data that may be relevant to an operation, configuration, and/or management of a computing system, such as computing system 29384. For example, data from HCP 29356 include feedback that may be provided to a machine learning module, such a machine learning module 29376. The data from HCP 29356 may include manually entering data that may not be received directly for a relevant source (such as manually entering a manually taken biomarker reading, for example).

Data collection 29340 may include post-surgical data collection 29344. Post-surgical data collection 29344 may include data from one or more data sources. Post-surgical data collection 29344 may include data that is related to a patient that may be recorded after a surgery. Surgical data collection 29344 may include one or more biomarkers they may have been recorded for a patient after a surgery. For example, a heart rate and blood glucose level for a patient may be recorded for a patient after a surgery to monitor post-surgical complications and/or recovery milestones.

Post-surgical data collection 29344 may include one or more data sources. Surgical data collection 29290 may include data from post-surgical sensing system 29362, post-surgical system 29361, and wearable device 29363.

Post-surgical data collection 29344 may include data from post-surgical sensing system 29362. Post-surgical sensing system 29362 may include any configuration of hardware and software devices suitable for sensing and presenting parameters patient biomarkers that may be relevant during a surgical procedure. Post-surgical sensing system 29362 may include the sensing and monitoring systems disclosed herein, including uncontrolled patient monitoring systems, environmental sensing systems, and the like.

Post-surgical data collection 29344 may include data from post-surgical sensing system 29362. post-surgical sensing system 29362 may include any configuration of hardware and software devices suitable for sensing and presenting parameters patient biomarkers that may be relevant after a surgical procedure. Post-surgical sensing system 29362 may include one or more of the sensing and monitoring systems disclosed herein, including controlled patient monitoring systems, surgeon monitoring systems, environmental sensing systems, and the like.

Post-surgical data collection 29344 may include data from wearable device 29363. Wearable device 29363 may include any configuration of hardware and software devices suitable for sensing and presenting patent parameters and/or biomarkers that may be relevant before, during, or after a surgical procedure. Such systems may be used by the patient for any amount of time after surgery, inside and outside of a medical facility. To illustrate, via an uncontrolled patient monitoring system, the patient may use a wearable heart-related sensor at during a surgical procedure. And/or, via a controlled patient monitoring system, a healthcare provider may monitor the same and/or analogous biomarkers using facility equipment during time of the surgical procedure. For example, the wearable device 29363 may provide data suitable for use in determining computational data during and/or after surgery. Wearable device 29363 may include any of those disclosed herein, such as those with reference to FIG. 1B for example.

The data received from the surgical data sources, such as surgical data collection 29342, may be subject to aggregation and/or filtering 29358. Aggregation and/or filtering 29358 may perform pre-processing on data received from surgical data collection 29342. The data received from the surgical data sources, such as post-surgical data collection 29344, may be subject to aggregation and/or filtering 29360. Aggregation and/or filtering 29360 may perform per-processing on data received from post-surgical data collection 29344. Aggregation and/or filtering 29358 and aggregation and/or filtering 29360 may be used to prepare and format the data for use by computing system 29384. For example, aggregation and/or filtering 29358 and aggregation and/or filtering 29360 may prepare data to be processed by machine learning 29376, contextual transform 29378, artificial intelligence models 29380, and patient analysis 29374.

Processing the data received from the surgical data collection 29342 by aggregation and/or filtering 29358 may include filtering (e.g., to select sensor data from the stream of data from surgical sensing system 29348). Aggregation and/or filtering 29358 may use filtering to help reject noise in data from surgical data collection 29342. Aggregation and/or filtering 29358 may use a method to establish a baseline for a biomarker from surgical data collection 29342. Aggregation and/or filtering 29358 may perform time mapping on data from surgical data collection 29342

(e.g., to place received values from different sources in alignment with each other in regard to time). Time mapping may aid in correlation and ratio analysis, which may occur in contextual transform 29378.

Aggregation and/or filtering 29358 may translate data from surgical data collection 29342. The translation of data may include coordinating formats, coordinating data types, translating from one format to another format, translating from one data type, to another data type, accounting for a difference between a data source data format, and accounting for a data type expected by another module, such as machine learning 29376. Translating may include translating the data into a format suitable for machine learning, for artificial intelligence models, for patient analysis, for use by a surgical device control program, and/or for use by a wearable control program. Data from the surgical data collection 29342 may be translated into a notification for display, such as display on a human-interface device 29368. Data from surgical collection 29342 may be translated into data that may be included and/or used for notifications 29372.

Processing the data received from post-surgical data collection 29344 by aggregation and/or filtering 29360 may include filtering (e.g., to select sensor data from the stream of data from post-surgical sensing systems 29362). Aggregation and/or filtering 29360 may use a method to establish a baseline for a biomarker from post-surgical data collection 29344. Aggregation and/or filtering 29360 may use filtering to help reject noise in data from post-surgical data collection 29344. Aggregation and/or filtering 29263 may perform time mapping on data from post-surgical data collection 29344 (e.g., to place received values from different sources in alignment with each other in regard to time). Time mapping may aid in correlation and ratio analysis, which may occur in contextual transform 29278.

Aggregation and/or filtering 29360 may translate data from post-surgical data collection 29344. The translation of data may include coordinating formats, coordinating data types, translating from one format to another format, translating from one data type, to another data type, accounting for a difference between a data source data format, and accounting for a data type expected by another module, such as machine learning 29376. Translating may include translating the data into a format suitable for machine learning, for artificial intelligence models, for patient analysis, for use by a surgical device control program, and/or for use by a wearable control program. Data from the post-surgical data collection 29344 may be translated into a notification for display, such as display on a human-interface device 29368. Data from post-surgical collection 29344 may be translated into data that may be included and/or used for notifications 29372.

Contextual transform 29378 may operate to provide a context for data, such as surgical data collection 29342 and/or post-surgical data collection 29344. For example, contextual transform 29378 may transform data into contextualized surgical data, which may be included in computational data collection 29346. To illustrate, as an input the contextual transform may receive surgical data that includes, for example, a measurement time, a sensor system identifier, and a sensor value. Contextual transform 29378 may output contextualized surgical data. Contextual transform 29378 may output data that may be modified and/or enhanced by machine learning 29376, patient analysis 29374, and artificial intelligence models 29380.

Contextual transform 29378 may determine and/or store data that may be related to each other. Contextual transform 29378 may determine how data may be related to each other. For example, contextual transform 29378 may determine that data from surgical data collection 29342 may be related to data from post-surgical data collection 29344. Contextual transform 29378 may determine a context for the data. Context, for example, additional information relevant to the present understanding and/or interpretation of the sensor measurement.

Computational data collection 29346 may be determined and/or generated by machine learning 29376. For example, machine learning 29376 may receive data from data collection 29340, may apply a machine learning model, and may use the machine learning model to generate the computational data collection 29346.

Computational data collection 29346 may include one or more biomarkers that may be augmented and/or enhanced by a machine learning model. For example, one or more biomarkers may be modified to make the one or more biomarkers more accurate using the machine learning model. Computational data collection 29346 may include one or more predictions and/or probabilities That may be associated with a patient, a surgical outcome, a diagnosis, a morbidity, and the like.

Computation data collection 29346 may include context, for example, additional information relevant to the present understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins.

Computational data collection 29346 may include data that may provide a context. The context may include additional information that may have been created and/determined by machine learning 29360 that may place a biomarker into a specific context for the healthcare providers. For example, computational data collection 29346 may include instructions and/or information about a baseline value for a sensor value, an alert of a deviation, relevant information from the patient's record, relevant information to a procedural element of the surgery, surgical device settings, and/or any information the healthcare provider might find relevant to have at the moment of the sensor's measurement itself. Computational data collection 29346 may include one or more data tags. The data tags may include logging data (indicating that that a specific transform or other processing has occurred).

Computational data collection 29346 may include data that may be provided by HCP 29370. For example, HCP 29370 may provide feedback regarding data provided by machine learning 29376. Computational data collection 29346 may include data that may be sent to HCP 29370. For example, HCP 29370 may receive data provided by machine learning 29376. Data from HCP 29370 may include any data relevant to a wearable device, a machine learning, a patient analysis, a contextual transform, an artificial intelligence model, and the like. For example, HCP 29370 may provide data that may be associated with wearable device 29371, a patent analysis 29374, human-interface device 29368, notifications 29372, computing system 29384, and/or any combination thereof. For example, the HCP 29370 may provide data that may trigger an interaction with the context transform 29378 and/or machine learning 29376. The data from HCP 29370 may include manually entering data not received directly for any relevant source (such as manually entering a manually taken biomarker reading, for example).

Human-interface device 29368 may include any device suitable for producing a perceptible representation of contextualize surgical data, such as contextualized surgical data 29294. The perceptible representation may include a visual indication, an audible indication, or the like. The human-interface device 29368 may include a computer display. For example, the human-interface device 29368 may include a visual representation including text and/or images on a computer display. The human-interface device 29368 may include a text-to-speech device. For example, the human-interface device 29368 may include synthesized language prompt over an audio speaker. The human-interface device 29368 may communicate the contextualized surgical data to the surgeon and/or surgical team. The human-interface device 29368 may include and/or be incorporated into any suitable device disclosed herein. For example, the human-interface device 29368 may include and/or be incorporated into any of the primary display 20023, a first non-sterile human interactive device 20027, and/or a second non-sterile human interactive device 20029, such as that disclosed in FIG. 2A for example. For example, the human-interface device 29368 may include and/or be incorporated into a human interactive device 29368, such as that disclosed in FIG. 2B. For example, the human-interface device 29368 may include and/or be incorporated into the display 20224 of a surgical instrument, such as that disclosed in FIG. 7A for example.

The notifications 29372 may include any device suitable for generating a perceptible indication that relevant contextual data is available and/or has changed. The indication may include a visual indication, an audible indication, a haptic indication, and the like. The notifications 29372 may incorporate any of the human-interface devices 27020 disclosed here. The notifications 29286 may include non-verbal and/or non-textual indications to represent contextual data is available and/or has changed. For example, the alert system may include audio tones, visual color changes, lights, and the like. For example, the notification may include a haptic tap on a wearable device, such as a smartwatch worn by the surgeon. Notifications 29372 may include contextualized data, pre-surgical data, surgical data, and/or post-surgical data. Notifications 29372 may include a request from a machine learning algorithm for a HCP to provide feedback regarding data, a recommendation, And accuracy of an artificial intelligence model, and accuracy of training data, and accuracy of machine learning, a diagnosis, an indication of a problem, data generated by machine learning, a patient analysis, a conclusion regarding a patient analysis, a modification to a surgical device control program, a surgical device control program, wearable control program, any combination thereof, and the like. For example, notifications 29372 may request that HCP 29284 provide feedback regarding machine learning module 29376.

Computational data collection 29346 may include data from wearable device 29371. Wearable device 29371 may include any configuration of hardware and software devices suitable for sensing and presenting patent parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at during a surgical procedure. And/or, via a controlled patient monitoring system, a healthcare provider may monitor the same and/or analogous biomarkers using facility equipment during time of the surgical procedure. For example, the wearable device 29371 may provide data suitable for use in a contextual determination during and/or after surgery. Wearable device 29371 may include any of those disclosed herein, such as those with reference to FIG. 1B for example.

Computational data collection 29346 may include a wearable control program that may have been sent by wearable control programs 29274 to wearable device 29371. Computational data collection 29346 may include an artificial intelligence model that may be sent to wearable device 29280.

The machine learning module 29376 may perform data preparation as described herein for creating and training a model for post-surgical patient analysis using the surgical data collection 29342 and the post-surgical data collection 29340 (e.g., the dataset).

In an example, the data preparation may further include creating a data field and appending it to a (e.g., each) data record in the dataset. The data field may indicate whether there was a post-surgical complication (e.g. a surgical complication that occurred post-surgery) after a respective surgical procedure derived from post-surgical data (e.g., collected from a wearable device 29363 and/or a sensing system 29362. The new data field may serve as a desired output label for training the post-surgical patient analysis AI model 29380 with supervised machine learning for improving patient analysis 29374 (e.g., improved patient monitoring measures).

In such example, the machine learning module 29376 may perform model training, model validation, model testing for a decision tree algorithm-based post-surgical patient analysis AI model 29380. Those of skill in the art will recognize any other suitable machine learning algorithm may be used to build the model 29380. The model 29380 may learn a pattern (e.g., among other patterns) that a post-surgical complication occurs (e.g., anastomotic leak) after a colorectal surgery when a sepsis-related biomarker crosses a first threshold after a first post-surgical threshold period and subsequently crosses a second threshold after a second post-surgical threshold period. For example, a sepsis-related biomarker may be core body temperature, oxygen saturation, heart rate, heart rate variability, or tissue perfusion pressure.

Accordingly, the machine learning module 29376 may be configured to send the HCP 29370 a medium-risk notification 29372 indicating a probability of sepsis when a core body temperature measurement data is detected to have crossed a first threshold after a first post-surgical threshold period by the post-surgical patient analysis AI model 29380 based on post-surgical input data to the model 29380 from actual post-surgical patient monitoring. The machine learning module 29376 may be further configured to send the HCP 29370 a high-risk notification 29372 indicating a probability of sepsis when a core body temperature measurement data is detected to have crossed a second threshold after a second post-surgical threshold period by the model 29380. In such manner, the model 29380 may improve patient monitoring by providing indications of a progressing probability of post-surgical complications. In an example, the HCP 29370 may determine the notifications were incorrect based on the biomarker measurement data and provide feedback to the machine learning module 29376. Further, the machine learning module 29376 may be configured to send the patient 29365 similarly notifications.

In another example, the data preparation may further include using only data records for a patient with an underlying condition (e.g., type 2 diabetes mellitus (T2DM). Accordingly, post-surgical patient analysis AI model 29380 may improve patient monitoring specifically for those patients. In another example, the data preparation may further include using only post-surgical biomarker measurement data collected during exercise. Accordingly, post-surgical patient analysis AI model 29380 may improve patient monitoring specifically as it relates to biomarker monitoring during exercise (e.g., for tracking recovering milestones related to calorie burning after a bariatric surgery).

We claim:

1. A computing system, the computing system comprising:

a processor, the processor configured to:

determine from a data collection that an operational behavior of a surgical stapler is suboptimal, wherein the data collection comprises one or more biomarkers;

determine a machine learning model that predicts a risk of a bleeding complication associated with a patient and optimizes the operational behavior of the surgical stapler based on the data collection;

determine, using the machine learning model, a risk level assessment of the risk of the bleeding complication based on the data collection and a control program of the surgical stapler;

send the risk level assessment to a health care professional (HCP);

receive feedback from the HCP, wherein the feedback comprises a modification to the control program of the surgical stapler and a risk level verification, wherein the risk level verification indicates that the HCP agrees with the risk level assessment;

update the machine learning model based on the feedback;

generate a program update based on the updated machine learning model and the data collection, wherein the program update is configured to cause the surgical stapler to apply an adjusted compression force level during a surgical procedure to reduce the risk of the bleeding complication; and send the program update to the surgical stapler.

2. The computing system of claim 1, wherein the processor is further configured to:

determine that a request for the feedback would result in a faster learning cycle for training the machine learning model; and send the request for the feedback to the HCP.

3. The computing system of claim 1, wherein the processor is further configured to determine from the machine learning model that an advanced instrument operation would reduce the risk of the bleeding complication or improve a recovery rate for the patient, and wherein the program update is further configured to cause the surgical stapler to apply the advanced instrument operation.

4. The computing system of claim 1, wherein the machine learning model further provides a diagnosis for the patient based on the one or more biomarkers, and wherein the feedback given by the HCP further includes a diagnosis verification that indicates that the HCP agrees with the diagnosis provided by the machine learning model.

5. The computing system of claim 1, wherein the machine learning model further provides a notification level to enable improvements in the machine learning model by seeking the feedback from the HCP during the surgical procedure.

6. The computing system of claim 1, wherein the machine learning model further provides a notification level to reduce distractions to the HCP during the surgical procedure.

7. The computing system of claim 1, wherein the machine learning model further provides a notification level to improve a quality of the machine learning model by seeking the feedback from the HCP during the surgical procedure while minimizing distractions to the HCP during the surgical procedure.

8. A computing system for applying machine learning to improve an outcome, the computing system comprising:

a processor, the processor configured to:

determine from a data collection that an operational behavior of a surgical stapler is suboptimal, wherein the data collection comprises one or more biomarkers;

determine a machine learning model that predicts a risk of a bleeding complication associated with a patient, provides a notification level, and optimizes the operational behavior of the surgical stapler using the data collection;

determine, using the machine learning model, a risk level assessment of the risk of the bleeding complication based on the data collection and a control program of the surgical stapler;

send the risk level assessment to a health care professional (HCP);

receive feedback from the HCP, wherein the feedback comprises a modification to the control program of the surgical stapler and a risk level verification, wherein the risk level verification indicates that the HCP agrees with the risk level assessment;

update the machine learning model based on the feedback;

generate a program update based on the updated machine learning model and the data collection, wherein the program update is configured to cause the surgical stapler to apply an adjusted compression force level during a surgical procedure to reduce the risk of the bleeding complication; and send the program update to the surgical stapler.

9. The computing system of claim 8, wherein the processor is further configured to:

determine that a request for the feedback would result in a faster machine learning cycle for determining the machine learning model; and send the request for the feedback to the HCP.

10. The computing system of claim 8, wherein the notification level reduces distractions to the HCP during the surgical procedure.

11. A method performed by a computing system, the method comprising:

determining that an operational behavior of a surgical stapler is suboptimal based on surgical device data and a biomarker;

determining a machine learning model that predicts a risk of a bleeding complication associated with a patient and improves the operational behavior of the surgical stapler based on the surgical device data and the biomarker;

determining, using the machine learning model, a risk level assessment of the risk of the bleeding complication based on the surgical device data and a control program of the surgical stapler;

sending the risk level assessment to a health care professional (HCP);

receiving feedback from the HCP, wherein the feedback comprises a modification to the control program of the surgical stapler and a risk level verification, wherein the risk level verification indicates that the HCP agrees with the risk level assessment;

updating the machine learning model based on the feedback;

generating a program update based on the updated machine learning model and the surgical device data, wherein the program update is configured to cause the surgical stapler to apply an adjusted compression force level during a surgical procedure to reduce the risk of the bleeding complication; and sending the program update to the surgical stapler.

12. The method of claim 11, wherein the method further comprises:

determining a data collection improvement based on the biomarker and the feedback; and updating the machine learning model based on the data collection improvement.

13. The method of claim 11, wherein the biomarker is a first biomarker, and the method further comprises:

determining a sensor feed improvement based on the machine learning model and the feedback;

determining a second biomarker based on the sensor feed improvement; and updating the machine learning model based on the second biomarker.

* * * * *